(12) United States Patent
Sauter et al.

(10) Patent No.: US 12,343,074 B2
(45) Date of Patent: Jul. 1, 2025

(54) METHODS, SYSTEMS, AND APPARATUSES FOR PERFORATING TISSUE STRUCTURES

(71) Applicant: ATRAVERSE MEDICAL INC., Cardiff, IA (US)

(72) Inventors: Eric Douglas Sauter, Carlsbad, CA (US); Steven Richard Mickelsen, Iowa City, IA (US); Jay Lee Kelley, Encinitas, CA (US)

(73) Assignee: Atraverse Medical, Inc., Cardiff, CA (US)

( * ) Notice: Subject to any disclaimer, the term of this patent is extended or adjusted under 35 U.S.C. 154(b) by 0 days.

(21) Appl. No.: 18/444,623

(22) Filed: Feb. 16, 2024

(65) Prior Publication Data
US 2024/0216047 A1    Jul. 4, 2024

Related U.S. Application Data

(63) Continuation-in-part of application No. PCT/US2023/086043, filed on Dec. 27, 2023.

(60) Provisional application No. 63/586,940, filed on Sep. 29, 2023, provisional application No. 63/435,659, filed on Dec. 28, 2022.

(51) Int. Cl.
  *A61B 18/00* (2006.01)
  *A61B 18/14* (2006.01)

(52) U.S. Cl.
  CPC ............. *A61B 18/1492* (2013.01); *A61B 2018/00083* (2013.01); *A61B 2018/00095* (2013.01); *A61B 2018/00148* (2013.01); *A61B 2018/00178* (2013.01); *A61B 2018/00357* (2013.01); *A61B 2018/00714* (2013.01);
  (Continued)

(58) Field of Classification Search
  CPC .......... A61B 2018/00178; A61B 2018/00357; A61B 2018/1475; A61B 2018/1492
  See application file for complete search history.

(56) References Cited

U.S. PATENT DOCUMENTS

| 6,033,403 A | 3/2000 | Tu et al. |
| 6,565,562 B1 | 5/2003 | Shah et al. |

(Continued)

FOREIGN PATENT DOCUMENTS

| EP | 4091569 A1 | 11/2022 |
| WO | WO-2013158354 A1 | 10/2013 |

(Continued)

OTHER PUBLICATIONS

Jauvert, G., et al., "Use of a radiofrequency guidewire to simplify workflow for left atrium access: a case series", Journal of Interventional Cardiac Electrophysiology (2020); 59: 551-556.

(Continued)

*Primary Examiner* — Jaymi E Della
(74) *Attorney, Agent, or Firm* — COOLEY LLP

(57) ABSTRACT

Systems, devices, and methods described relate to a system including an electrosurgical interface electrically coupled to the generator, an energy delivery element electrically coupled to the electrosurgical interface, the energy delivery element configured to receive energy from the generator to form a puncture in tissue of a patient, and a return electrode electrically coupled to the patient and the generator.

19 Claims, 49 Drawing Sheets
(18 of 49 Drawing Sheet(s) Filed in Color)

(52) U.S. Cl.
CPC .............. *A61B 2018/00767* (2013.01); *A61B 2018/00875* (2013.01); *A61B 2018/1475* (2013.01)

(56) References Cited

U.S. PATENT DOCUMENTS

| | | |
|---|---|---|
| 7,048,733 B2 | 5/2006 | Hartley et al. |
| 7,112,197 B2 | 9/2006 | Hartley et al. |
| 7,163,536 B2 | 1/2007 | Godara |
| 7,258,688 B1 | 8/2007 | Shah et al. |
| 7,947,040 B2 | 5/2011 | Davies et al. |
| 7,963,947 B2 | 6/2011 | Kurth et al. |
| 8,308,720 B2 | 11/2012 | Davies |
| 8,500,697 B2 | 8/2013 | Kurth et al. |
| 8,882,755 B2 | 11/2014 | Leung et al. |
| 8,961,550 B2 | 2/2015 | Lenker et al. |
| 9,168,085 B2 | 10/2015 | Juzkiw et al. |
| 9,707,007 B2 | 7/2017 | Lenker et al. |
| 9,993,266 B2 | 6/2018 | Lenker et al. |
| 10,173,033 B2 | 1/2019 | Leung et al. |
| 10,206,739 B2 | 2/2019 | Godara et al. |
| 10,362,959 B2 | 7/2019 | Aiken et al. |
| 10,368,911 B2 | 8/2019 | Davies et al. |
| 10,485,569 B2 | 11/2019 | Lenker et al. |
| 10,485,579 B2 | 11/2019 | Lenker |
| 10,729,457 B2 | 8/2020 | Lenker et al. |
| 10,779,858 B2 | 9/2020 | Lenker et al. |
| 10,792,096 B2 | 10/2020 | Davies et al. |
| 10,820,925 B2 | 11/2020 | Urbanski et al. |
| 10,898,291 B2 | 1/2021 | Davies et al. |
| 11,090,080 B2 | 8/2021 | Lenker et al. |
| 11,103,276 B2 | 8/2021 | Sarabia et al. |
| 11,224,725 B2 | 1/2022 | Pedersen et al. |
| 11,234,728 B2 | 2/2022 | Lenker et al. |
| 11,234,761 B2 | 2/2022 | Leung et al. |
| 11,318,302 B2 | 5/2022 | Asleson et al. |
| 11,324,548 B2 | 5/2022 | Uhm et al. |
| 11,382,654 B2 | 7/2022 | Lenker |
| 11,426,565 B2 | 8/2022 | Thomspon Smith et al. |
| 11,490,922 B2 | 11/2022 | Lenker et al. |
| 11,497,549 B2 | 11/2022 | Urbanski et al. |
| 11,540,861 B2 | 1/2023 | Sapir |
| 11,583,249 B2 | 2/2023 | Altmann |
| 11,666,377 B2 | 6/2023 | Davies et al. |
| 11,666,733 B2 | 6/2023 | Maini et al. |
| 11,684,766 B2 | 6/2023 | Arnett et al. |
| 11,766,290 B2 | 9/2023 | Urbanski et al. |
| 11,793,446 B2 | 10/2023 | MacDonald et al. |
| 11,801,087 B2 | 10/2023 | Urbanski et al. |
| 11,937,873 B2 | 3/2024 | Davies et al. |
| 2001/0016740 A1* | 8/2001 | Dittrich .............. A61B 18/1485 606/46 |
| 2004/0092973 A1 | 5/2004 | Chanduszko et al. |
| 2004/0176759 A1 | 9/2004 | Krishnamurthy et al. |
| 2007/0203479 A1* | 8/2007 | Auth .................. A61B 18/1492 606/41 |
| 2009/0093802 A1* | 4/2009 | Kulesa ................ A61B 18/1492 606/41 |
| 2013/0304051 A1 | 11/2013 | Kimmel et al. |
| 2014/0228841 A1* | 8/2014 | Davies ................ A61B 17/3478 606/45 |
| 2018/0103985 A1 | 4/2018 | Maini |
| 2018/0344353 A1 | 12/2018 | Hassett |
| 2019/0029722 A1 | 1/2019 | Maini |
| 2019/0029750 A1 | 1/2019 | Maini |
| 2019/0099195 A1 | 4/2019 | Carroll et al. |
| 2019/0274754 A1 | 9/2019 | Davies et al. |
| 2020/0060710 A1* | 2/2020 | Urbanski ........... A61B 17/3205 |
| 2020/0297412 A1 | 9/2020 | Maini |
| 2020/0399495 A1 | 12/2020 | Maini |
| 2021/0000505 A1 | 1/2021 | Lenker et al. |
| 2021/0085384 A1 | 3/2021 | Maini |
| 2021/0100981 A1 | 4/2021 | Maini et al. |
| 2021/0137547 A1 | 5/2021 | Carroll et al. |
| 2021/0186365 A1 | 6/2021 | Kinio et al. |
| 2021/0187248 A1 | 6/2021 | Kinio et al. |
| 2021/0259671 A1 | 8/2021 | DiCicco et al. |
| 2021/0259732 A1 | 8/2021 | DiCicco et al. |
| 2021/0290268 A1 | 9/2021 | Lau et al. |
| 2021/0330355 A1 | 10/2021 | Leung et al. |
| 2021/0353354 A1 | 11/2021 | Schuler et al. |
| 2021/0353355 A1 | 11/2021 | Schuler et al. |
| 2021/0353356 A1 | 11/2021 | Schuler et al. |
| 2021/0353913 A1 | 11/2021 | Balkovec |
| 2021/0369298 A1 | 12/2021 | Sarabia et al. |
| 2021/0393247 A1 | 12/2021 | Moriyama et al. |
| 2021/0393248 A1 | 12/2021 | Moriyama |
| 2021/0393324 A1 | 12/2021 | Moriyama et al. |
| 2021/0401483 A1 | 12/2021 | Highsmith et al. |
| 2022/0000549 A1 | 1/2022 | Wang et al. |
| 2022/0022913 A1 | 1/2022 | Chehade |
| 2022/0022914 A1 | 1/2022 | Miller et al. |
| 2022/0047324 A1 | 2/2022 | Miller et al. |
| 2022/0061884 A1 | 3/2022 | Howard et al. |
| 2022/0061911 A1 | 3/2022 | Howard et al. |
| 2022/0080161 A1 | 3/2022 | Pedersen et al. |
| 2022/0087733 A1 | 3/2022 | Azam |
| 2022/0110577 A1 | 4/2022 | Highsmith et al. |
| 2022/0151655 A1 | 5/2022 | Lenker et al. |
| 2022/0151687 A1 | 5/2022 | Davies |
| 2022/0160389 A1 | 5/2022 | Lenker et al. |
| 2022/0257313 A1 | 8/2022 | Davies et al. |
| 2022/0265316 A1 | 8/2022 | Sapir et al. |
| 2022/0354533 A1 | 11/2022 | Lenker |
| 2022/0355087 A1 | 11/2022 | Thompson Smith et al. |
| 2022/0370121 A1 | 11/2022 | Highsmith |
| 2022/0387764 A1 | 12/2022 | Bonner et al. |
| 2023/0040020 A1 | 2/2023 | Urbanski et al. |
| 2023/0041021 A1 | 2/2023 | Urbanski et al. |
| 2023/0057147 A1 | 2/2023 | Lenker et al. |
| 2023/0079488 A1 | 3/2023 | Urbanski et al. |
| 2023/0130473 A1 | 4/2023 | Balkovec et al. |
| 2023/0143116 A1 | 5/2023 | Leung et al. |
| 2023/0149675 A1 | 5/2023 | Leung et al. |
| 2023/0165625 A1 | 6/2023 | Abou Marie et al. |
| 2023/0165629 A1* | 6/2023 | Tehrani ................ A61B 18/148 606/34 |
| 2023/0166090 A1 | 6/2023 | Leung et al. |
| 2023/0172594 A1 | 6/2023 | DiCicco et al. |
| 2023/0172658 A1 | 6/2023 | Luk et al. |
| 2023/0181244 A1 | 6/2023 | Balkovec et al. |
| 2023/0190330 A1 | 6/2023 | Moriyama et al. |
| 2023/0200845 A1 | 6/2023 | Klein et al. |
| 2023/0218339 A1 | 7/2023 | Moriyama et al. |
| 2023/0233253 A1 | 7/2023 | Moriyama et al. |
| 2023/0241349 A1 | 8/2023 | DiCicco |
| 2023/0255683 A1 | 8/2023 | Warikoo |
| 2023/0255685 A1 | 8/2023 | Mok et al. |
| 2023/0285074 A1 | 9/2023 | Leung et al. |
| 2023/0338082 A1 | 10/2023 | DiCicco et al. |
| 2023/0371936 A1 | 11/2023 | Pedersen et al. |
| 2024/0000497 A1 | 1/2024 | Levy et al. |
| 2024/0032985 A1 | 2/2024 | Koon et al. |
| 2024/0081896 A1 | 3/2024 | Leonardi |
| 2024/0108287 A1 | 4/2024 | Urbanski et al. |
| 2024/0206906 A1 | 6/2024 | Highsmith et al. |

FOREIGN PATENT DOCUMENTS

| | | |
|---|---|---|
| WO | WO-2015145332 A1 | 10/2015 |
| WO | WO-2019035993 A1 | 2/2019 |
| WO | WO-2021152474 A1 | 8/2021 |
| WO | WO-2021152478 A1 | 8/2021 |
| WO | WO-2021161154 A1 | 8/2021 |
| WO | WO-2021174206 A1 | 9/2021 |
| WO | WO-2021255604 A1 | 12/2021 |
| WO | WO-2022009074 A1 | 1/2022 |
| WO | WO-2022013791 A1 | 1/2022 |
| WO | WO-2022018599 A1 | 1/2022 |
| WO | WO-2022024031 A1 | 2/2022 |
| WO | WO-2022034441 A1 | 2/2022 |
| WO | WO-2022038468 A1 | 2/2022 |
| WO | WO-2022049519 A1 | 3/2022 |
| WO | WO-2022053897 A1 | 3/2022 |

(56) References Cited

FOREIGN PATENT DOCUMENTS

| WO | WO-2022090896 A1 | 5/2022 |
|---|---|---|
| WO | WO-2022153082 A1 | 7/2022 |
| WO | WO-2023099421 A1 | 6/2023 |
| WO | WO-2023170273 A1 | 9/2023 |
| WO | WO-2023175478 A1 | 9/2023 |
| WO | WO-2024054623 A2 | 3/2024 |
| WO | WO-2024145362 A2 | 7/2024 |

OTHER PUBLICATIONS

Invitation to pay additional fees for International Application No. PCT/US2023/086043, dated May 7, 2024, 11 pages.
Khan, J.M. et al., "Transcatheter Electrosurgery JACC State-of-the-Art Review", Journal of the American College of Cardiology, vol. 75, No. 12, Mar. 31, 2020, pp. 1455-1470.
International Search Report and Written Opinion for PCT Application No. PCT/US2023/086043 mailed Jun. 28, 2024, 18 pages.
Knight, B., P., et al., "Comparison of transseptal puncture using a dedicated RF wire versus a mechanical needle with and without electrification in an animal model", Journal of Cardiovascular Electrophysiology (2024); 35(1): 16-24.
Wasserlauf, J., et al., "Comparing the safety and effectiveness of dedicated radiofrequency transseptal wires to electrified metal guidewires", Journal of Cardiovascular Electrophysiology (2022); 33(3): 371-379.

\* cited by examiner

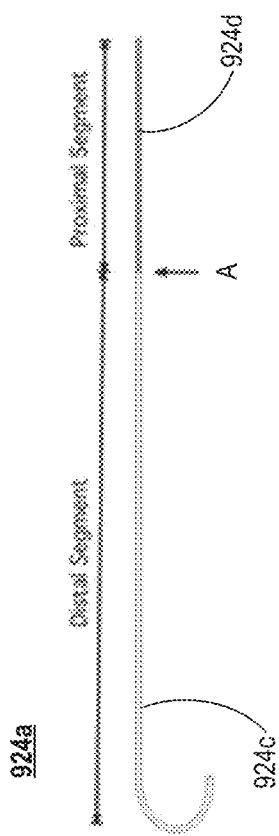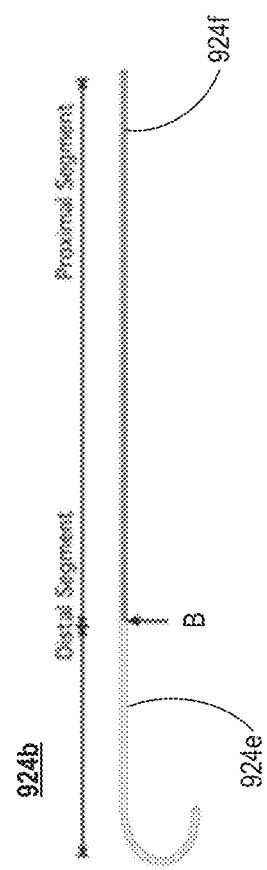

METHODS, SYSTEMS, AND APPARATUSES FOR PERFORATING TISSUE STRUCTURES

CROSS-REFERENCE TO RELATED APPLICATIONS

This application is a continuation-in-part of International Patent Application No. PCT/US2023/086043, filed Dec. 27, 2023, titled "METHODS, SYSTEMS, AND APPARATUSES FOR PERFORATING TISSUE STRUCTURES," which claims priority to and the benefit of U.S. Provisional Patent Application No. 63/435,659, filed Dec. 28, 2022, titled "METHODS, SYSTEMS, AND APPARATUSES FOR PERFORATING TISSUE STRUCTURES," and U.S. Provisional Patent Application No. 63/586,940, filed Sep. 29, 2023, titled "METHODS, SYSTEMS, AND APPARATUSES FOR PERFORATING TISSUE STRUCTURES," the disclosure of each of which is incorporated herein by reference.

TECHNICAL FIELD

The embodiments described herein relate generally to medical devices for electrical energy delivery, and more particularly to systems, apparatuses, and methods for perforating and to cross through tissue structures, including, for example, performing transseptal puncture during cardiac interventions.

BACKGROUND

In many medical procedures, it may be necessary to puncture through a tissue structure to gain access to treatment sites or create passageways or connections between different anatomical structures. For example, in cardiac interventions, a needle, catheter, or guidewire is commonly used to puncture through the atrial septum to gain access to the left side of the heart, e.g., for evaluating or treating cardiac anomalies. In some instances, the guidewire or catheter can be equipped with an energy delivery device that can deliver energy such as radiofrequency (RF) energy to a tissue structure, such as the septum, to perforate through it.

While there are existing systems capable of perforating and crossing through tissue structures, such systems suffer from various drawbacks. For example, such systems may cause unwanted injury to other areas of the heart from inadvertent perforation or lead to char or thrombus formation due to high operating temperatures. Such systems may also involve complicated connections between the catheters, guidewires, and/or other energy delivery components and electrosurgical generators. The costs involved with manufacturing many systems are also high. Therefore, there exists further improvements to such systems.

SUMMARY

In one embodiment, a guidewire includes a distal tip and a conductive core coupled to the distal tip. The conductive core is configured to deliver to the distal tip radiofrequency (RF) current from a generator coupled to a proximal portion of the guidewire. the guidewire further includes a conductive outer region disposed near, and coupled to, the distal tip and an insulating collar disposed between the distal tip and the conductive outer region. The guidewire is distally extendable out of an insulating shaft by a first distance in which the distal tip is exposed without exposing the conductive outer region, the guidewire when extended the first distance being configured to deliver RF energy via the distal tip to tissue to perforate the tissue. The guidewire is distally extendable out of the insulating shaft by a second distance greater than the first distance in which the distal tip and at least a portion of the conductive outer region are exposed, such that an exposed surface area of the portion of the conductive outer region is configured to reduce a RF current density around the distal tip In one embodiment, a guidewire includes a distal tip and a conductive core coupled to the distal tip. and a first conductive outer region coupled to the conductive core. The first conductive outer region is slidably receivable within a passage of an electrosurgical interface that is configured to couple the first conductive outer region to a generator such that radiofrequency (RF) current from the generator can be delivered via the first conductive outer region and the conductive core to the distal tip. The guidewire includes a second conductive outer region disposed near, and coupled to, the distal tip, and an insulating outer region disposed between the first and second conductive outer regions. The guidewire is distally extendable out of an insulating shaft by a first distance in which the distal tip is exposed without exposing the second conductive outer region, the guidewire when extended the first distance being configured to deliver RF energy via the distal tip to tissue to perforate the tissue. The guidewire is distally extendable out of the insulating shaft by a second distance greater than the first distance in which the distal tip and at least a portion of the second conductive outer region are exposed, such that an exposed surface area of the portion of the second conductive outer region is configured to reduce a RF current density around the distal tip.

In one embodiment, a system includes an insulating shaft including a proximal end and a distal end and defining a lumen therethrough, and a guidewire configured to be slidably disposed within the lumen. The guidewire is configured to be advanced distally relative to the insulating shaft to expose a distal tip of the guidewire, the distal tip of the guidewire, when exposed, configured to deliver radiofrequency (RF) energy to a septum of a subject to perforate the septum. The system includes an electrosurgical interface coupled to the proximal end of the insulating shaft and a generator. The electrosurgical interface includes a passage aligned with the lumen of the insulating shaft such that the guidewire can extend through the passage and the lumen of the insulating shaft. The electrosurgical interface is configured to establish an electrical coupling between the generator and the guidewire and to maintain the electrical coupling while the guidewire is advanced distal to the distal end of the insulating shaft. The system includes an activation device configured to, in response to be activated when the distal tip is exposed, cause the generator to deliver RF current to the guidewire via the electrical coupling to cause the distal tip to deliver the RF energy to perforate the septum.

In some embodiment, a method includes extending a distal end of a guidewire disposed within an insulating sheath a first distance distal to a distal end of the insulating sheath, the distal end of the guidewire and the distal end of the insulating sheath being disposed proximate to a septum of a heart. The method includes disposing the distal tip of the guidewire against the septum. The method includes delivering, after disposing the distal tip of the guidewire against the septum, radiofrequency (RF) energy to the septum via the distal tip. The method includes further extending the distal dip of the guidewire distally while delivering the RF energy to form a perforation in the septum. The method includes, in response to extending the distal tip of the guidewire a second distance distal to the distal end of the insulating sheath, exposing at least a portion of a conductive outer region of the guidewire such that an exposed surface area of the portion of the conductive outer region reduces a RF current density around the distal tip of the guidewire.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 9A and 9B depict different examples of guidewires of an electrosurgical device, according to embodiments.

DETAILED DESCRIPTION

Figure 1:
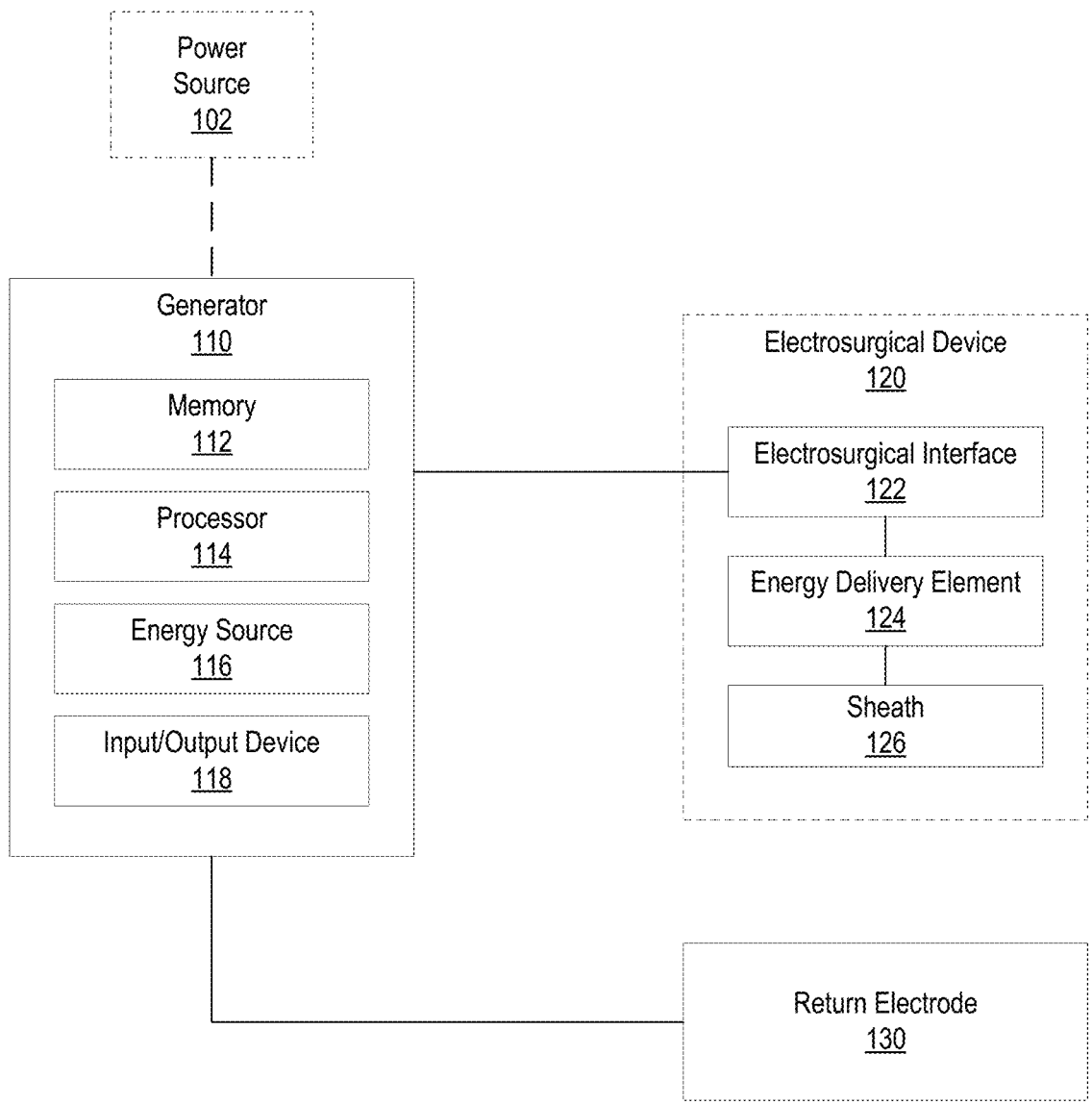
FIG. 1 is a schematic diagram of an electrosurgical system, according to embodiments.

Described in various embodiments herein, are systems, devices, device components, and methods for puncturing and crossing tissue structures, including, for example, thin tissue structures such as the atrial septum. In particular, electrosurgical systems are configured to puncture and cross thin tissue structures for biomedical applications. Aspects of these embodiments may provide for a safer, faster or more convenient tissue puncture.

An example use for electrosurgical systems, assemblies and devices as described herein is to facilitate transseptal puncture procedures (e.g., atrial crossing). Performing transseptal puncture, also known as atrial crossing, is a necessary procedural step for a myriad of cardiac interventions, including cardiac ablation for treatment of arrythmias such as atrial fibrillation and atrial flutter, occlusion of the left atrial appendage, and transcatheter repair of the mitral valve. These diseases and others affect millions of people worldwide. For transcatheter therapies of the left side of the heart, a direct pathway from the large diameter vena cava can be utilized to deliver large bore sheaths and devices (e.g., about 8-12 French) to the right atrial chamber. After the catheter is delivered to the right side of the heart, a small puncture is then made in the interatrial septum dividing the left and right sides of the heart to gain access to the left side of the heart. The inter atrial septum is composed of a thin fibrous structure known as the fossa ovalis (FO).

The most widely used approach for puncturing the septum is by inserting a long guide catheter over a guidewire into the heart. The guide catheter is manipulated to position the distal tip in the FO. Once the FO position is achieved and confirmed by fluoroscopic or ultrasound imaging, the guidewire is removed and replaced with a long rigid needle known as a transseptal needle. Since the transseptal needle is rigid, manual shaping outside of the body may be required to achieve the desired position on the FO. Using the transseptal needle, mechanical force is applied, and the sharp distal end of the needle punctures the FO. Once the puncture is made, the transeptal needle is removed, and a guidewire is re-inserted and its distal tip is advanced into the left atrium. With this guidewire in place, a range of therapeutic devices may be delivered to the left atrium based on the preferences of the physician and the treatment to be performed.

Mechanical systems that rely on a rigid needle, however, have certain drawbacks and may not always be effective at puncturing through the septum. Moreover, such systems require additional components (e.g., rigid needle) to facilitate puncture and crossing of the septum. In contrast, electrosurgical systems described herein can effectively puncture and cross through the septum to facilitate delivery of other therapeutic devices.

There are several advantages of electrosurgical systems, assemblies and devices described herein. By combining the guiding and puncture functions into one tool or device, at least one device exchange may be eliminated. With each device exchange (i.e., taking one device out of the patient and replacing with another), there is an increased risk of undesirable events such as air embolism leading to stroke, inadvertent puncture of the vasculature, or loss of device position resulting in increased procedure time. Since the distal end of the novel electrosurgical guide wire is flexible (e.g., sufficiently flexible to follow the shape of a sheath and/or dilator), it may be used in conjunction with a steerable guide catheter or sheath, without the need to remove the device from the body for manual shaping. The ability of the flexible distal tip to be steered and manipulated with the sheath facilitates accurate positioning on the FO and optimal crossing location for various patient anatomies.

Certain electrosurgical systems use electrosurgical guidewires that are inserted in a dilator and connected to an electrosurgical generator with a spring-loaded clip. The generator can apply RF energy to the distal tip of the electrosurgical guidewire when a button on the generator or a footswitch is depressed. Electrosurgical systems described herein improve upon such electrosurgical systems in several ways. First, the electrosurgical systems described herein include an interface for coupling the energy delivery element to a generator in which the energy delivery element can slide relative to a fixed electrode within the interface, thereby allowing the energy delivery element to be easily advanced or retracted. In some embodiments, the interface can couple to the back of the energy delivery element so that the energy delivery element can be easily directed. Second, the energy delivery element such as a guidewire used in systems described herein can be manufactured using batch processes for coating and plating, which facilitates manufacturing of a lower cost device. Third, systems described herein can include buttons or other actuation mechanisms that are physically close to the sheath, enabling a single user to control both the timing of the electrosurgical energy delivery and the position of the guidewire from one location. Moreover, the actuation mechanism can be located on a single device as the electrosurgical energy connector or interface (instead of on a generator control panel or foot switch coupled to the generator), such that a single cable can be used to provide necessary electrical connections to the generator. Fourth, the energy delivery element such as a guidewire used in systems described herein can have a coiled design that has a large surface area and, when plated with an efficient thermal conductor such as gold, can have improved heat transfer, which lowers the operating temperature of the electrosurgical tip during therapy. Such can reduce the risk of char or thrombus formation due to excessive temperatures. Fifth, the guidewire used in systems described herein can have an insulating collar that allows for the tip of the guidewire to direct RF energy during therapy. Sixth, given that the electrical connection between the generator and the electrosurgical device allows a physician to easily slide or move the guidewire without added interference, a physician can rely on tactile feedback (e.g., as a result of guidewire tip's behavior) to assess when the guidewire is in contact with a tissue surface.

Further details of the electrosurgical systems, devices, and methods described herein are provided in the sections below.

Electrosurgical System and Devices

FIG. 1 is a schematic diagram of an electrosurgical system 100, according to embodiments. The electrosurgical system 100 includes a generator 110, an electrosurgical device or assembly 120, and a return electrode 130.

The generator 110 can be configured to generate energy, such as, for example, radiofrequency (RF) energy. The generator 110 can include a memory 112, a processor 114, an energy source 116, and an input/output device 118. In some embodiments, the generator 110 can be coupled to an external power source 102, such as, for example, a direct current (DC) power supply. The generator 110 can include a plug or adaptor, which can be used to plug into a socket. Alternatively, or additionally, the generator 110 can include an onboard power source, such as, for example, a battery.

The memory 112 may include a database (not shown) and may be, for example, a random access memory (RAM), a memory buffer, a hard drive, an erasable programmable read-only memory (EPROM), an electrically erasable read-only memory (EEPROM), a read-only memory (ROM), Flash memory, etc. The memory 112 may store instructions to cause the processor 114 to execute modules, processes and/or functions associated with the system 100, such as voltage waveform generation and/or impedance monitoring, as further described below.

The processor 114 can be any suitable processing device configured to run and/or execute a set of instructions or code. The processor may be, for example, a general purpose processor, a Field Programmable Gate Array (FPGA), an Application Specific Integrated Circuit (ASIC), a Digital Signal Processor (DSP), and/or the like. The processor may be configured to run and/or execute application processes and/or other modules, processes and/or functions associated with the system and/or a network associated therewith (not shown). The underlying device technologies may be provided in a variety of component types, e.g., metal-oxide semiconductor field-effect transistor (MOSFET) technologies like complementary metal-oxide semiconductor (CMOS), bipolar technologies like emitter-coupled logic (ECL), polymer technologies (e.g., silicon-conjugated polymer and metal-conjugated polymer-metal structures), mixed analog and digital, and/or the like.

The energy source 116 can be configured to convert, store, and/or supply energy, e.g., in the form of a voltage waveform. In some embodiments, the energy source 116 can include an alternating current (AC)/DC switcher. In some embodiments, the energy source 116 can include one or more capacitors to store energy from a power supply. In some embodiments, the energy source 116 can be configured to generate and deliver voltage waveforms, e.g., to the electrosurgical device 120. In some embodiments, the voltage waveform can be an oscillating sinusoidal RF waveform. The voltage waveform can have a frequency of between about 200 kHz to about 1 MHz, including all sub-ranges and values therebetween. For example, the voltage waveform can have a frequency of between about 350 kHz and about 500 kHz, or a frequency of about 450 kHz, in some applications. The voltage waveform can have a peak voltage of between about 100 V and about 400 V, including all sub-ranges and values therebetween. For example, the voltage waveform can have a peak voltage of between about 150 V to about 250 V, or a peak voltage of about 200 V, in some applications.

The input/output device 118 can be configured to provide a communication interface between an operator and the system 100. The input/output device 118 can include one or more input devices and output devices. In some embodiments, an input device of the input/output device 118 may include a touchscreen or other touch-sensitive device, a step switch, a foot pedal, a keypad, a keyboard, a button, a joystick, etc. In some embodiments, an output device of the input/output device 118 may include one or more of a display device and audio device. The display device may include at least one of a light emitting diode (LED), liquid crystal display (LCD), electroluminescent display (ELD), plasma display panel (PDP), thin film transistor (TFT), and organic light emitting diodes (OLED). An audio device may audibly output patient data, sensor data, system data, other data, alarms, warnings, and/or the like. The audio device may include at least one of a speaker, piezoelectric audio device, magnetostrictive speaker, and/or digital speaker.

The generator 110 can be coupled to the electrosurgical device 120 and the return electrode 130. In use, the signal generator 110 is configured to generate voltage waveforms for puncturing through tissue, such as, for example, the atrial septum. For example, the generator 110 may be configured to generate and deliver a voltage waveform to the electrosurgical device 120. The return electrode 130 may be coupled to a patient (e.g., disposed on a patient's back, torso, or extremity such as a leg) to allow current to pass from the electrosurgical device 120 through the patient and then to the return electrode 130 to provide a safe current return path from the patient.

In some embodiments, the generator 110 can operate in a constant power mode with a typical setting of about 5 to about 25 W. In some embodiments, the generator 110 can implement a feedback loop control, e.g., via a controller of the generator or a controller operatively coupled to the generator. For example, the generator 110 (or controller) can include circuitry configured to determine an impedance of the circuit going from the generator 110 to the electrosurgical device 120 and to the return electrode 130 and back to the generator 110. The processor 114 or other processing circuitry within the generator 110 can be configured to monitor the impedance of the circuit and modulate the voltage output to not exceed a preset or predetermined electrical power ($P_{max}$). In some embodiments, $P_m$ax can be between about 5 W and about 100 W, including all sub-ranges and values therebetween. For example, $P_{max}$ can be between about 45 W and about 55 W, or about 50 W. During an electrosurgical treatment, the impedance of the circuit may begin at about 1500 Ohms but then rise to 2000 Ohms as the biophysical characteristics of the tissue target changes. For example, the impedance can change as the energy delivery device or guidewire touches tissue, cuts through tissue, and then arrives in the blood pool. As such, the generator 110 can be configured to monitor this change in impedance and adjust the parameters of the voltage waveform. In some embodiments, the generator 110 can be configured to modify the RF output based on a characteristic (e.g., output current, current density, temperature, etc.) of the energy delivery element 124. Some electrosurgical waveform generators may operate in constant power control modes, e.g., where the impedance of the circuit is continually measured and the voltage of the RF waveform is adjusted to produce a fixed electrical power. For example, in an application involving a generator set to produce a constant power of 50 W, the voltage of the voltage waveform may dramatically rise to a maximum voltage, $V_{max}$, of 3000 V (peak-to-peak) or greater to produce the constant power of 50 W with increases in tissue impedance. This can present complications, as any connected electrosurgical device must have sufficient electrical insulation to protect against dielectric breakdown or current leakages, which can be hazardous to the patient or operator at high voltages. High voltages associated with these power-controlled electrosurgical generators may produce sparking and fulguration at the tip of the guidewire, which can produce significant gas bubbles, coagulum, and char formation. For an intravascular device within the left atrial chamber of the heart, these can lead to ischemic stroke or other complications. In some embodiments, the generator is configured to vary the RF output after time. For example, the generator can provide a first output for a first period of time, a second output for a second period of time, a third output for a third period of time, and/or so on.

Given the lower operating voltages of the generator 110 and the use of a feedback control scheme that maintains power below a predetermined peak power, systems and devices described herein can be used with electrosurgical devices having smaller profiles. For example, the generator 110, by operating with lower voltages (e.g., voltages between about 150 V and about 250 V), can allow for the use of electrosurgical devices with smaller insulators or less insulating material. In particular, the ability of an insulated wire to resist dielectric breakdown is directly related to the thickness of the insulator. As such, with lower voltages, electrosurgical wires with thinner insulative coating can be used. In some embodiments, the coating thickness of the guidewires can be negligible compared to the diameter of the core of the guidewires, which can result in improved mechanical characteristics of the energy delivery element 122. Furthermore, since the insulator is thin, it may be applied to the guidewire core via low-cost manufacturing techniques such as dip or spray coating.

In some embodiments, the generator 110 can be configured to modulate the voltage output based on a temperature of a distal tip of the energy delivery element 124. As noted above, using a RF powered guidewire or needle to create an atrial-septal defect (e.g., for transseptal access) can cause thromboembolic risk by generating inadvertent char and/or coagulum. Char and coagulum are created when tissue reaches temperatures above a threshold, which causes protein denaturation, dehydration, and thrombogenic cascade. Maintaining the tip temperature below that threshold would prevent the formation of char and coagulum, and thus avoid thromboembolic risk to the patient. Therefore, in some embodiments, the generator 110 can be configured to deliver a voltage output to the energy delivery element 124 until a target set point temperature or range is reached. In some embodiments, the target set point temperature or range can be between about 55 and about 80 degrees Celsius. In operation, the RF output from the generator can be initiated by a user, e.g., by actuating an actuator (e.g., button or slider which may be located on the electrosurgical interface 122 described below), when the guidewire is located at the desired area of tissue contact. The generator 110 can then deliver current to reach the target set point temperature. By avoiding temperatures above about 80 degrees Celsius, the incidence of char and coagulum formation can be reduced or avoided. Further details of implementing a temperature control are described with reference to FIG. 36. In an embodiment, the electrosurgical system includes both a power-limited generator and a low-voltage tip.

The electrosurgical device or assembly 120 can include an electrosurgical interface 122, an energy delivery element 124, and a sheath 126. While the electrosurgical device 120 is described as a single device, it can be appreciated that each of the electrosurgical interface 122, energy delivery element 124, and sheath 126 can be implemented as separate devices and/or components of two or more devices.

The electrosurgical interface 122 establishes electrical connectivity between the generator 110 and the energy delivery element 124 while allowing for slidable translation of the energy delivery element 124 therethrough. The electrosurgical interface 122 can be coupled to, coupleable with, or include a cable that connects to the generator 110 and an interface for receiving the energy delivery element 124. The interface 122, as depicted in greater detail in FIGS. 3A-3C, can include an electrical coupling element that is electrically connected to the generator 110 (e.g., via the cable). In an embodiment, the electrical coupling element is an electrode and the electrosurgical interface 122 includes a layer of conductive fluid in electrical contact with the electrode. The energy delivery element 124 can then be received within the conductive fluid and be electrically coupled to the electrode via the conductive fluid. The energy delivery element 124 is slidable within the conductive fluid, without loss in the electrical coupling with the electrode. In some embodiments, electrical coupling between the energy delivery element 124 and the electrosurgical interface 122 can include direct coupling, fluid coupling, induction coupling, or the like. In some embodiments, the interface 122 can be electrically coupled to the end of the energy delivery element 124. Further details of the electrosurgical interface 122 are provided below, with respect to FIGS. 3A-3C.

In some embodiments, the electrosurgical device 120 can include a button, slider, or other actuation device for establishing the electrical connection between the generator 110 and the electrosurgical interface 122. For example, a button or slider can be provided on the electrosurgical device 120, e.g., near where a user may be manipulating the energy delivery element 124 and/or other components of the electrosurgical device 120, and the button can be pressed or the slider can be slid to establish electrical connection between the generator 110 and the electrode of the electrosurgical interface 122. Alternatively, or additionally, a button, slider, or other actuation device can be actuated to send a signal to the generator 110, e.g., via a wired or wireless connection to the generator 110. In some embodiments, the signal can be an activation (on or off) signal. In some embodiments, the signal can trigger the generator 110 to send RF energy (e.g., a pulse waveform) to the electrosurgical device 120. In some embodiments, the signal can be a voltage signal, a current signal, or an impedance signal, which can be communicated to the generator 110 and the generator 110, in response to receiving the signal, can deliver a RF waveform to the electrosurgical device 120. In some embodiments, the electrosurgical interface 122 and the generator 110 are configured to communicate to identify the type and/or information regarding the electrosurgical interface 122, generator 110, and/or the energy delivery element 124. For example, the generator 110 can determine if the energy delivery element 124 has been previously used for a procedure. In some embodiments, the generator 110 may be configured to prevent reuse of the energy delivery element 124 to decrease the chance of contamination.

In some embodiments, the electrosurgical interface 122 can include a cutting feature to remove portions of an insulating jacket of the energy delivery element 124 to electrically couple to the energy delivery element 124. In some embodiments, the electrosurgical interface 122 can include a button, that when activated, operates a cutting blade to expose a conductive portion of the energy delivery element 124.

The energy delivery element 124 can include an electrode or other conductive element for applying energy to a tissue structure. In embodiments, the energy delivery element 124 is a wire (e.g., guidewire) that includes a distal conductive tip that is used to apply energy to and thereby puncture through tissue structures. In some embodiments, the energy delivery element 124 includes a distal tip that can transition between different configurations or shapes, e.g., a curved configuration vs. a straight configuration. In some embodiments, the energy delivery element 124 can have a shape memory tip that automatically assumes a preset shape or configuration when unsheathed by more than a certain amount (e.g., from a sheath 126, such as described below). For example, the energy delivery element 124 can have a shape memory tip that automatically curves or assumes a curved shape or atraumatic configuration (e.g., when curved, a curved portion becomes the most distal portion of the energy delivery element 124 thus making it less sharp and likely to damage off-target tissue). Alternately or additionally, the guidewire can include a spring-tempered stainless steel portion that can return to a predetermined shape, when released from a constraining sheath (such as the dilator discussed below). In some embodiments, the energy delivery element 124 can include a coiled structure that is at least partially coated, e.g., with an insulating layer. In some embodiments, the energy delivery element 124 can be formed of metallic and polymer materials. In some embodiments, the energy delivery element 124 can include more than one coiled structures. For example, a coated coiled structure and an uncoated coiled structure. In some embodiments, the energy delivery element 124 can include an insulating coating near the tip. In some embodiments, the energy delivery element 124 can include material near the distal tip that provides radiopacity. echogenicity, and/or insulation (e.g., tantalum, tungsten, etc.).

In some embodiments, the energy delivery element 124 can have a large active electrode region, e.g., greater than about 1 cm, greater than 2 cm, greater than 3 cm, greater than 4 cm, greater than 5 cm, or greater than 10 cm, or between about 1 cm and about 20 cm, including all values and sub-ranges therebetween. The active electrode region can include the distal conductive tip of the energy delivery element 124 and a conductive outer portion of the energy delivery element 124, e.g., a conductive outer coil, plating, etc. The larger active electrode region can provide cooling to the tip, as the conductive/uninsulated region of the guidewire can wick or conduct away heat. The larger active electrode region can also reduce current density at a distal tip of the energy delivery device 124, thereby reducing the risk of forming lesions.

In some embodiments, the energy delivery element 124 can include at least one sensor. The at least one sensor can be located in the tip of the guidewire, near the tip of the guide, in a distal portion, in a proximal portion, and/or the like. As used herein, proximal refers to the portion of a device or component closest to the surgeon and distal refers to portions closer to the patient anatomy. The sensor can be configured to measure a characteristic of the guidewire. For example, the sensor can be configured to measure temperature, current density, pressure, and/or the like. In some embodiments, the sensor can be used for locating the tip in an electroanatomic mapping system allowing the guidewire to be located in a cardiac space. In some embodiments, the sensor can be a temperature sensor such as a thermistor or thermocouple. In some embodiments, the sensor can be a bi-metal thermocouple, e.g., where there is a weld between an outer coil wire and one or more core wires. The proximal joint of the coil and core wire(s) can serve as a bi-metal thermocouple. In some embodiments, the sensor can be a thermistor that is integrated into a coil of the guidewire. The sensor can be used to provide feedback to decrease or switch off power in response to an out-of-range reading, thus improving the safety of the procedure.

In some embodiments, the energy delivery element 124 can have a proximal length or portion that is coated with an insulator and a distal length or portion that is not. The coated portion can be grasped or manipulated by an operator (e.g., surgeon) during an electrosurgical procedure. In some embodiments, the energy delivery element 124 can be formed of materials that allow a surgeon to quickly identify or recognize the energy delivery element 124. For example, the energy delivery element 124 can have a two-tone design that includes a metallic distal colored portion and a non-conductive proximal colored portion. The metallic portion can extend toward a set point along the energy delivery element 124 (e.g., a midpoint), and acts as a contiguous conductor from the set point to the distal end of the guidewire. The metallic portion can include a metallic coating or other conductive material that covers manufacturing artifacts from welding, heat setting, or shaping, resulting in a consistent, smooth surface finish. In some embodiments, the metallic portion can include plated gold over stainless steel or another base material (e.g., tungsten). The proximal portion can have a polymer coating or other insulating material that insulates the energy delivery element 124. The polymer can be extruded, reflowed, or applied by coating. Suitable examples of such insulative materials include polytetrafluoroethylene (PTFE), polyimide, and nylon. The metallic portion and the proximal non-conductive portion can have the same or different lengths. Further details of example electrosurgical guidewires are described below with reference to FIGS. 8A-9B, 16, 17, 28A-29, 31A-34, and 40-42C.

When used with the electrosurgical interface 122, the conductive portion of the energy delivery element 124 can be coupled to the electrosurgical interface 122 such that energy can be transferred via a conductive core of the energy delivery element 124 to the distal tip of the energy delivery element 124. In some embodiments, the energy delivery element 124 can include stainless steel to conduct energy (e.g., stainless steel core, stainless steel outer coil, etc.). In some embodiments, materials such as gold, platinum, and/or other highly conductive materials can be used to form and/or coat portions of the energy delivery element 124 to improve heat transfer and lower the operating temperature of the tip of the energy delivery element 124 during surgical procedures. For example, the energy delivery element 124 can be formed of such materials and/or coated or plated with such materials. Optionally, materials such as tungsten, tantalum, and/or the like can be incorporated into the energy delivery element 124 for their radiopacity. In an embodiment, the energy delivery element 124 is a conductive metallic wire can have a coiled design with a large surface area and is plated with a good thermal conductor such as gold, to improve heat transfer and lower the operating temperature of the tip. This in turn can reduce the risk of char or thrombus formation due to excessive temperatures.

A sheath 126 (e.g., insulating shaft) can be used together with a guidewire or other energy delivery element 124. The sheath 126 comprises a cannula with a lumen having an inner diameter sized to receive the energy delivery element 124 and allow for sliding of the energy delivery element 124 along the axis of the sheath. The sheath 126 can provide support to the guidewire during advancement of the guidewire through patient anatomy. In some embodiments, the sheath 126 can be configured to constrain or shape the energy delivery element 124. For example, as described above, in some embodiments, the energy delivery element 124 can have a distal tip that is configured to transition between a curved configuration and a straightened or straight configuration. The energy delivery element 124 tip can be formed of shape memory or spring-biased material and that is straight when constrained and curved when not constrained by an outer sheath (e.g., sheath 126). This can be desirable as the guidewire then has an atraumatic shape that can avoid accidental injury to nearby patient anatomy. The sheath 126 can then be used to constrain the energy delivery element 124 to a straight configuration, such that the tip of the energy delivery element 124 can contact and perforate through a tissue structure as it is advanced a first distance distally along the length of the sheath but curves as it is advanced to further distances where it would be more likely to encounter off-target anatomy. Further details of such are described with reference to FIGS. 8A-8C and 42A-42C. In some embodiments, the sheath 126 can include or be used with a dilator. After the energy delivery element 124 forms the perforation or opening in the tissue structure, the dilator can be advanced to dilate the opening, e.g., to facilitate delivery of secondary therapeutic devices such as an ablation catheter, sheath, or other medical device. In some embodiments, the electrosurgical system 100 includes a dilator without a sheath.

The energy delivery element 124 can be designed to have universal compatibility with multiple types of sheaths, dilators, and/or other devices. In some embodiments, the energy delivery element 124 can be used with multiple types of sheaths 126. As such, a surgeon or medical practitioner can select an appropriate sheath to use during a particular operation, without requiring any specific adaptation of the system for use with the selected sheath.

In some embodiments, the guidewire or other energy delivery element 124 can include an insulating collar, disposed near a distal end of the energy delivery element 124. The insulating collar can have a length of between about 2 mm and about 10 mm, including all sub-ranges and values therebetween. The insulating collar surrounds a conductive portion of the energy delivery element 124 near the distal end. In some embodiments, the collar can be disposed between about 0.5 mm to about 3 mm from the distal end of the energy delivery element 124, including all sub-ranges and values therebetween. In operation, as the energy delivery element 124 is extended distally out of the sheath, the conductive tip of the guidewire is exposed. Further extension of the energy delivery element 124 out of the sheath would then expose the insulating collar of the energy delivery element 124. The insulating collar can act as an extension of the insulative sheath such that the total surface area of the exposed conductive portion of the energy delivery element 124 remains small, thereby maintaining higher current density levels near the distal tip of the energy delivery element 124. This ensures that the distal tip of the energy delivery element 124 has sufficient energy to penetrate through the septum, when the energy delivery element 124 is extended a short distance out of the sheath. As the guidewire is extended even further out from the sheath and is inserted into the blood pool beyond the septum (e.g., the left atrium), additional conductive portions of the energy delivery element 124 then become exposed, thereby reducing the current density at the distal tip of the energy delivery element 124. This then reduces the risk that the energy delivery element 124, when disposed beyond the septum, may contact and inadvertently form lesions in the heart wall (e.g., myocardium). Further details of the properties and operation of the guidewire with an insulating collar are described with reference to FIGS. 28A-42C.

Figure 2:
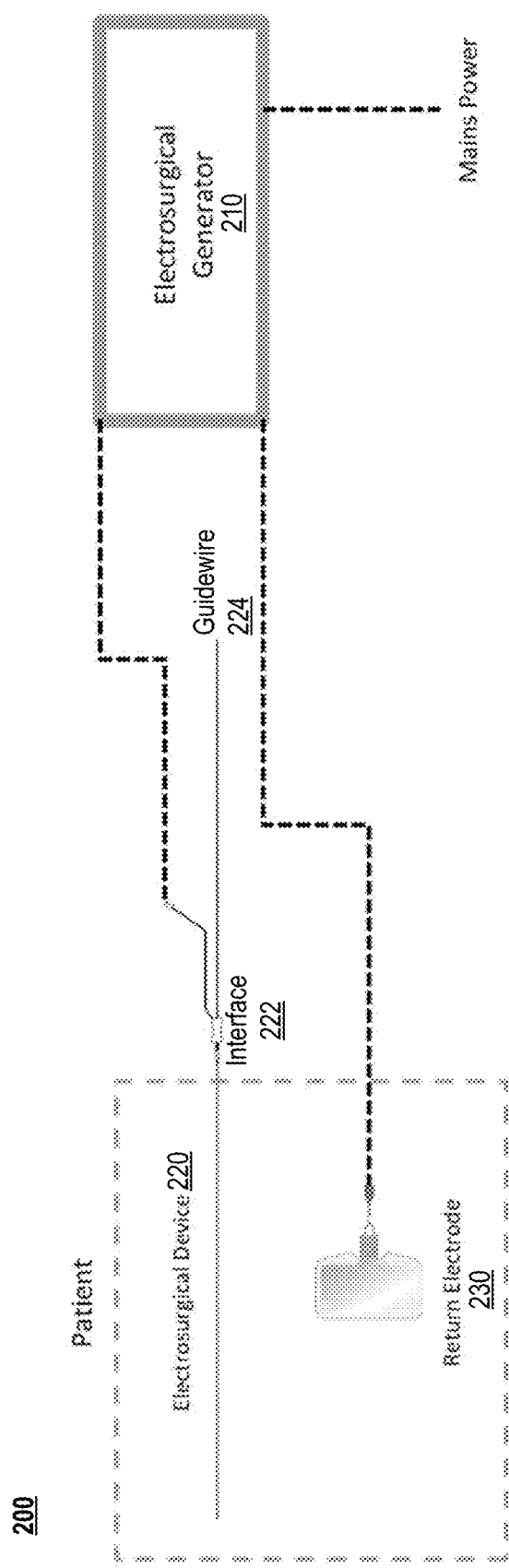
FIG. 2 is a schematic diagram of an electrosurgical system, showing components positioned relative to a patient, according to embodiments.

FIG. 2 is a schematic diagram of an electrosurgical system 200, according to embodiments. The electrosurgical system 200 can be structurally and/or functionally similar to other electrosurgical systems described herein, including, for example, electrosurgical system 100. For example, the electrosurgical system 200 can include an electrosurgical device 220 (e.g., structurally and/or functionally similar to electrosurgical device 120), an electrosurgical generator 210 (e.g., structurally and/or functionally similar to generator 110), and a return electrode 230 (e.g., structurally and/or functionally similar to return electrode 130).

Similar to the electrosurgical system 100, the electrosurgical system 200 can be configured to puncture and cross thin tissue structures for biomedical applications. The system 200 includes the generator 210, an interface 222 with an electrical contact affixed to the fluid lumen of an intravascular sheath or a dilator, a removable guidewire 224 (e.g., an example of an energy delivery element 124) that delivers electrosurgical energy to a therapeutic target (e.g., a tissue structure within the patient), and the return electrode 230 attached to the body of the patient.

In use, the electrosurgical energy flows from the generator 210, into the patient and to the exposed tip of the guidewire 224 that is in contact with the target tissue. The circuit is completed by the return electrode 230 attached to the body of the patient, which may be located on the torso or extremity such as the patient's leg. In some embodiments, the electrosurgical generator 210 connected to the electrosurgical device 220 can generate an oscillating sinusoidal RF waveform having a frequency of approximately 450 kHz and a peak voltage of approximately 200 V. In some embodiments, the generator 210 can operate in constant power mode with a setting of between about 5 W to about 25 W.

In some embodiments, similar to the generator 110, the generator 210 can implement a feedback loop control scheme, whereby the generator 210 adjusts one or more parameters of the RF waveform based on a measured impedance or other characteristic of the circuit. The generator 210 can include circuitry for monitoring the electrical impedance of the circuit going from the generator 210 to the electrosurgical device 220 and to the return electrode 230 and back to the generator 210. The generator 210 (e.g., via an onboard processor or circuitry) can calculate the instantaneous power as provided by the equation P=I*V, where P is power, I is current, and V is voltage. The generator 210 can be programmed to have a predetermined peak voltage ($V_{peak}$) and a peak power ($P_{peak}$), and during electrosurgery, the peak voltage of the voltage waveform can be set to $V_{peak}$ unless the calculated instantaneous impedance value is exceeded, in which case V is reduced so that the power remain below or equal to $P_{max}$.

Electrosurgical Interface

In some embodiments, electrosurgical interfaces as described herein can include a sliding contact design. More specifically, the electrosurgical interfaces can establish electrical couplings between a generator and a guidewire, while allow the guidewire to slide or move within the interface. In existing sliding contact interfaces, the electrical coupling can be established via a physically contacting conductor that engages with a second contact such as a metallic wire or plate. This can result in drag and potential abrasion of the second contact, if the two were moved with respect to one another. For an electrosurgical guidewire, the contacting or interacting portion may contain thin coatings that are subject to wear and eventual particulate generation. For intravascular applications, such particulate generation can lead to patient injury and other complications. For an electrosurgical guidewire, the friction between the contacting portion and the second contact can also result in reduced tactile response or feel of the catheter, resulting in the inability to engage therapeutic targets that are distal to the contacting portion of the guidewire. To address these drawbacks, a spring-loaded electrical contact (e.g., electrosurgical interface) that clips to the proximal end of an electrosurgical guidewire may be used. But such requires a physical clip or clamp to transmit electrosurgical energy from the generator, which limits the degree of movement of the electrosurgical guidewire.

Figure 4:
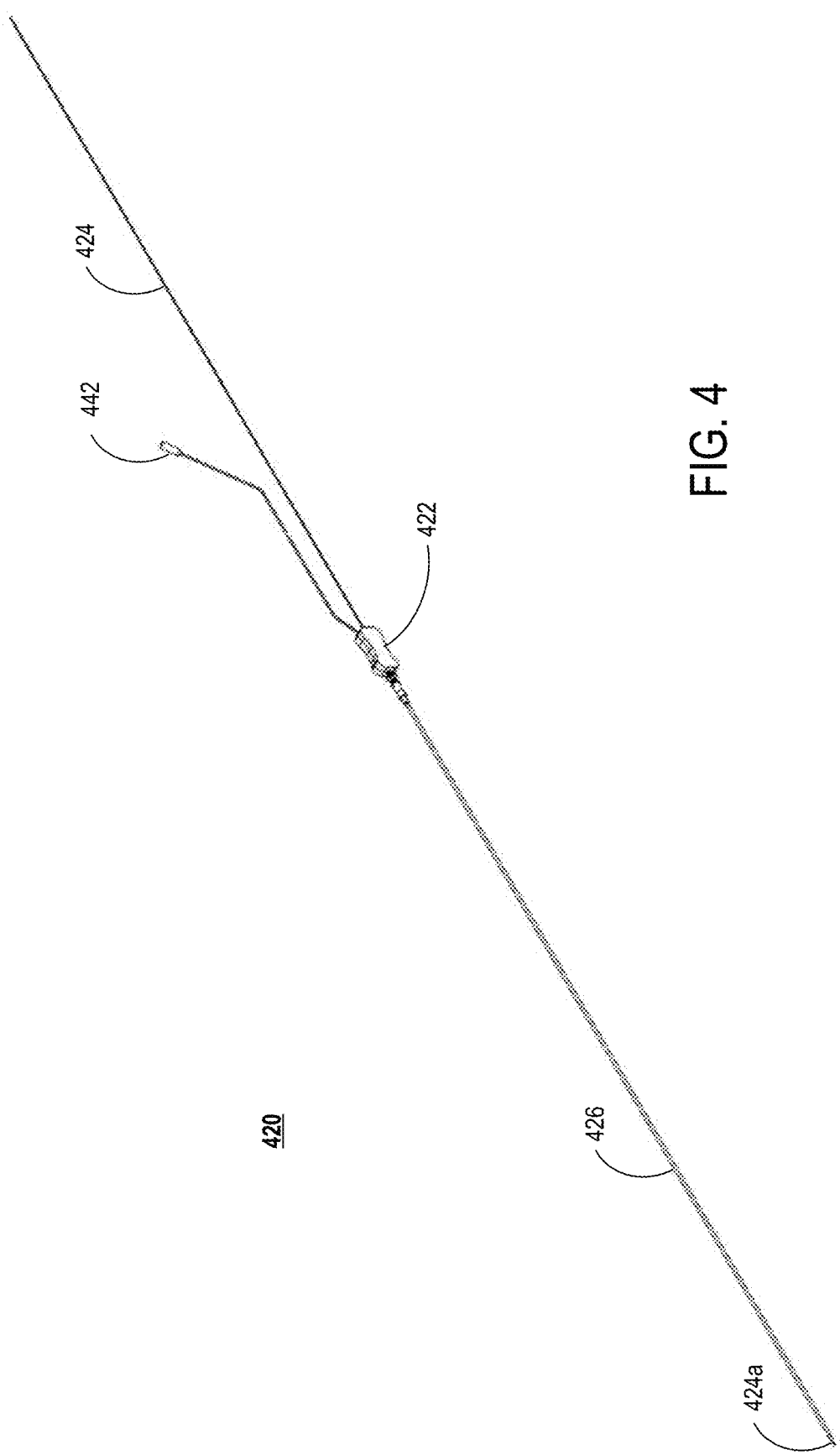
FIG. 4 depicts an example of an electrosurgical device, according to embodiments.
Figure 5A:
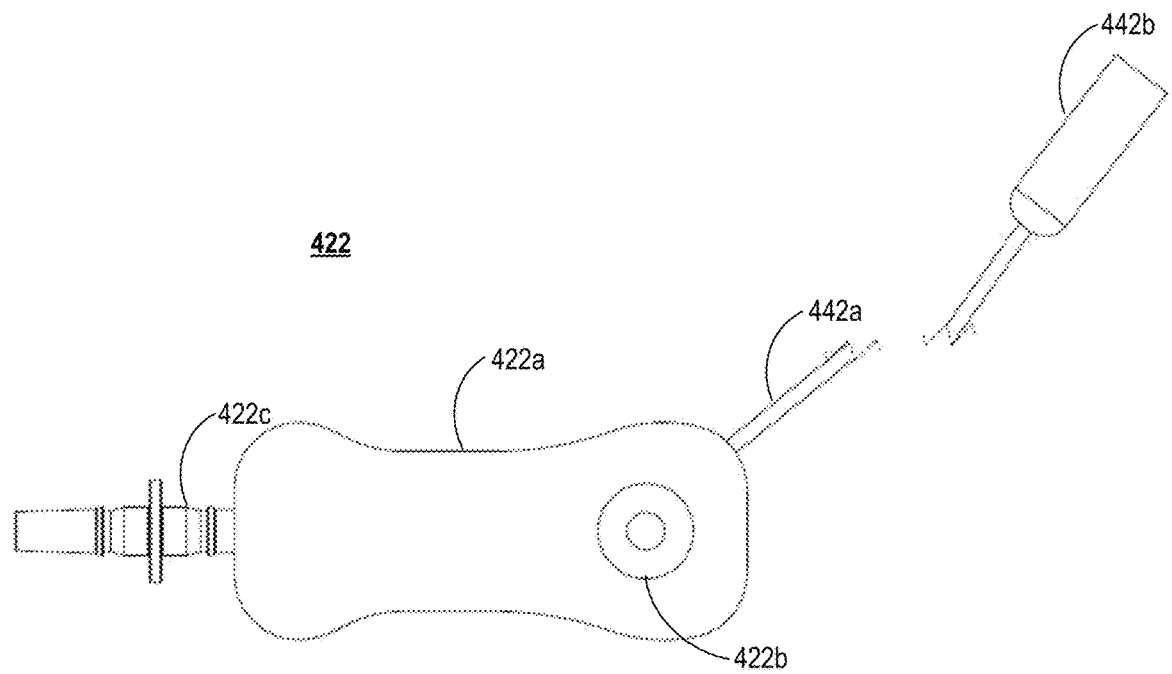
FIG. 5A provides a top view of an electrosurgical interface of an electrosurgical device of FIG. 4.
Figure 5B:
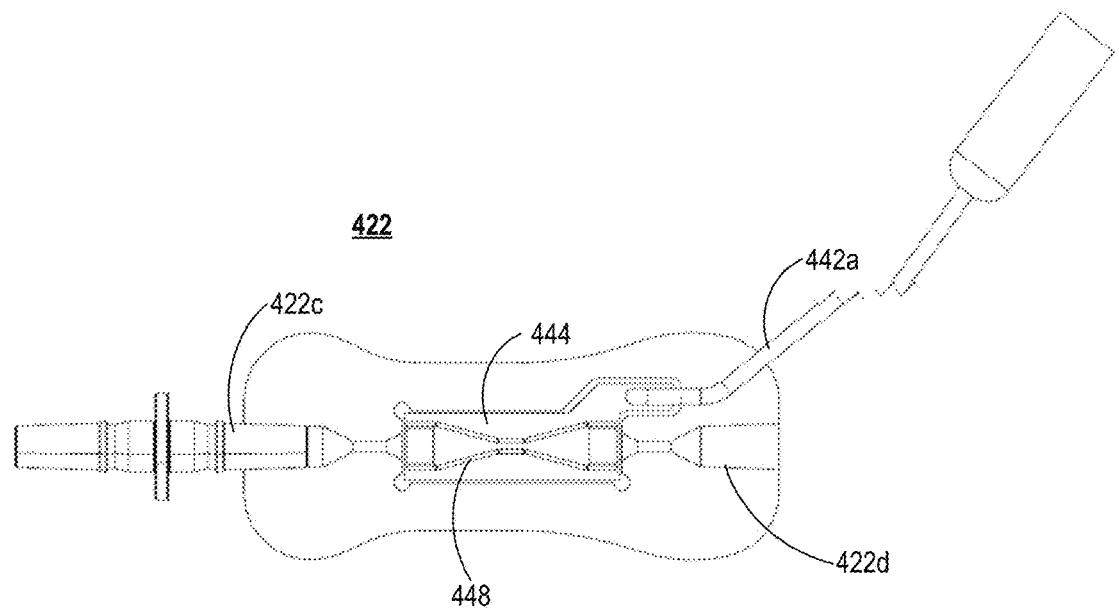
FIG. 5B provides a cross-sectional view of the electrosurgical interface with a portion of the exterior housing being removed to show the interior components of the electrosurgical interface.
Figure 5C:
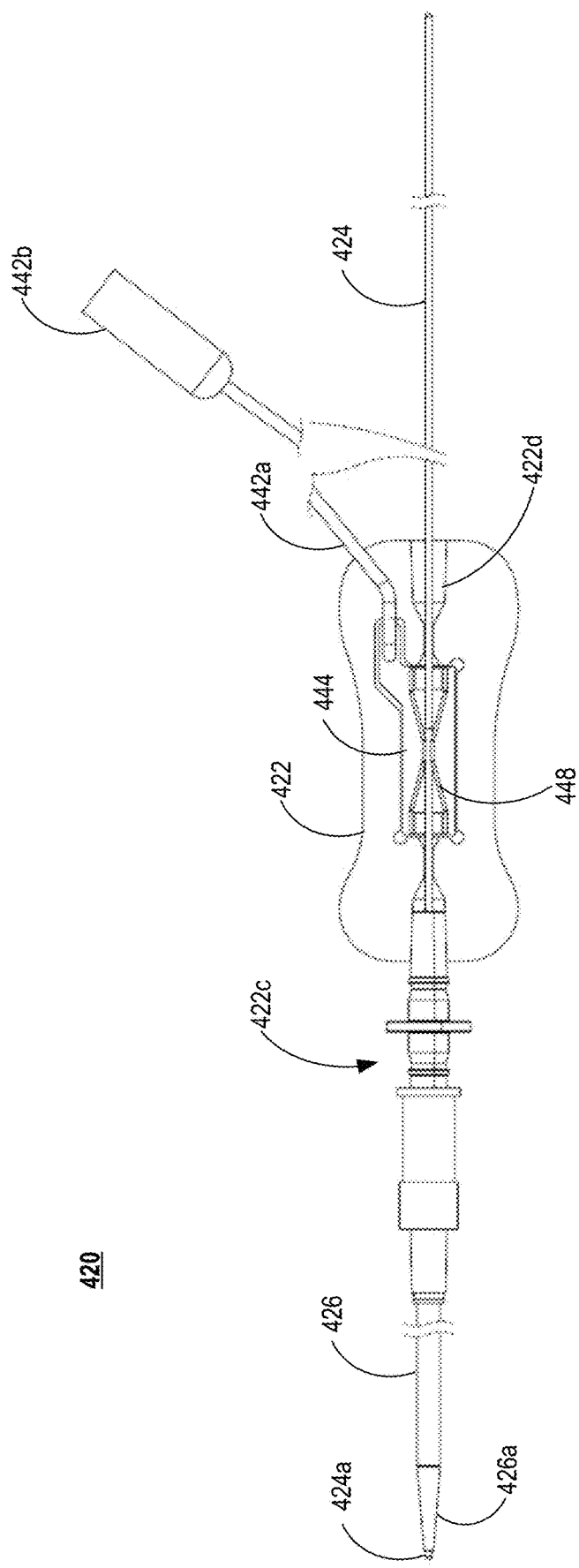
FIG. 5C depicts a side cross-sectional view of the electrosurgical device of FIG. 4, with the interior components of the electrosurgical interface shown.

Electrosurgical devices described herein can provide electrical coupling without direct or physical contact and/or clamps or springs, which are associated with the drawbacks described above. FIGS. 4-5C depict an electrosurgical device 420, according an embodiment. FIG. 4 provides a perspective view of the electrosurgical device 420. FIGS. 5A and 5B depict detailed views of an electrosurgical interface 422 of the electrosurgical device 420. FIG. 5C depicts a side view of the electrosurgical device 420, with break points to better show details of the various components of the electrosurgical device 420. The electrosurgical device 420 may be functionally and/or structurally similar to the electrosurgical device 120 of FIG. 1.

As depicted in FIG. 4, the electrosurgical device 420 includes the electrosurgical interface 422 (e.g., functionally and/or structurally similar to the electrosurgical interface 122 of FIG. 1), a cable 442, a guidewire 424 (e.g., functionally and/or structurally similar to the energy delivery element 124 of FIG. 1), and a dilator 426 (e.g., functionally and/or structurally similar to sheaths and other dilators described herein).

The electrosurgical interface 422 is electrically coupled to the cable 442, which may electrically couple to a generator, such as the generator 110 of FIG. 1. The electrosurgical interface 422 establishes electrical connectivity between the generator and conductive portion of the guidewire 424. As described in reference to FIG. 1, the electrosurgical interface 422 may include a button or actuation device for switchably or selectively establishing the electrical connection between the generator and the guidewire 424. The electrosurgical interface includes a housing that is electrically insulated from current-carrying components of the electrosurgical interface 422, allowing for the electrosurgical interface 422 to be safely and comfortably handled. In some embodiments, the housing is formed of plastic. In some embodiments, the housing is approximately 1-2 inches long, including all values and sub-ranges therebetween.

The electrosurgical interface 422 is configured to establish and maintain electric connectivity with the guidewire 424 even as the guidewire 424 is moves or translates within the electrosurgical interface 422. The electrosurgical interface 422 includes a fixed electrode connected to the output of the generator via the cable 442. When the guidewire 424 is inserted into a lumen of the electrosurgical interface 422, the fixed electrode contacts a conductive portion of the guidewire 424 and may be provide an electrical connection to the generator via cable 442. The structure of the electrosurgical interface 422 is further described in greater detail in reference to FIGS. 3A-3B.

The guidewire 424 includes a tip 424a, located at the distal end of the guidewire 424. The tip 424a of the guidewire 424a is configured to apply energy to a tissue structure. The guidewire 424 can extend through the electrosurgical interface 422, where an electrode or other conductive element of the electrosurgical interface 422 electrically couples to a conductive portion of the guidewire 424 to provide power to the guidewire 424 from the generator. The portion of the guidewire 424 that may be in contact with the electrosurgical interface 422 can be conductive, while portions of the guidewire 424 that do not contact the electrosurgical interface 422 may be insulated or otherwise non-conductive. The guidewire 424 is further described in reference to FIGS. 8A-9B.

When so deployed, the guidewire 424 includes a portion that extends through the electrosurgical interface 422 and a portion disposed in a lumen of the dilator 426. Optionally, the tip 424a of the guidewire 424 can be configured to have a curved or J-shape when unconstrained, e.g., disposed outside of the dilator 426, which may have sufficient stiffness to constrain the curved tip 424a. In use, the guidewire 424 can be navigated through patient vasculature, e.g., in its unconstrained configuration. The electrosurgical interface 422 and dilator 426 can be loaded onto the guidewire 424 and the dilator 426 can be advanced through the patient anatomy (e.g., vasculature and into the heart). The dilator 426 can insulate any conductive portions of the guidewire 424 that are disposed within the dilator 426 to protect the patient from an undesired energy delivery. The tip 424a of the guidewire 424 advanced until it is positioned distal to the distal end of the dilator 426. The dilator 426 is configured to constrain the guidewire 424 in a straightened configuration when the tip 424a of the guidewire 424 is substantially disposed within the dilator 426, as depicted in FIG. 4. As such, the dilator 426 can have a stiffness sufficient to keep the tip 424a of the guidewire 424 straight while within the dilator 426. In use, the tip 424a can remain relatively straight when advanced a first distance beyond the sheath and curve when advanced to greater distances. The straightened configuration of the guidewire 424 can correspond to a position for delivering energy via the tip 424a of the guidewire 424, as further described with reference to FIG. 8B below.

In an embodiment, the dilator 426 is coupled to the electrosurgical interface 422, such that the dilator 426 moves in tandem with the electrosurgical interface 422. For example, the dilator 426 can be coupled to the electrosurgical interface 422 via a Luer connection or similar partial-turn connector, though other types of connectors are known in the art. Because the dilator 426 is coupled to the electrosurgical interface 422, a user can advance the dilator 426 and set its position by pushing or moving the electrosurgical interface 422. In some embodiments, finer movement and/or control of the dilator 426 can also be possible, e.g., by manipulating an actuator (e.g., knob, slider, etc.) that can extend or retract the dilator 426 relative to the electrosurgical interface 422. In some embodiments, the dilator 426 may be used to dilate the opening created by the guidewire 424 delivering energy to a target location.

In the embodiment depicted in FIG. 5A, the electrosurgical interface 422 includes a housing 422a, a button 422b, a dilator interface 422c (e.g., coupler), and a cable portion 442a terminating in a cable plug 442b. The housing 422a houses internal components of the electrosurgical interface 422 and insulates and protects an operator and patient from electrical components of the electrosurgical interface 422a. In some embodiments, the housing 422a is formed of an insulating material such as plastic, rubber, or the like. The housing 422a may have an ergonomic shape to ease handling; for example, a narrow central portion to make it easy to firmly grip. The button 422b is disposed on the housing 422a. When actuated, the button 422b allows for the guidewire 424 to receive energy, e.g., from a generator 110 coupled to the electrosurgical interface 422. In some embodiments, the button 422b may be coupled to a processor or other device that is configured to control the delivery of energy to the guidewire 424. For example, when the button 422b is actuated, a signal can be sent to the processor, which can then control the electrosurgical interface 422 to provide energy to the guidewire 424 for a predetermined amount of time. In some embodiments, energy is provided to the guidewire 424 when the button 422b is pressed. Optionally, the circuit is then broken when the button is then released (e.g., such as with a spring-loaded button or slider). In such embodiments, depressing the button 422b may establish an electrical connection between the electrosurgical interface 422 and the guidewire 424 and/or the generator, such that a closed circuit can be formed between these various electrical components in conjunction with return electrode 130. In some embodiments, the button 422b is a toggle switch, e.g., for toggling on and off energy delivery to the guidewire 424. In such embodiments, a processor can be configured to control the toggling and/or the depression of the button can mechanically close a switch that then connects the generator power supply to the guidewire 424.

The dilator interface 422c allows for the dilator 426 to be selectively coupled to the electrosurgical interface 422. In some embodiments, the dilator interface 422c includes a locking mechanism to prevent the dilator 426 from decoupling from the electrosurgical interface 422. The dilator interface 422c further allows a continuous lumen to be established for receiving the guidewire 424, such that, during a surgical procedure, the dilator 426 can be advanced over the guidewire with the electrosurgical interface 422. The electrosurgical interface 422 receives energy via the cable 442, which includes a cable portion 442a and a cable plug 442b. The cable portion 442a directs energy into the electrosurgical interface 422 while the cable plug 442b interfaces with the generator.

As seen in the embodiment depicted in FIG. 5B, the cable portion 442a electrically couples to a conductive path 444. The conductive path 444 carries energy from the cable 442 to an electrode 448. In some embodiments, a hourglass structure can be disposed near the electrode 448 and define at least a portion of the lumen for receiving the guidewire 424. The electrode 448 allows the guidewire 424 to slide within the guidewire lumen while maintaining constant electrical coupling between the electrode interface 422 and the guidewire 424. In some embodiments, the electrical coupling between the electrode interface 422 and the guidewire is established via a conductive fluid, similar to that described with reference to FIG. 3 above. For example, a conductive fluid can fill a space (e.g., chamber) around the guidewire 424 and the electrode 448 to provide lubrication/reduce friction and establish electrical conductivity. In some embodiments, the electrode electrically couples to the guidewire via a spring. The spring can impart a pressure on the electrode so that a constant electrical coupling is maintained while allowing the guidewire to translate relative to the spring.

In some embodiments, the electrosurgical interface 422 can include an additional port 422d. The port 422d can be configured to couple one or more other devices, e.g., to flush the chamber or guidewire lumen with a fluid, etc. In some embodiments, the port 422d can also be configured to receive the guidewire 424.

FIG. 5C depicts the guidewire 424 extending through the electrosurgical interface 422 and the dilator 426. The guidewire 424 extends through the interface 422d, contacts the electrode 448, and extends through the dilator interface 422c and the dilator 426. In the configuration of FIG. 5C, the guidewire 424 is shown retracted within the dilator 426. As discussed above, during operation, the tip 424a of the guidewire 424 may be extended and disposed distal to the distal end of the dilator 426 such that the guidewire 424 can optionally form a J-shape (or other atraumatic shape).

Figure 6A:
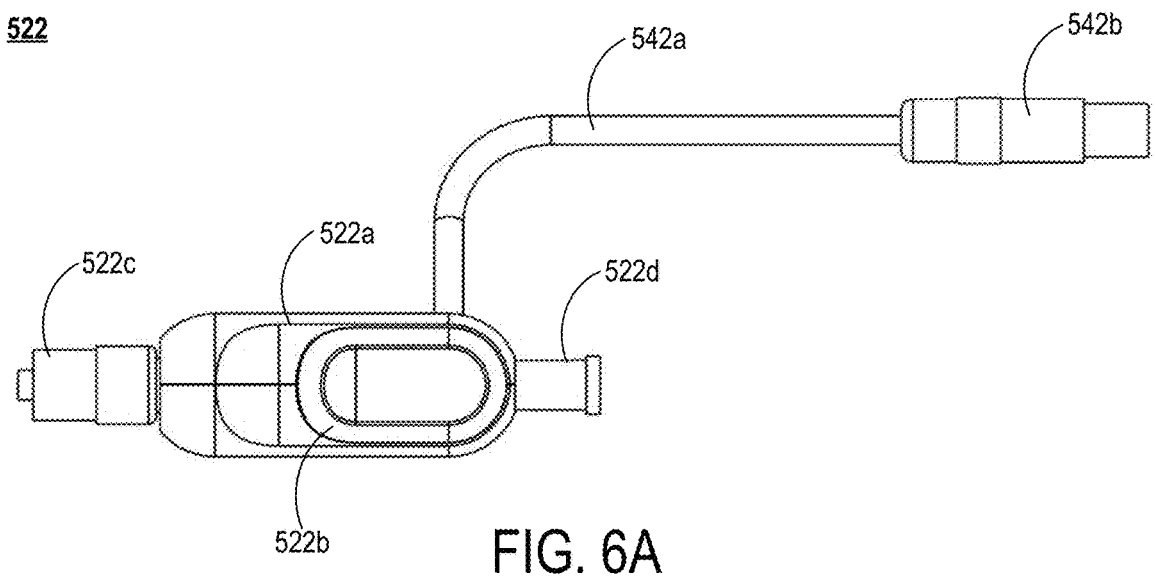
FIG. 6A depicts a top view of another example of an electrosurgical interface of an electrosurgical device, according to embodiments.
Figure 6B:
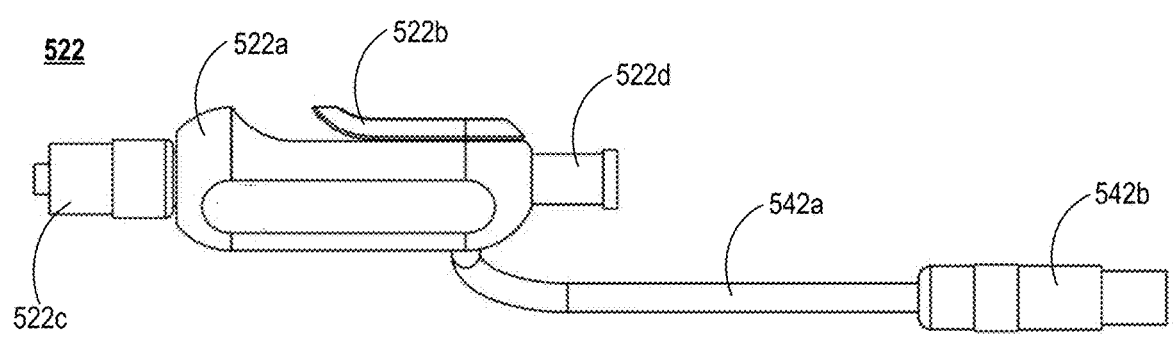
FIG. 6B depicts a side view of the electrosurgical interface of FIG. 6A.
Figure 6C:
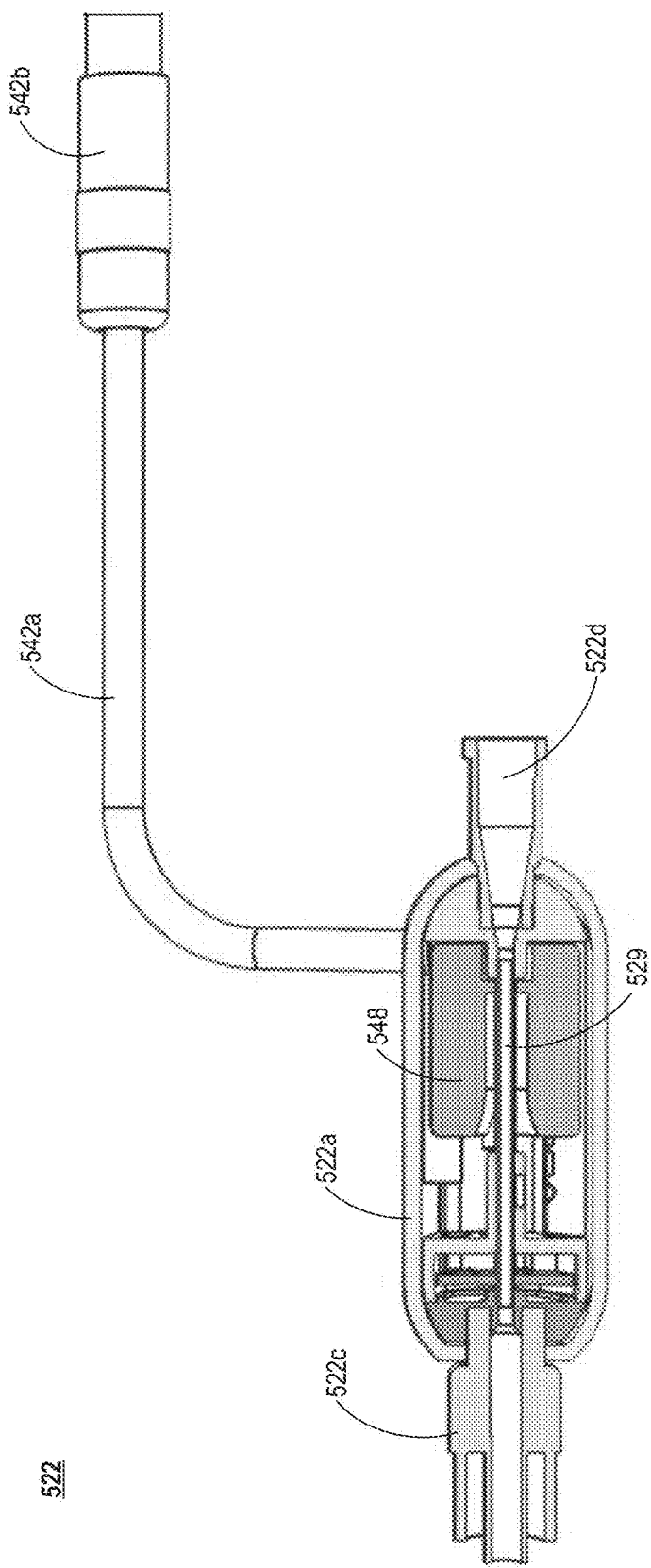
FIG. 6C depicts a top view of the electrosurgical interface of FIG. 6A, with the interior components of the electrosurgical interface shown.

FIGS. 6A-6C depict an electrosurgical interface 522 (e.g., functionally and/or structurally similar to the electrosurgical interface 122 of FIG. 1 and/or the electrosurgical interface 422 of FIGS. 4-5C), according to embodiments. FIG. 6A depicts a top view of the electrosurgical interface 522. FIG. 6B depicts a side view of the electrosurgical interface 522. FIG. 6C depicts a top view of the electrosurgical interface 522, with the interior components of the electrosurgical interface shown.

Similar to the electrosurgical interface 422, the electrosurgical interface 522 is configured to establish electric connectivity with a guidewire (e.g., functionally and/or structurally similar to the energy delivery element 124 of FIG. 1), and to maintain that connection while the guidewire moves or translates within the electrosurgical interface 522. The electrosurgical interface 522 includes a housing 522a (e.g., functionally and/or structurally similar to the housing 422a of FIGS. 5A-5C), an actuator 522b (e.g., functionally and/or structurally similar to the button 422b of FIGS. 5A-5C), a dilator interface or coupler 522c (e.g., functionally and/or structurally similar to the coupler 422c of FIGS. 5A-5C), a cable portion 542a (e.g., functionally and/or structurally similar to the cable portion 442a of FIGS. 5A-5C), a cable plug 542b (e.g., functionally and/or structurally similar to the cable plug 442b of FIGS. 5A-5C), and an additional port 522d (e.g., functionally and/or structurally similar to the additional port 522d of FIGS. 5B-5C).

The actuator 522b of the electrosurgical interface 522 is a sliding actuator that, in operation, is translated from a first position (e.g., inactive position) to a second position (e.g., active position). In some embodiments, the first position can be a more proximal position, and the second position can be a more distal position. While the actuator 522b is a sliding actuator, the actuator 522b can function similar to the button 422b described above with reference to FIGS. 5A-5C. For example, in the distal or active position, the actuator 522b can cause electrical energy to be delivered to a guidewire disposed within the electrosurgical interface 522. In some embodiments, the actuator 522b can generate a signal that triggers an electrosurgical generator (e.g., generator 110) to deliver energy (e.g., a voltage waveform) to the electrosurgical interface, which in turn delivers the energy to the guidewire. In some embodiments, the actuator 522b may provide a user with haptic feedback (e.g., vibration, click, etc.) during operation, e.g., when the actuator 522b is moved a position that causes energy to be delivered to the guidewire. In some embodiments, the actuator 522b may not be a sliding actuator. For example, the actuator 522b can be a button that can be pressed to activate energy delivery, or another type of actuated component. In some embodiments, operating the actuator 522b may include multiple motions. For example, to activate energy delivery to the guidewire, the actuator 522b may need to be first translated and then pressed to active energy delivery. In some embodiments, the actuator 522b is spring-loaded so that the actuator 522b returns to the inactive position when the user is not applying a force on the actuator 522b.

The housing 522a can be configured to be grasped by a user (e.g., a surgeon) during use. The surgeon, for example, can hold the housing 522a using one hand, while using his or her other hand to hold and move (e.g., distally advance and/or retract) the guidewire disposed within the electrosurgical interface. As depicted in FIGS. 6A-6B, in some embodiments, the cable portion 542a can be located along the housing at a location that does not does not interfere with the user when holding the housing 522a. For example, as seen in FIG. 6B, the cable portion 542a may be located toward a back of the housing 522a, and can extend at an angle away from the housing 522a. Similar to the cable 442a, the cable 522a can include a plug or connector 542b that can plug into or otherwise couple to a generator (e.g., generator 110) for receiving energy from the generator and for sending signals to the generator (e.g., for triggering energy delivery). In some embodiments, the location of the cable portion 542a can be reconfigurable to allow for a first configuration for a left-handed user and a second configuration for a right-handed user.

As seen in FIG. 6C, the inner components and arrangement of the electrosurgical interface 522 can be similar to that of the electrosurgical interface 422. For example, the electrosurgical interface 522 includes an electrode 548 (e.g., structurally and/or functionally similar to the electrode 448 of FIG. 5C) that is wired to the generator via the cable components 542a, 542b. The electrode 548 can be electrically coupled to a guidewire disposed within a lumen 529 defined in part by or adjacent to the electrode 548, e.g., via a conductive fluid disposed within the lumen (e.g., similar to that described with respect to FIG. 3). As described in detail in later figures of the guidewire, the guidewire can include a conductive portion that is configured to be disposed within the conductive fluid within the lumen, such that energy delivered by the generator to the electrode can be received via the conductive fluid by the guidewire. The guidewire can have a conductive surface region that is coupled to a conductive core of the guidewire, which can carry the energy to a distal tip of the guidewire, e.g., for perforating through tissue. The guidewire can be received through port 522d and extend through the electrosurgical interface 522. The electrosurgical interface 522 can also include a dilator interface or coupler 522c, which can be coupled to a dilator or sheath (e.g., sheath 126 or dilator 426).

As an alternative embodiment to the sliding contact described with reference to FIGS. 3A-6C, an electrosurgical interface can be configured to couple to a distal end of a guidewire, e.g., via physical attachment between electrical port and the guidewire. In such embodiments, the proximal end of the guidewire can be received within the electrosurgical interface and physically engaged with an electrode or other conductive component that is wired to the generator (e.g., via electrical circuitry). The proximal end of the guidewire may include a conductive region, such that energy (e.g., RF current) can be delivered via the guidewire to its distal end, e.g., for perforating through tissue. The movement of the guidewire relative to the electrosurgical interface may be more limited that in the sliding contact embodiments described above.

Figure 7A:
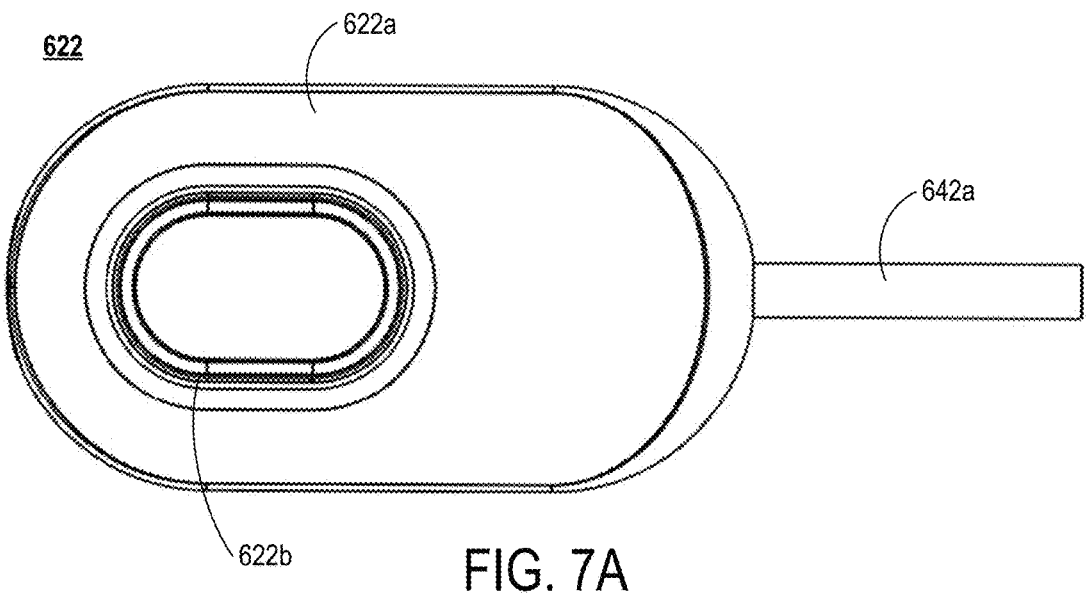
FIG. 7A depicts a top view of another example of an electrosurgical interface of an electrosurgical device, according to embodiments.
Figure 7B:
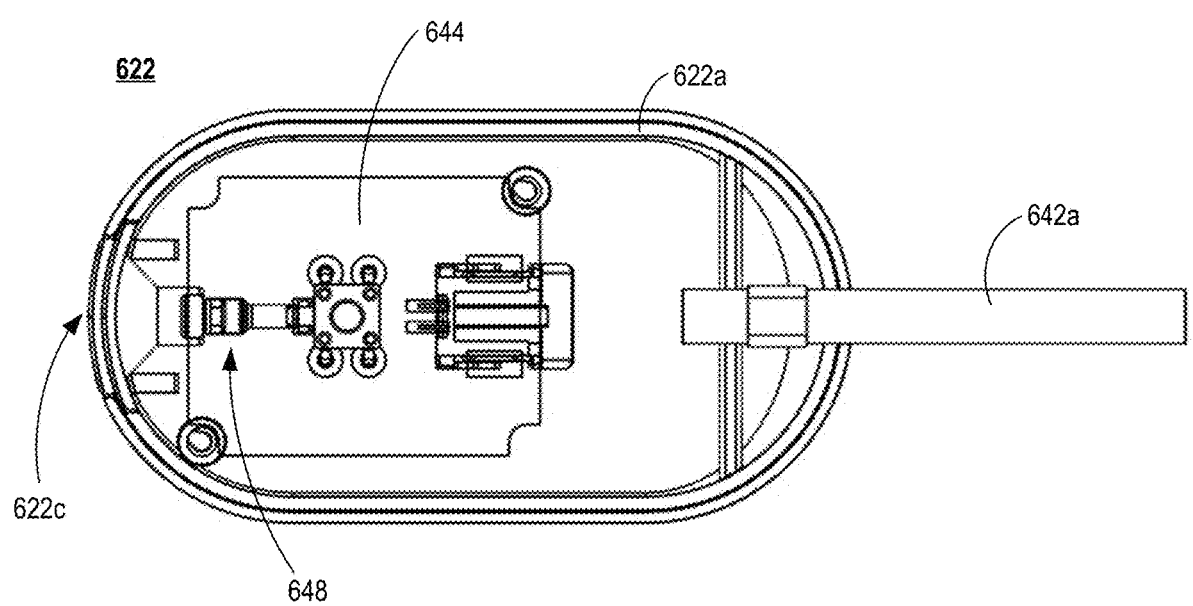
FIG. 7B depicts a top view of the electrosurgical interface of FIG. 7A, with the interior components of the electrosurgical interface shown.
Figure 7C:
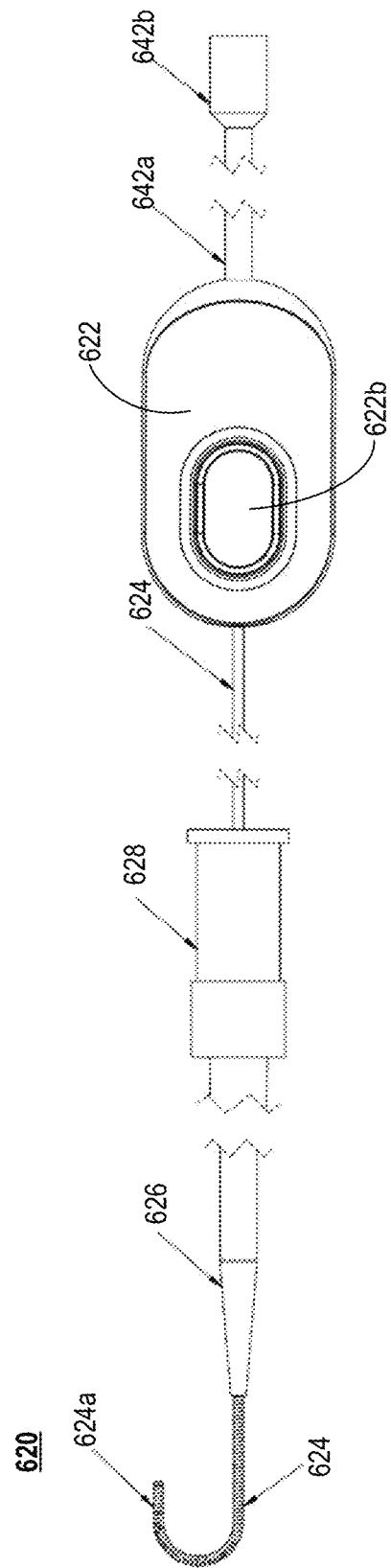
FIG. 7C depicts a top view of the electrosurgical device showing the arrangement of the electrosurgical device, according to embodiments.

FIGS. 7A-7C depict an example of an electrosurgical interface 622, which can be configured to receive a proximal end of a guidewire, e.g., to establish an electrical coupling between the guidewire and a generator (e.g., generator 110), according to embodiments. The electrosurgical interface 622 can include components that are structurally and/or functionally similar to electrosurgical interface 122 of FIG. 1, or other electrosurgical interfaces described herein. FIG. 7A depicts a top view of the electrosurgical interface 622. FIG. 7B depicts a top view of the electrosurgical interface 622, with the interior components of the electrosurgical interface shown. FIG. 7C depicts a top view of an electrosurgical device 620 (e.g., structurally and/or functionally similar to the electrosurgical device 120 of FIG. 1) with the electrosurgical interface 622, according to embodiments.

As seen in FIG. 7A, the electrosurgical interface 622 includes a housing 622a (e.g., functionally and/or structurally similar to the housing 422a of FIGS. 5A-5C), a button 622b (e.g., functionally and/or structurally similar to the button 422b of FIGS. 5A-5C), and a cable 642a (e.g., functionally and/or structurally similar to the cable portion 642a of FIGS. 5A-5C). As seen in FIG. 7B, the electrosurgical interface 622 further includes a port or opening 622c and an electrode 648 disposed on a circuit board 644 that can be electrically coupled to the generator. The cable 642 is operatively coupled to the electrosurgical interface 622a via the circuit 644 to provide electrical energy to the guidewire via the electrode 648.

The port 622c is configured to receive a guidewire (e.g., functionally and/or structurally similar to the energy delivery element 124 of FIG. 1) so that the guidewire can physically engage with the electrode 648. The electrosurgical interface 622 can include a coupling element (e.g., clip, fastener, etc.) that can be configured to hold onto the guidewire, e.g., to maintain the guidewire in place within the port after the guidewire has been received in the port. When the guidewire has been received within the port 622c and coupled to the electrode 648, the electrode 648 can be configured to deliver electrical energy to the guidewire in response to the button 622b being actuated by a user. While a button is depicted in FIGS. 7A-7C, it can be appreciated that any type of actuator can be used to activate the energy delivery. Similar to the slide actuator described with respect to figures above, actuation of the button can be configured to send a signal to the generator to trigger the generator to deliver energy to the guidewire.

FIG. 7C depicts the electrosurgical device 620 including a guidewire 624 (e.g., functionally and/or structurally similar to the energy delivery element 124 of FIG. 1), a dilator or sheath 626 (e.g., functionally and/or structurally similar to the sheath 126 of FIG. 1), a dilator hub 628, and the electrosurgical interface 622. The guidewire 624 can be disposed within the dilator 626 and the hub 628, and movable relative to the dilator 626 and the hub 628. The proximal end of the guidewire 624 can be received in the electrosurgical interface 622. In FIG. 7C, the tip 624a of the guidewire 624 is extended and disposed distal to the distal end of the dilator 626 such that the guidewire 624 forms a J-shape (or other atraumatic shape). In use, the guidewire may initially be disposed within the dilator 626 in a straightened configuration, and then extended distal to the dilator 626 to expose a tip of the guidewire for delivering energy, e.g., to perforate tissue.

Systems and devices described herein avoids the drawbacks of sliding contact designs with physical contact between the two sliding components by using a fluid-filled chamber for establishing electrical connection between the electrosurgical generator and the electrosurgical device. An electrosurgical guidewire can be positioned within the fluid-filled chamber and freely advanced or retracted. With systems and devices described herein, the electrosurgical guidewire can have an unrestrained proximal end, which allows an operator to freely advance, retract, or exchange the guidewire without any intermediate steps, such as, for example, disconnecting the cable. In contrast to systems where the proximal end of the guidewire may be restrained (e.g., clamped or clipped to a connector), a physician can quickly remove a sheath, dilator, or other instrument by retracting it over the guidewire, and exchange it for a different instrument. This can result in improved workflows and potentially faster procedure times. Additionally, a physician or other medical professional can activate energy delivery from within a sterile environment by using the activation mechanism. Moreover, given the frictionless design (or substantially frictionless design) of electrical connection between the generator and the electrosurgical device, a physician can rely on tactile feedback (e.g., as a result of guidewire tip's behavior) to assess when the guidewire is in contact with a tissue surface. In transseptal perforation cases, this tactile feedback can be important to a physician to confirm placement of the guidewire, monitor when perforation has occurred, and/or monitor when inadvertent contact with a tissue surface may be occurring.

Figure 3A:
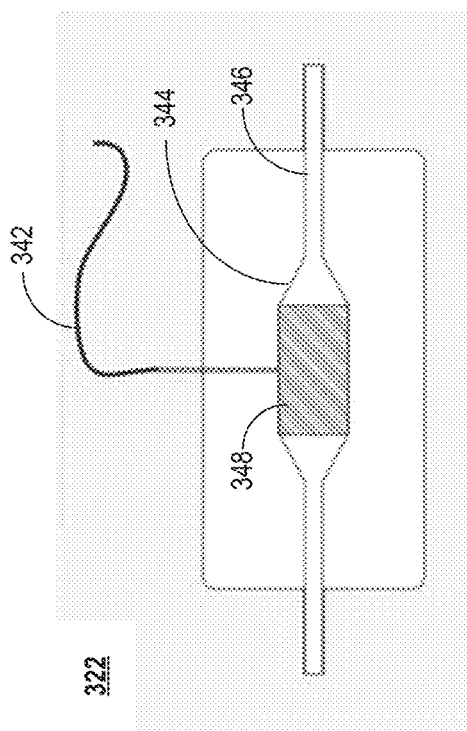
FIGS. 3A-3C schematically depict an interface for transmitting electrical energy from an electrosurgical generator to an energy delivery element, according to embodiments.
Figure 3C:
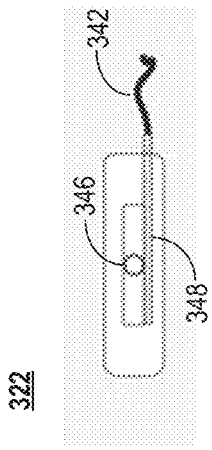
Figure 3B:
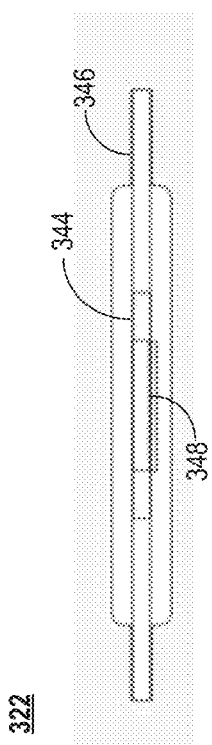

FIGS. 3A-3C depict different views of an example electrosurgical interface 322, according to embodiments. The electrosurgical interface 322 can be configured to transmit electrical energy from an electrosurgical generator (e.g., generator 110, 210) to the distal tip of a conductive guidewire or other energy delivery element (e.g., energy delivery element 120, guidewire 224) for therapeutic purposes such as transseptal puncture. The electrosurgical interface 322 can be structurally and/or functionally similar to other electrosurgical interfaces described herein (e.g., electrosurgical interface 122, 222).

As depicted in FIG. 3A, the electrosurgical interface 322 can include a fluid-filled chamber 344 that transmits electrosurgical energy from a cable 342 connected to the generator (not depicted) to a stationary conductive electrode 348, and to a moveable conductive element (e.g., energy delivery element 120, guidewire 220). The fluid filled chamber 344 can include a thin layer of conductive fluid that conducts the energy from the generator and the stationary electrode 348 to the movable conductive element. Energy can therefore be conducted from the generator to the distal tip of a movable conductive element such as a guidewire.

The chamber 344 can have a shape that is easy to flush and fill with fluid without any residual air bubbles being present within the chamber 344. For example, the chamber 344 can have rounded edges or corners to avoid entrapment of bubbles within the chamber. The conductive fluid that is used can be a saline solution or other conductive solution that is sterile. In an embodiment, the conductive fluid is a 0.9% saline (NaCl) solution. The conductive fluid, combined with a large stationary electrode surface area, can provide an electrosurgical connection that does not increase (or does not significantly increase) the impedance of the circuit or add additional electrical load on the generator.

The stationary electrode 348 may have a flat printed circuit board construction or be a metal plate with gold, silver, steel, or copper conductors. Since the stationary electrode 348 is in contact with the patient blood pool via the fluid path, the stational electrode 348 should also be biocompatible. The stationary electrode 348 can be flat, as depicted in FIGS. 3A-3C, or alternatively, it can have a tubular design where the movable conductive element is coaxial to the stational electrode. For example, with a tubular design, the stationary electrode can be formed of a coiled wire that is coaxial to the movable conductive element.

The movable conductive element (not depicted) can be the energy delivery element or guidewire, e.g., as described above with respect to FIGS. 1 and 2. In some embodiments, the movable conductive element is a metallic guidewire, where a conductive portion of the guidewire is positioned adjacent to the stationary electrode that is surrounded by the conductive fluid. The conductive portion of the guidewire can be a stainless-steel section or be plated with a inert highly conductive alloy (e.g., gold) to facilitate a low impedance path from the electrosurgical generator. In some embodiments, an insulating coating can be located distal of or proximal of the conductive portion of the guidewire that is in the conductive fluid, e.g., to provide for electrical insulation along other portions of the guidewire.

Figure 10:
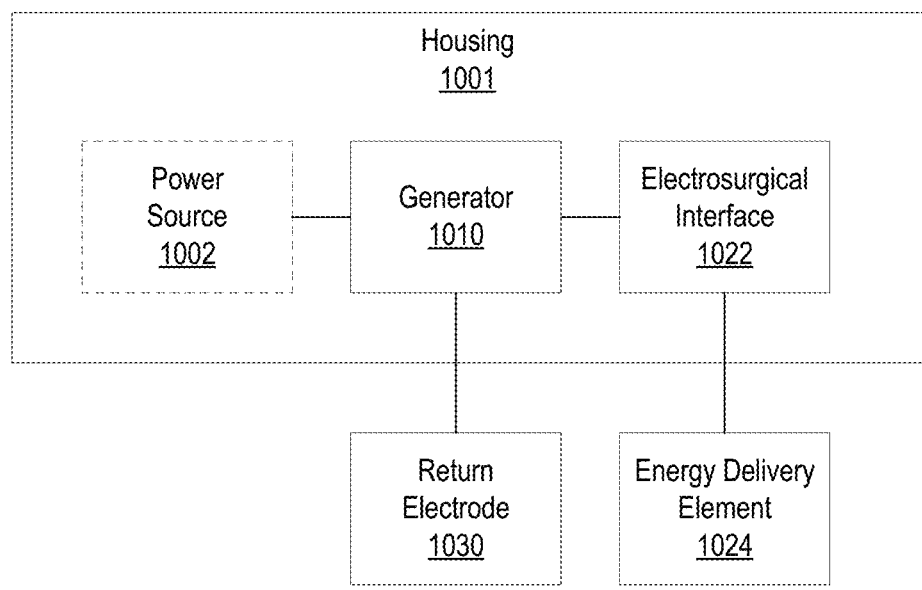
FIG. 10 is a schematic diagram of a handheld electrosurgical system, according to embodiments.

In some embodiments, an electrosurgical generator (e.g., generator 110, 210) can be integrated together with an electrosurgical device (e.g., electrosurgical device 120, 220). In such embodiments, the electrosurgical generator and device may include a handheld component, e.g., a handle assembly, which can house the generator. FIG. 10 is a schematic diagram of a handheld electrosurgical system 1000, according to embodiments. In some embodiments, the handheld electrosurgical system 1000 can include components that are structurally and/or functionally similar to other electrosurgical systems described herein, including, for example, the electrosurgical system 100 of FIG. 1. The handheld electrosurgical system 1000 includes a housing 1001 including, optionally, a power source 1002 (e.g., structurally and/or functionally similar to the power source 102 of FIG. 1), a generator 1010 (e.g., structurally and/or functionally similar to the generator 110 of FIG. 1), and an electrosurgical interface 1022 (e.g., structurally and/or functionally similar to the electrosurgical interface 122 of FIG. 1). The handheld electrosurgical system 1000 further includes a return electrode 1130 (e.g., structurally and/or functionally similar to the return electrode 130 of FIG. 1) operatively coupled to the generator 1010 and an energy delivery element 1024 (e.g., structurally and/or functionally similar to the energy delivery element 124 of FIG. 1) operatively coupled to the energy delivery element 1124.

The housing 1001 may be an enclosure, container, and/or the like configured to store the power source 1002, the generator 1010, and the electrosurgical interface 1022. The housing 1001 may be a form-factor that is able to be held in the hand of a surgeon. A handheld electrosurgical system 1000 allows for a system that has reduced complexity as the number of separate components is reduced, thereby reducing complexity during operation. The handheld electrosurgical system 100 also allows for the fewer supporting staff to be desired when using the system and reducing the number of wires, cables, and/or devices on the treatment table. In some embodiments, the shape of the housing 1001 can be ergonomic to facilitate usaage by a medical professional. In some embodiments, the housing 1001 can include a power source 1002 (e.g., battery, etc.). Using a battery or similar power source 1002 reduces the risk of inadvertent electrical energy related issues from a power source 1002. In some embodiments, the power source 1002 is a reusable, rechargeable battery pack. In some embodiments, the housing 1001 is electrically coupled to an external power source 1002 that provides power to the electrosurgical system 1000. In some embodiments, the housing 1001 can include a button, a display, and/or the like to operate the generator 1010. In some implementations, the handheld housing 1001 can be sterilized and reused.

The energy delivery element 1024 is configured to operatively couple to the electrosurgical interface 1022. The housing 1001 can be configured to couple to the end of the energy deliver 1024 or the energy delivery element 1024 can be configured to slide, operatively, through the housing 1001. The return electrode 1030 is configured to operatively couple to the generator 1010 and to couple to the patient.

Energy Delivery Element or Guidewire

Figure 8A:
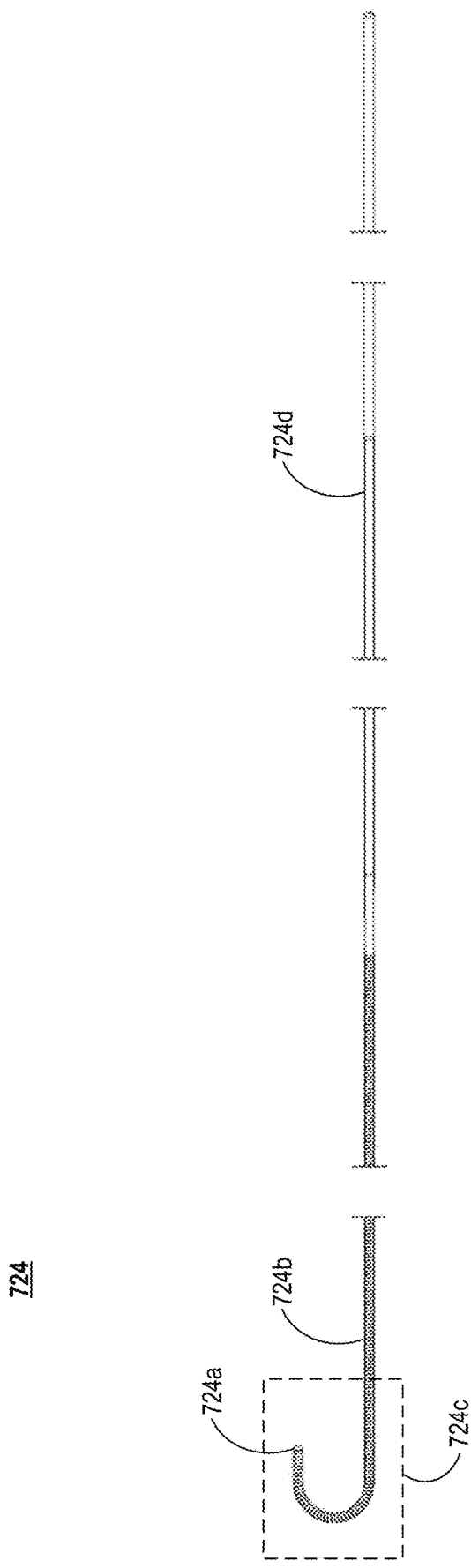
FIG. 8A depicts an example of a guidewire of an electrosurgical device, according to embodiments.
Figure 8B:
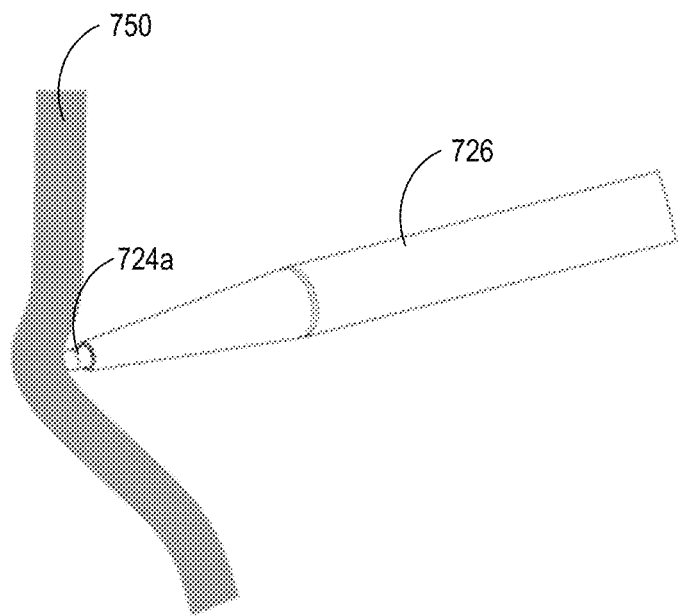
FIGS. 8B and 8C depict the operation of the guidewire of FIG. 8A in crossing a tissue structure, according to embodiments.
Figure 8C:
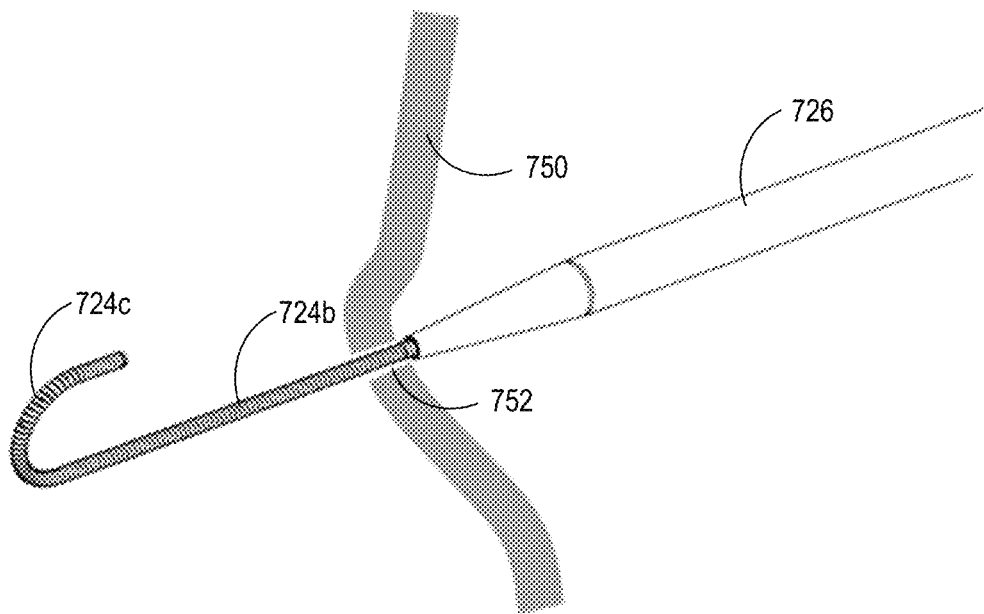

FIGS. 8A-8B depict a guidewire 724 of an electrosurgical device (e.g., electrosurgical device 100, 200, 400), according to an embodiment. FIG. 8A provides a side view the guidewire 724 with break points to better show details of the various components of the guidewire 724. FIGS. 8B and 8C depict perspective views of a guidewire 724 within a dilator 726 forming an opening and pushing through tissue 750. The guidewire 724 may be functionally and/or structurally similar to the energy delivery element 124 of FIG. 1 and/or the guidewire 424 of FIG. 4.

As depicted in FIG. 8A, an embodiment of the guidewire 724 includes a tip 724a, a distal curved portion 724c, a distal segment 724b, and proximal segment 724d. The guidewire 724 is formed of stainless steel with a tapered core wire and a distal coil welded at the tip 724a and a proximal termination (e.g., the distal end of the proximal segment 724d). Optionally, the core wire may be formed of nitinol. The guidewire 724 is formed of biocompatible and sterile materials.

The distal segment 724b and/or proximal segment 724d are conduct energy when in use (e.g., from an electrosurgical interface). The distal segment 724b may be conductive along its length. at or near a proximal end of the distal segment 724b. The proximal segment 724d may have an exposed conductive region that is configured to electrically couple with an electrode of an electrosurgical interface (e.g., the electrode 448 of FIG. 5B). When energized, the proximal segment 724d conducts this energy to the distal tip 724a of the guidewire. In some embodiments, the proximal segment 724d may be partially or wholly insulated so that it may be handled while in use. For example, a proximal portion of the proximal segment 724d may be covered with an insulative layer. The insulation can prevent electrical current from flowing through the wire and into the hands of a physician. The insulative coating may be, for example, polytetrafluoroethylene, perfluoro alkoxy alkane, fluorinated ethylene propylene, polyimide, epoxy, ceramic, nylon, and/or a composite of insulating materials. The proximal segment 724d is stiff to facilitate exchange of large bore sheaths through tortuous patient anatomy. The distal segment 724b and/or the proximal segment 724d (or portions thereof) can have a gold plating applied over a stainless-steel core to improve conductivity, including heat conductivity. Such conductivity may be beneficial for conductive heat away from a distal tip of the guidewire, e.g., to prevent overheating at the distal tip of the guidewire. In some embodiment, the core of the guidewire 724 may be coated in tungsten or other conductive material.

The distal segment 724b can be less stiff than the proximal segment 724d. In some embodiments, the distal segment 724b includes a non-conductive or insulating coating over a portion of it or the distal segment 427b may be uninsulated. For example, as described with reference to FIG. 1, the distal segment 724b may have an insulating collar that surrounds a short portion of the guidewire near or adjacent to the distal tip of the guidewire. In some embodiments, the distal collar may be between about 2 mm and about 10 mm in length, including all sub-ranges and values therebetween. The distal end of the distal portion 724b includes a curved portion 724c. The curved portion 724b is formed of a shape memory material. The curved portion 724b may be a J-shape, as in FIG. 8A, but other shapes are possible including a straight shape and/or other curved or spiral shapes (e.g., a pigtail, a coil, etc.). The J-shape of FIG. 8A is atraumatic as to no cause damage to patient anatomy while being navigated therethrough. The guidewire 724 can remain in its J-shape when unconstrained and being navigated through patient anatomy to a target tissue. For applying energy to tissue, however, the guidewire 724 can be constrained to a straighter configuration, e.g., so that the distal tip 724a of the guidewire is positioned to apply energy to and puncture through tissue. For example, when the guidewire 724 is retracted within a sheath or dilator (e.g., the sheath 126), the guidewire 724 can thereby be constrained to a straight or substantially straight configuration. The tip 724a is a conductive and/or non-insulated portion of the distal segment 724b. The tip 724 can be energized to deliver energy (e.g., RF energy) to tissue to create a perforation or opening; for example, by actuating the electrosurgical interface 122 to transfer energy from the generator 110 to an exposed region of the wire slidably positioned therethrough As discussed above, the guidewire 724 can again take a J-shape if extended beyond a perforation in the target tissue.

FIGS. 8B and 8C show the guidewire 724 in use. The guidewire 724 and the sheath 126 can be advanced through patient vasculature to a target site. In FIG. 8B, the guidewire 724 is sheathed in a dilator 726 (e.g., functionally and/or structurally similar to the sheath 126 of FIG. 1 and/or other sheaths and dilators described herein) such that only the tip 724a protrudes from the dilator 726. In such a configuration, the tip 724a is located in line (or approximately in line) with a longitudinal axis of the dilator 726. In some applications (e.g., when crossing the septum), the tip 724a can press against the tissue 750, as shown in FIG. 8B. This can be part of tenting the tissue. Upon actuation, RF energy is transmitted from the generator to the tip 724a and heats the tissue 750 at the point of contact. Heating the tissue 750 results in dehydration, protein denaturing, and a loss of mechanical integrity of the tissue. The dilator 726 may then be advanced into the point of contact to form a puncture within the tissue 750, allowing the guidewire 724 to be advanced into the puncture. Once a puncture is formed, the energy input is terminated.

In FIG. 8C, a puncture 752 has been formed in the tissue 750 and a portion of the distal segment of the guidewire 724 has been advanced through the puncture 752. As can be seen in FIG. 8, the dilator can have a conical to tapered tip such that when the dilator 726 is pushed farther through the puncture 752, it expands or dilates the puncture. A secondary therapeutic device (e.g., ablation catheter, sheath, etc.) may be advanced through expanded puncture, optionally over the guidewire 724 after removal of the dilator 726. Thus, the guidewire 724 acts as both an energy delivery device and a mechanism for guiding further surgical instrumentation or medical devices.

FIGS. 9A and 9B depict different examples of guidewires (924a and 924b) (e.g., structurally and/or functionally similar to the energy delivery element 124 of FIG. 1 and other guidewires described herein) of an electrosurgical device such as the electrosurgical device 120 of FIG. 1, according to embodiments. The guidewires 924a and 924b include two segments, where one segment is conductive (e.g., metallic) while the other is at least outwardly nonconductive (e.g. has an insulating coating). The different segments of the guidewires 924a and 924b can have different colors, e.g., to identify the guidewire as being a purpose-specific guidewire (such as, for example, one to use for forming perforations) and/or to aid an operator in distinguishing between the different portions of the guidewire 924a and 924b. The resulting two-tone design may be quickly identified by a physician during an operation.

The guidewires 924a and 924b include proximal segments 924d and 924f and distal segments 924c and 924e connected at transition points A and B, respectively. The distal segments 924c and 924e are metallic or have a metallic layer and provide a contiguous conductor from transition points A and B, respectively, to the distal end of the guidewire (e.g., for applying electrosurgical treatment). The distal segments 924c and 924e may be plated gold over stainless steel or another base metal such as tungsten. The outer layer of the distal segments 924c and 924e may cover manufacturing artifacts from welding, heat setting, or shaping, resulting in a smooth consistent surface finish. The proximal segments 924d and 924f (or at least portions thereof) are coated with an insulative coating. The coating may be PTFE, FEP, polyimide, epoxy or nylon. The polymer may be extruded, reflowed, or applied by coating. The coating may be a single uniform color, a repeating pattern, or a variety of different length segments including different colors.

As shown in FIGS. 9A and 9B, the ratio of the length of the distal segment to the length of the proximal segment may vary across different guidewires. In some embodiments, the distal segment forms at least about 20% and no more than 80% of the total length of the guidewire. In the guidewire 924a of FIG. 9A, the distal segment 924c is longer than the proximal segment 924d. In the guidewire 924b of FIG. 9B, the proximal segment 924f is longer than the distal segment 924e. In some embodiments, the distal segment and the proximal segment may be approximately equal in length.

Figure 11A:
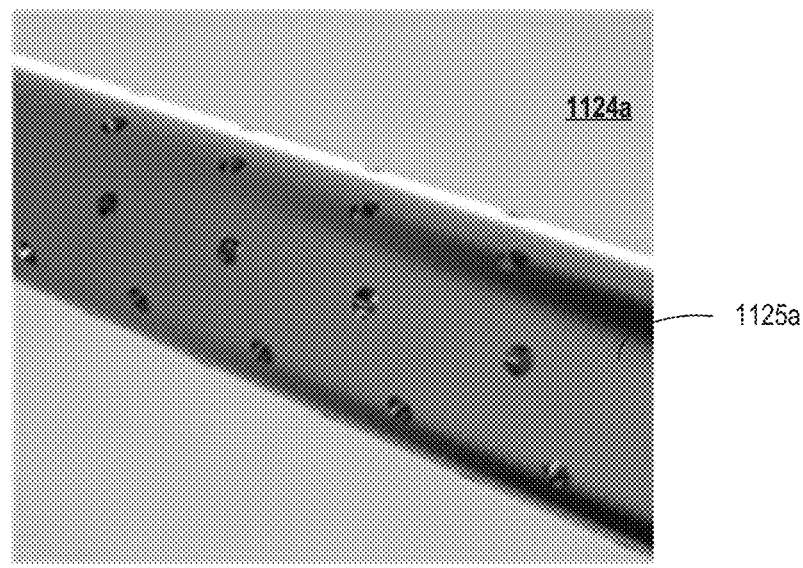
FIG. 11A depicts an example guidewire with openings in an insulative coating of the guidewire, according to embodiments.
Figure 11B:
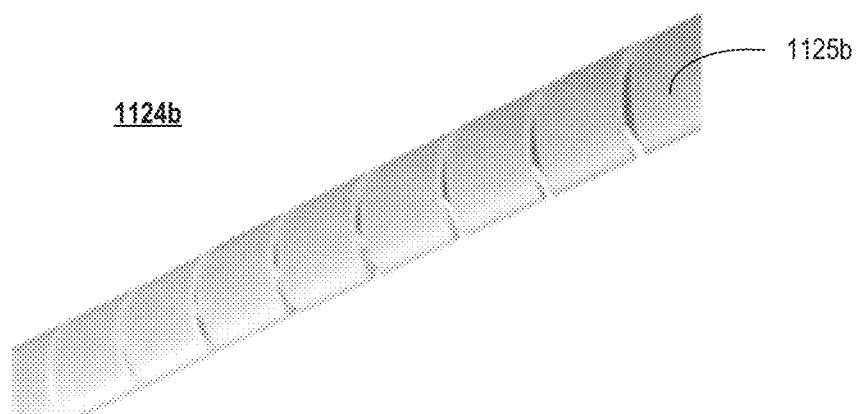
FIG. 11B depicts an example guidewire with a helical cut in the insulative coating of the guidewire, according to embodiments.

In an embodiment, guidewires or other energy delivery elements as described herein can be formed of multiple layers. The center of the guidewire can be a conductive core wire, which can be configured to carry current from an electrosurgical interface to a distal tip of the guidewire. One or more additional layers, e.g., coatings, coils, etc., surround the core wire. To enable a conductive path from an outer layer of the guidewire to the core wire, one or more conductive paths may be formed between the core wire and the outer layer of the guidewire. Referring generally to FIGS. 11A and 11B, examples of guidewires (1124a and 1124b) are shown. The guidewires 1124a and 1124b can be coated with an electrical insulator 1125a, 1125b, respectively. In some implementations, the insulator is a polymer. A portion of the insulative coatings 1125a, 1125b of the guidewires 1124a and 1124b may be absent (e.g., removed using a laser or mechanical cutting instrument) to expose the conductive elements to allow for electrical conductivity to the conductive elements. For example, the exposed area may be a plurality of openings in the coating of the guidewire 1124a, as seen in FIG. 11A, or a helical cut in the coating of the guidewire 1124b, as seen in FIG. 11B, though other cutting patterns could be used. The exposed area creates one or more conductive zones to the conductive elements beneath for redundancy and for increasing a path for current flow to the conductive elements beneath. In some embodiments, after portions of the coating have been exposed, the coating can be coated with a conductive coating (e.g., a metallic coating). In some embodiments, the exposed area can be used to establish electrical communication between the core wire of the guidewire and an electrosurgical interface, such as, for example, the electrosurgical interface 122 of FIG. 1. In some embodiments, the exposed area can be used to create a larger conductive surface area or active electrode region for the guidewire, which can be used to reduce the current density at a tip of the guidewire by distributing the charge or current across a larger conductive surface area of the guidewire. Further details of such guidewires are described with reference to FIGS. 40 and 41.

Figure 14:
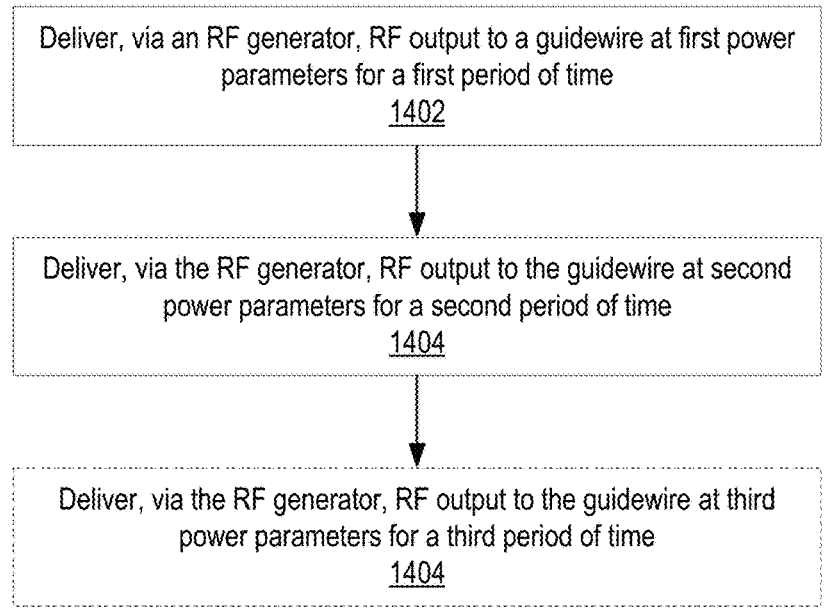
FIG. 14 is a flow chart depicting a method of delivering a RF output to a guidewire, according to embodiments.
Figure 15A:
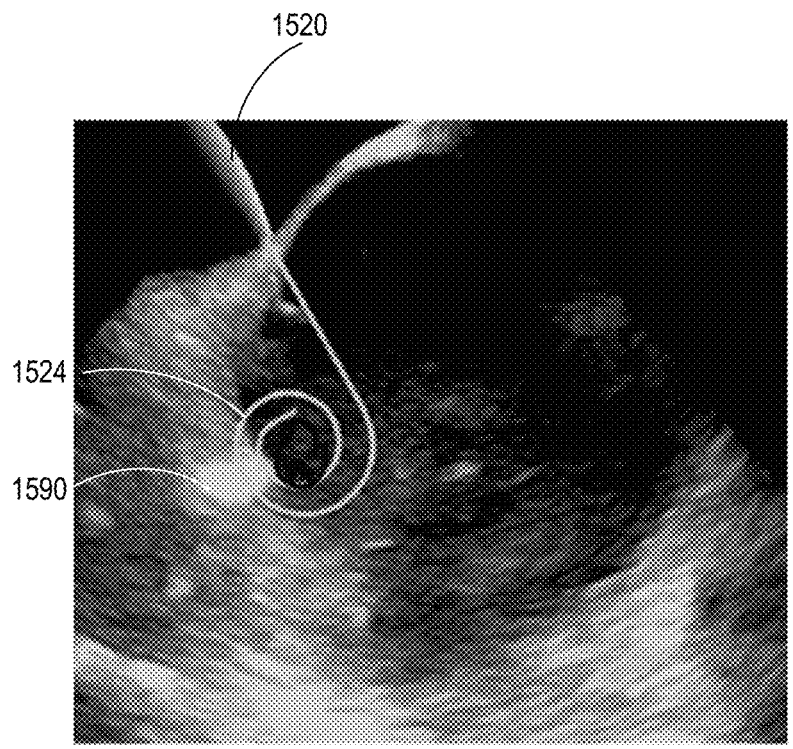
FIGS. 15A-15B depict an unintentional lesion being formed by an electrosurgical device in a heart of a patient, according to embodiments.
Figure 15B:
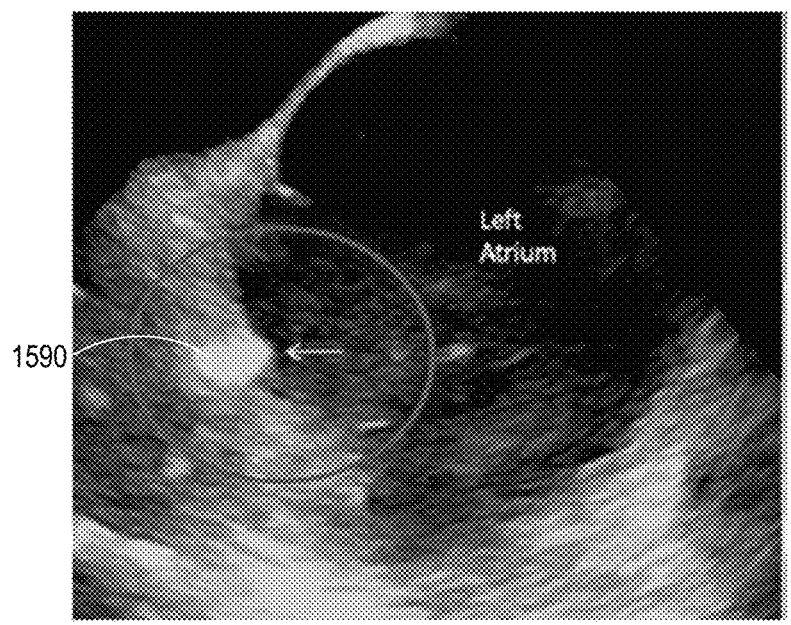

FIGS. 15A-15B depict an unintentional lesion being formed by an electrosurgical device accessing a heart. The heart depicted includes the unintentional lesion 1590 in the left atrium, as seen in FIGS. 15A and 15B. FIG. 15A depicts an illustration of the lesion 1590 being formed due to a guidewire of a transseptal device or other electrosurgical device 1520. The guidewire of the electrosurgical device 1520 may have contacted the wall of the left atrium after deploying from a sheath causing the lesion 1590. The systems, devices, and methods described herein are configured to decrease the likelihood of lesions, such as lesion 1590 forming. For example, the methods described in reference to FIGS. 13 and 14 below can be configured to decrease RF output when the RF output of the electrosurgical device is not desired. Additionally or alternatively, the configuration and design of the guidewires or energy delivery elements, as described in the following figures, can reduce the risk of lesion formation, e.g., by having lower current density as the guidewires are extended distally out from a dilator or outer sheath.

In some embodiments, the guidewires or energy delivery elements of the electrosurgical systems described herein can be configured to have lower current density when they are extended distally beyond a septum, while still maintaining higher current density when puncturing through the septum. In particular, the guidewires described herein can have a longer conductive length, such that when the guidewires are extended into the blood pool beyond the septum, the longer conductive length of the guidewires spreads out the current density along the length of the guidewire. This then reduces the current density at any point along the guidewire, thereby reducing the risk of injury to the myocardium, should the guidewire come into contact with the heart wall.

For example, a guidewire can include first distally electrically conductive portion that has a length of about 1.0 mm, a first insulating region that has a length of about 0.5 mm, and a second conductive region that has a length of about 12.0 cm. The first conductive portion and the second conductive portion can include metallic structures including coils (e.g., stainless steel coils, tungsten coils, etc.) while the insulating region can include a polymeric jacketing materials, such as polyolefin, polyethylene terephthalate, and/or the like. When the distal tip of the guidewire extends a distance of less than about 5 mm beyond the dilator, the tip of the guidewire can be configured to have a current density of between about 10 A/cm$^2$ to about 250 A/cm$^2$, including all subranges and values therebetween. In embodiments, the current density can be greater than 10 A/cm$^2$ when the tip is extended a first distance of less than 1 mm beyond the dilator. Further, the tip of the guidewire can be configured to have a current density of less than 60 A/cm$^2$ when the distal end of the guidewire extends less than about 5 mm beyond the dilator. For example, the current density can be about 60 A/cm$^2$ when the distal tip is extended less than or equal to about 0.5 mm of the sheath. Further, the tip of the guidewire can be configured to have a current density of less than about 50 A/cm$^2$, or less than about 40 A/cm$^2$, or less than about 30 A/cm$^2$, or less than about 25 A/cm$^2$, or less than about 20 A/cm$^2$, or less than about 15 A/cm$^2$, or less than about 10 A/cm$^2$, or less than about 5 A/cm$^2$, when the tip extends beyond about 5 mm beyond the dilator. For example, when the tip extends a second distance greater than 7 mm beyond the dilator, the tip can have a current density of less than about 30 A/cm$^2$.

Figure 16:
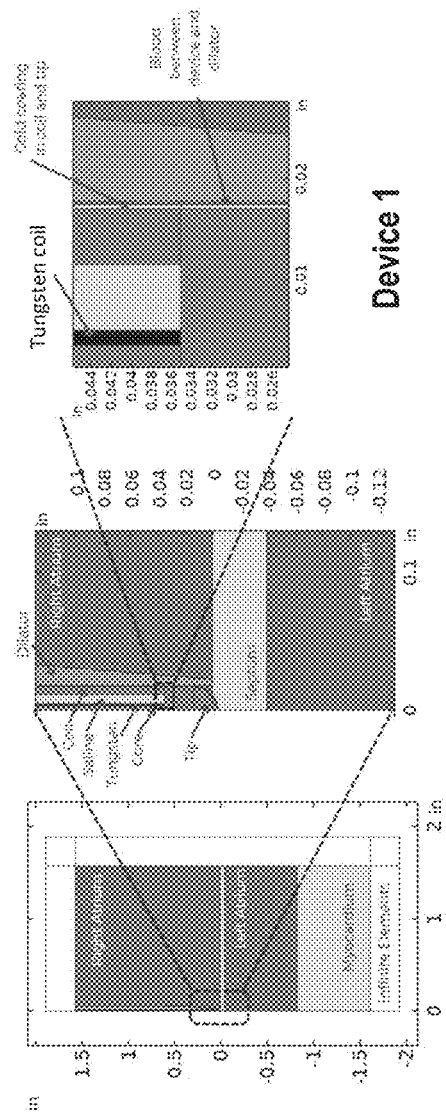
FIG. 16 schematically depicts an electrosurgical device including a guidewire and a dilator, according to embodiments.
Figure 17:
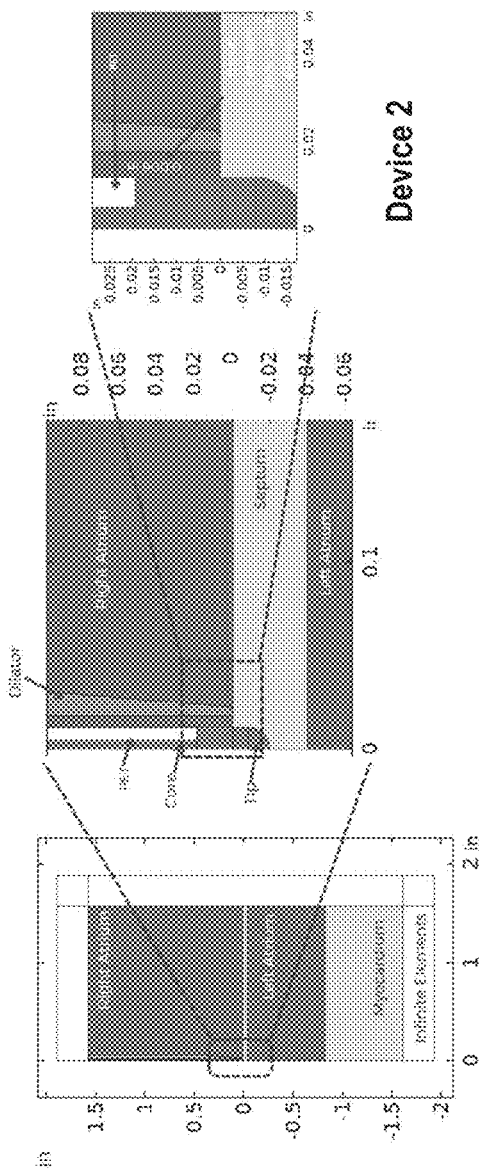
FIG. 17 schematically depicts an electrosurgical device including a guidewire and a dilator, according to embodiments.

Referring to FIGS. 16-27C, a comparison between the operation of two electrosurgical devices, Device 1 and Device 2, is shown. As shown, the two electrosurgical devices operate differently, e.g., due to a difference in design of their guidewires. Device 1 represents an electrosurgical device including a guidewire that is similar to embodiments of energy delivery elements and guidewires described herein, whereas Device 2 represents a device including an existing guidewire that may be used in transseptal procedures. FIGS. 16 and 17 provide more details of the construction of guidewires of Devices 1 and 2.

FIG. 16 depicts a cross-section of Device 1 (e.g., functionally and/or structurally similar to the electrosurgical device 120 of FIG. 1) including a guidewire or energy delivery element and a dilator, according to an embodiment. The energy delivery element can be functionally and/or structurally similar to other energy delivery elements or guidewires described herein, and the dilator can be functionally and/or structurally similar to other sheaths or dilators described herein. The energy delivery element, as seen in FIG. 16, includes a tip, a core, a coating (e.g., tungsten) around the core, inner and outer coils (e.g., formed of tungsten), and gold coating in the coil and tip. The energy delivery element may include a larger active electrode region or conductive outer surface, as described above. In use, the energy delivery device can be flushed with a fluid, such as saline. The energy delivery element can be disposed within the dilator, and a blood or fluid layer may be disposed between the energy delivery element and the dilator.

FIG. 17 depicts a cross-section of Device 2 including a guidewire or energy delivery element and a dilator. The energy delivery element includes a tip, a core, and a PET coating (e.g., insulative coating) that covers the conductive portions of the guidewire proximal of the tip. The energy delivery element can be disposed within the dilator, and a blood or fluid layer may be disposed between the energy delivery element and the dilator. The main difference between the guidewire of Device 1 and the guidewire of Device 2 lies in the addition of the insulative coating in the guidewire of Device 2, which covers the guidewire in all regions except for the tip or distal end portion of the guidewire. With the addition of this insulative coating, the only exposed conductive portion of the guidewire is the tip of the guidewire. Therefore, any energy that is delivered to the guidewire of Device 2 is concentrated at the tip, as reflected in the operation of the devices as shown in FIGS. 18-27C and 36-38B.

Figure 18:
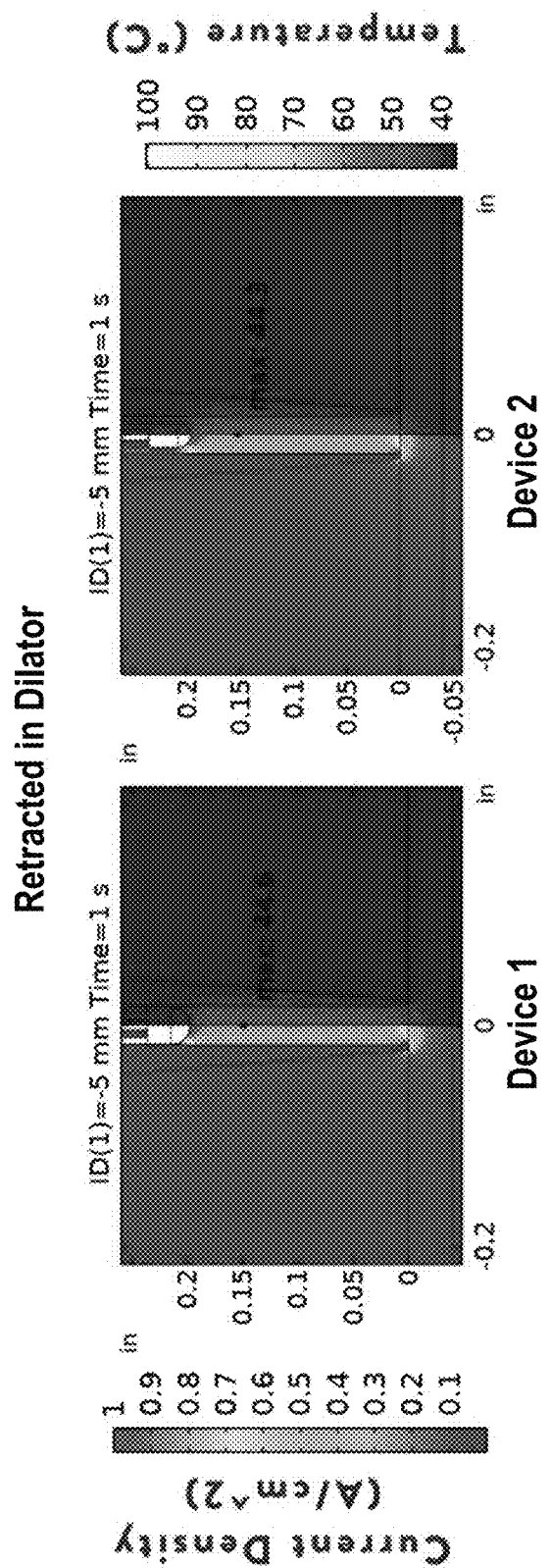
FIG. 18 depicts the current density and temperature around the electrosurgical devices of FIGS. 16 and 17, when the guidewire is retracted in the dilator.

FIGS. 16-27C and 36-38B depict the operation of the guidewires of Devices 1 and 2, under simulated conditions. The simulated conditions are used to demonstrate the differences in operation of the guidewires of Devices 1 and 2. While certain values of current density, temperature, and other parameters may be shown in these figures, it can be appreciated that other values may exist during actual, non-simulated operation of the devices. FIG. 18 depicts the current density and temperature of the electrosurgical devices of FIGS. 16 and 17, when the guidewire is retracted in a dilator, e.g., at an insertion depth of −5 mm from the septum wall. The insertion depth reflects the distance that the tip of the guidewires of Device 1 and Device 2 are distal to the top surface of the septum, and therefore a negative insertion depth indicates that the tip of the guidewires of Devices 1 and 2 are proximal of the top surface of the septum. As seen in FIG. 18, when disposed within the dilator (e.g., after retraction), Device 1 and Device 2 have similar current density and thermal properties. For example, the maximum temperature of Device 1 is 44.6° C., and the maximum temperature of Device 2 is 44.3° C.

Figure 19:
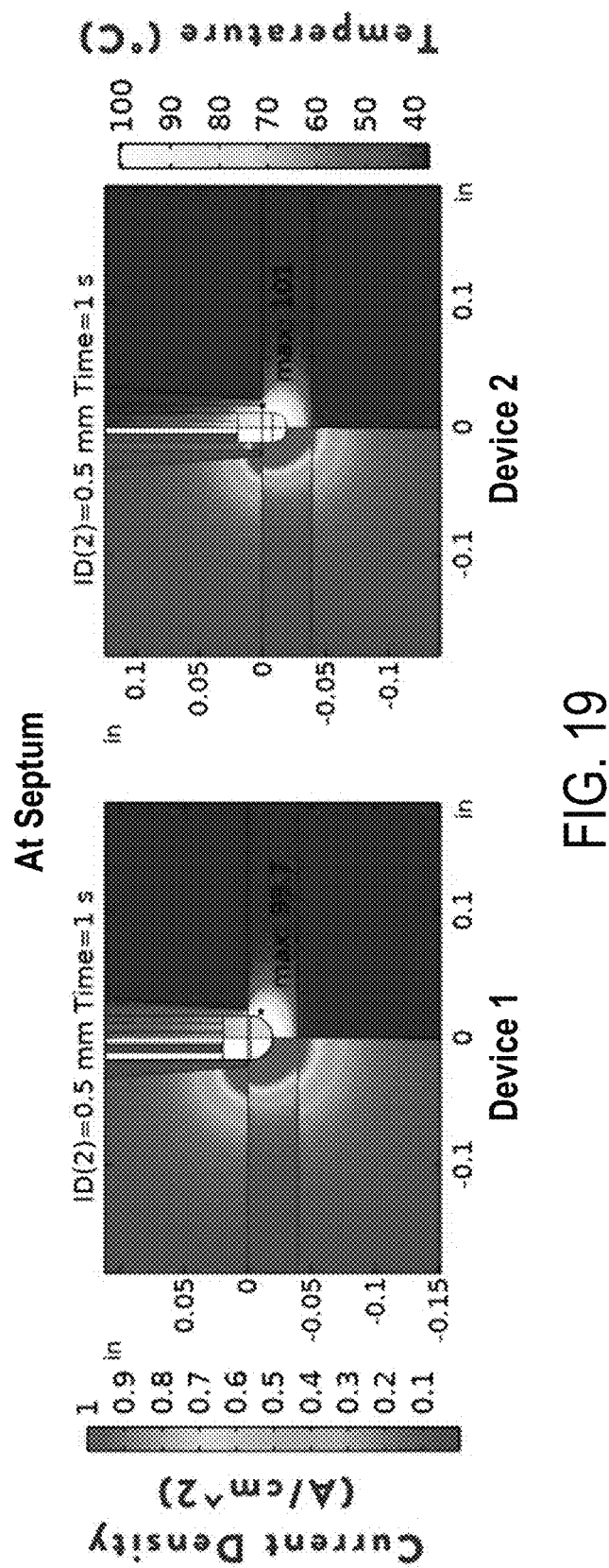
FIG. 19 depicts the current density and temperature around the electrosurgical devices of FIGS. 16 and 17, when the guidewire has been extended out of the dilator and is engaging a septum.
Figure 36:
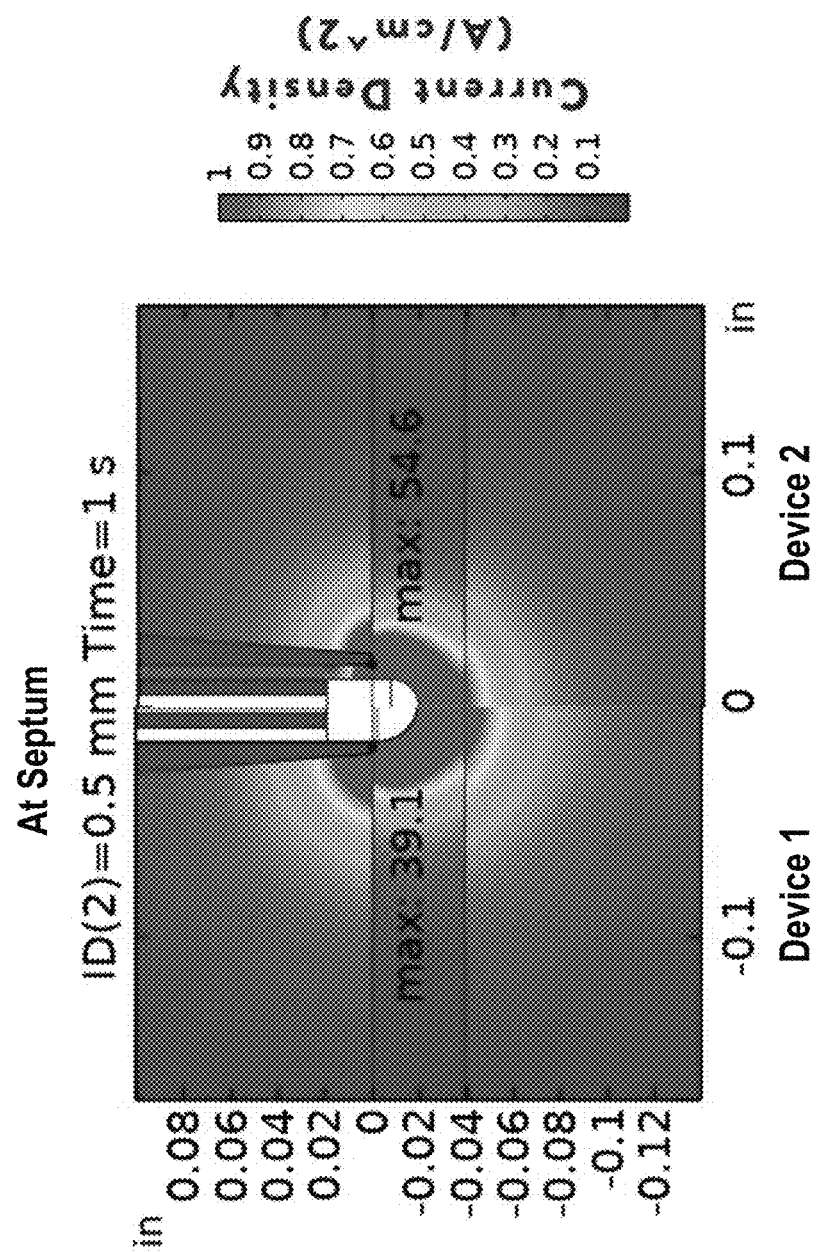
FIG. 36 depicts the current density around the electrosurgical devices of FIGS. 16 and 17 at the septum.

FIG. 19 depicts the current density and temperature of the electrosurgical devices of FIGS. 16 and 17, when the guidewire has been extended out of the dilator a short distance and is engaging a septum (insertion depth of 0.5 mm into the septum wall). As seen in FIG. 19, while Device 1 has a slightly lower maximum temperature than Device 2 (e.g., 99.7° C. compared to 101° C.), both guidewires deliver comparable levels of energy for perforating or puncturing through the septum. Additionally, given the slightly wider geometry of the tip of the guidewire of Device 1 compared to the tip of the guidewire of Device 2, the guidewire of Device 1 generates a wider current density distribution at the septum, which may further facilitate puncturing through the septum. FIG. 36 depicts the current density distribution of the guidewires of Devices 1 and 2, along with maximum current. As shown in FIG. 36, the maximum current density of Device 1 is about 39.1 A/cm$^2$, while the maximum current density of Device 2 is about 54.6 A/cm$^2$.

Figure 20:
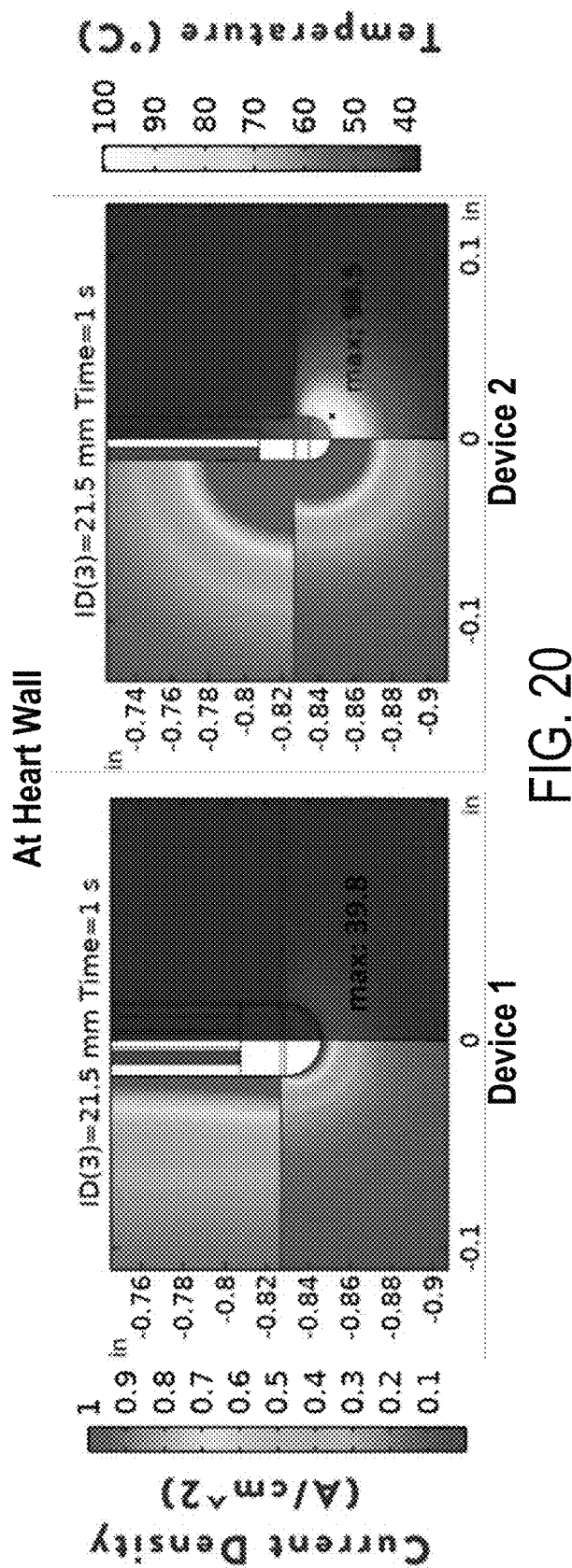
FIG. 20 depicts the current density and temperature around the electrosurgical devices of FIGS. 16 and 17, when the guidewire has been extended out of the dilator and is at the heart wall.
Figure 37:
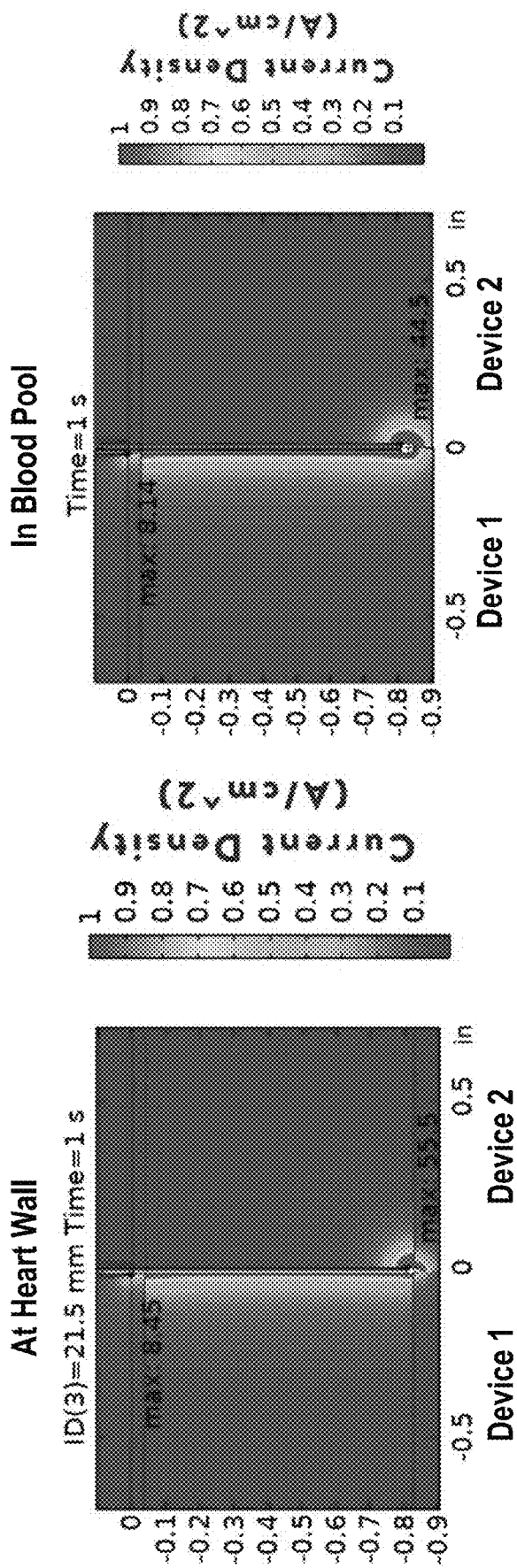
FIG. 37 depicts the current density around the electrosurgical devices of FIGS. 16 and 17 when the dilator is retracted when the electrosurgical devices are at the heart wall and in the blood pool.

FIG. 20 depicts the current density and temperature of the electrosurgical devices of FIGS. 16 and 17 when the guidewire has been extended out of the dilator and is at the heart wall, e.g., at an insertion depth of 21.5 mm from the septum wall. As noted above, the insertion depth reflects the distance that the tip of the guidewires of Device 1 and Device 2 is distal to the proximal surface of the septum. As seen in FIG. 20, the current of Device 1 is more distributed across an exposed length of Device 1 compared to Device 2. As such, the current density at the heart wall for Device 1 is significantly lower than the current density at the heart wall for Device 2. This is depicted in FIG. 37, which shows that the guidewire of Device 1 has a maximum current density of 8.45 A/cm$^2$ at the heart wall and the guidewire of Device 2 has a maximum current density of 55.5 A/cm$^2$ at the heart wall. The lower current density of Device 1 at the heart wall is due to Device 1 having a longer, exposed conductive length, which acts to spread out or dissipate the energy that is being delivered to the tip of the guidewire. In comparison, Device 2 only includes a conductive portion at the tip, due to its insulative coating, which therefore concentrates the current density at its tip. The lower current density indicates that Device 1 has a lower likelihood of causing undesired tissue damage than Device 2. Moreover, the temperature of Device 1 at its tip is significantly lower than that of Device 2. Specifically, the simulation results in FIG. 20 show that maximum temperature of Device 1 is 39.8° C. and the maximum temperature of Device 2 is 98.5° C. Thus, a user of Device 1 is less likely to damage the heart wall than a user of Device 2. The lower temperature of Device 1 can be due to heat wicking or dissipation across a larger length of the device, as compared to Device 2. As described earlier with respect to FIG. 16, Device 1 can include a gold coating that can be configured to conduct away heat from the distal tip of the device. As such, the temperatures at the tip of Device 1 are lower, and therefore, Device 1 is also less likely to cause unintentional damage or inquiry to tissue surfaces, including, for example, the heart wall. While gold is provided as an example of a material that can conduct heat away from the tip of Device 1, it can be appreciated that any other type of thermal conductor can be used as a coating, layer, or other component of Device 1 (or any of the other energy delivery elements or guidewires described herein) to reduce heat at the tip of the device. For example, materials such as diamond (e.g., applied using chemical vapor deposition (CVD)) can be applied to one or more components of the energy delivery elements/guidewires described herein to provide electrical insulation and/or reduce temperatures at the tip of such components.

Figure 21:
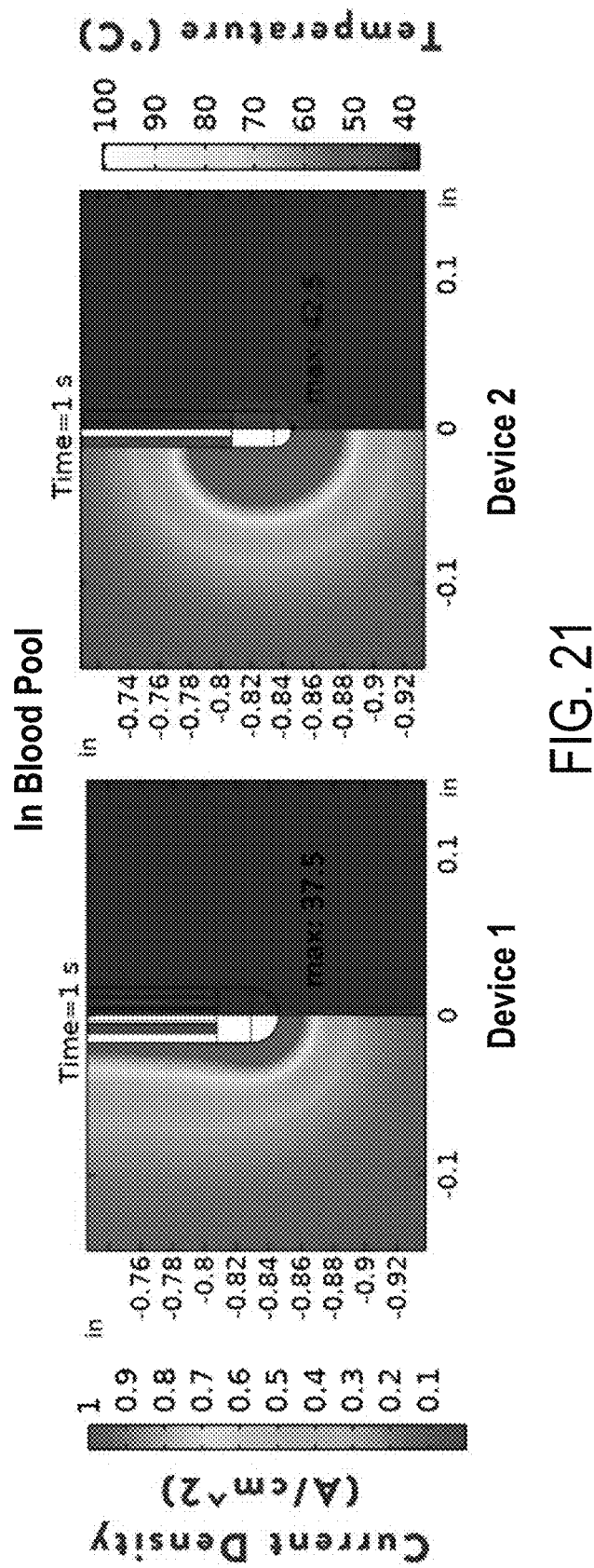
FIG. 21 depicts the current density and temperature around the electrosurgical devices of FIGS. 16 and 17, when the guidewire has been extended out of the dilator and is located in the blood pool.

The phenomenon of distributed current density can be further seen in FIG. 21, which depicts the current density and temperature of the electrosurgical devices of FIGS. 16 and 17 when the guidewire has been extended out of the dilator and is located in the blood pool (e.g., of the left atrium). As seen in FIG. 21, the current density generated by Device 1 is distributed along the length of the guidewire while the current density generated by Device 2 is concentrated around the tip of the guidewire. As described above, this concentration can be problematic, as it may cause a lesion if it comes into contact with the heart wall, such as the lesion seen in FIGS. 15A and 15B. The distributed current density and lower current density values generated by Device 1 is less likely to cause a lesion as the current density gets distributed along the length of the guidewire. FIG. 37 shows that the guidewire of Device 1 has a maximum current density of 8.14 A/cm$^2$ in the blood pool and the guidewire of Device 2 has a maximum current density of 44.5 A/cm$^2$ in the blood pool. Additionally, the temperature of Device 1 at its tip is lower than that of Device 2. Specifically, the simulation results in FIG. 21 show that maximum temperature of Device 1 is 37.5° C. and the maximum temperature of Device 2 is 42.5° C. While being in the blood pool helps dissipate heat buildup at the tips of both Devices 1 and 2, the additional gold coating of Device 1, which can help to wick heat away from the tip, further assists with pulling heat away from the tip of Device 1.

As shown in FIG. 37, both at the heart wall and in the blood pool, the maximum current density of Device 1 is substantially less than the maximum current density of Device 2. As described above, this difference is due to Device 1 allowing for current to dissipate along the length of the guidewire instead of concentrating the current at the tip of the guidewire as in Device 2.

Figure 38B:
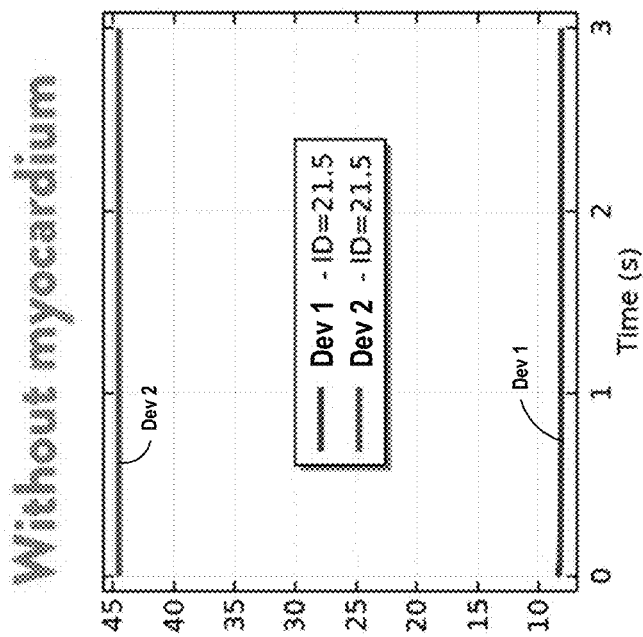
FIGS. 38A-38B are graphs of the current density around the electrosurgical devices of FIGS. 16 and 17, when the guidewire is disposed against the septum, has been inserted through the septum and is disposed against a heart wall (with myocardium), or in the blood pool (without myocardium).
Figure 38A:
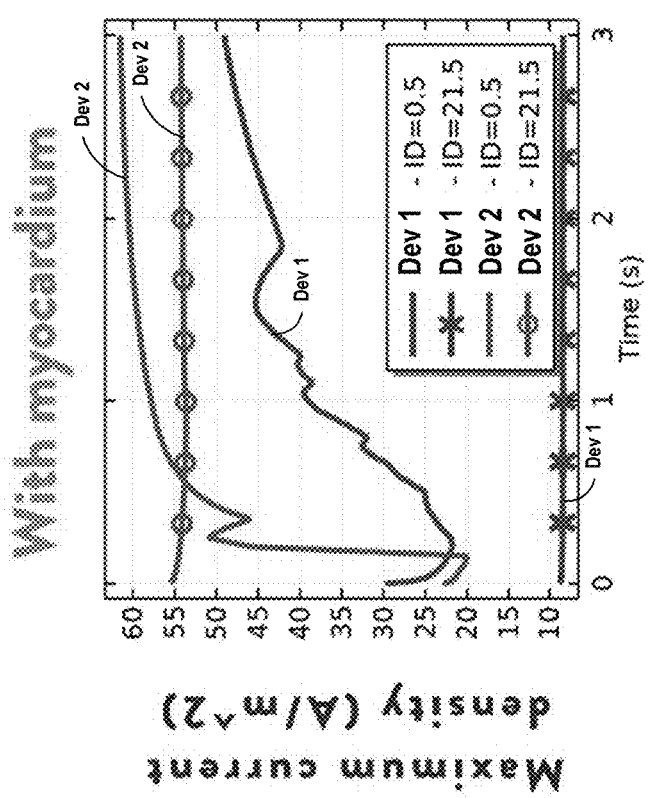

FIGS. 38A-38B plots the maximum current density of the guidewires of Devices 1 and 2, when the guidewire is disposed against the septum (ID=0.5, with myocardium), has been inserted through the septum and is disposed in the blood pool (ID=21.5, without myocardium), and is disposed against a heart wall (ID=21.5, with myocardium). As shown again in these plots, Device 1 and Device 2 may have a sufficiently high maximum current density at the septum to allow them to puncture through the septum, while Device 1 has a significantly lower maximum current density compared to Device 2 after penetrating through the septum. The lower current density at the heart wall and in the blood pool decrease the likelihood of a lesion formed by accident.

Figure 22:
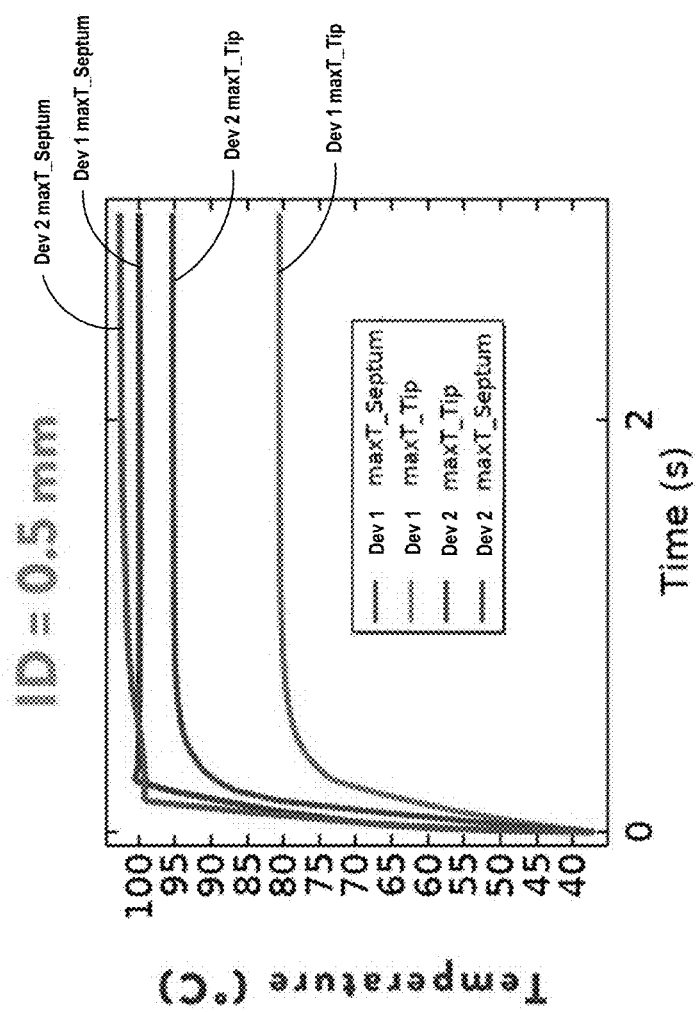
FIG. 22 is a graph of temperature over time of the electrosurgical devices of FIGS. 16 and 17, when the devices are at the septum.

FIG. 22 depicts, as a function of time, the temperature of the septum and the tip of the guidewires, for Devices 1 and 2, at an insertion depth of 0.5 mm, i.e., when the tips are engaged with the septum wall. As seen in FIG. 22, the temperature at the septum from Devices 1 and 2 are approximately 100° C. However, the tip temperature of Device 1 is lower than the tip temperature of Device 2, indicating that the guidewire of Device 1 dissipates heat more effectively than the guidewire of Device 2. As shown in FIG. 16, the guidewire of Device 1 may include gold plating. Gold is an effective heat conductor, and therefore may contribute to the dissipation or wicking of heat away from the tip of the guidewire. While gold is provided as an example of an effective heat conductor, other heat conducting materials can also be used, e.g., diamond, other metals, etc.

Figures 23A, 23B, 23C:
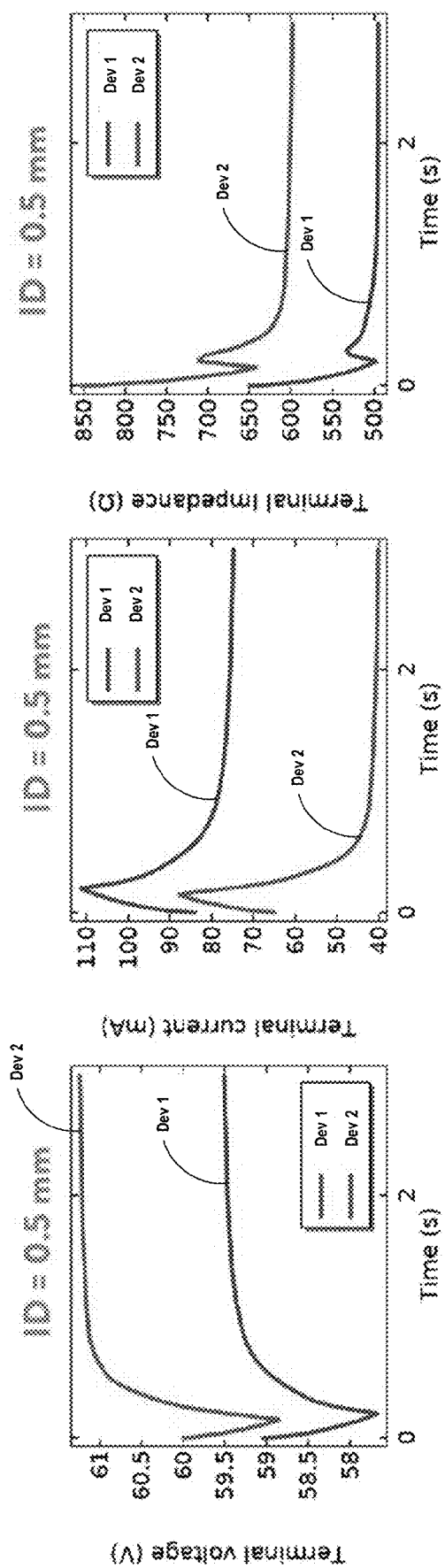
FIGS. 23A-23C are graphs of the terminal voltage, terminal current, and terminal impedance of the electrosurgical devices of FIGS. 16 and 17, when the guidewire is at the septum, at an insertion depth of 0.5 mm.

FIGS. 23A-23C depict graphs of the terminal voltage, terminal current, and terminal impedance, respectively, of the electrosurgical devices of FIGS. 16 and 17 when the guidewire is at the septum at an insertion depth of 0.5 mm. As seen in FIGS. 23A-23C, Device 1, when energized, has a smaller terminal voltage, greater terminal current, and smaller terminal impedance than Device 2. While there is a difference in terminal voltage between Device 1 and Device 2, the difference is not significant at the insertion depth of 0.5 mm, allowing for Device 1 to also be effective at penetrating through tissue.

Figures 24A, 24B:
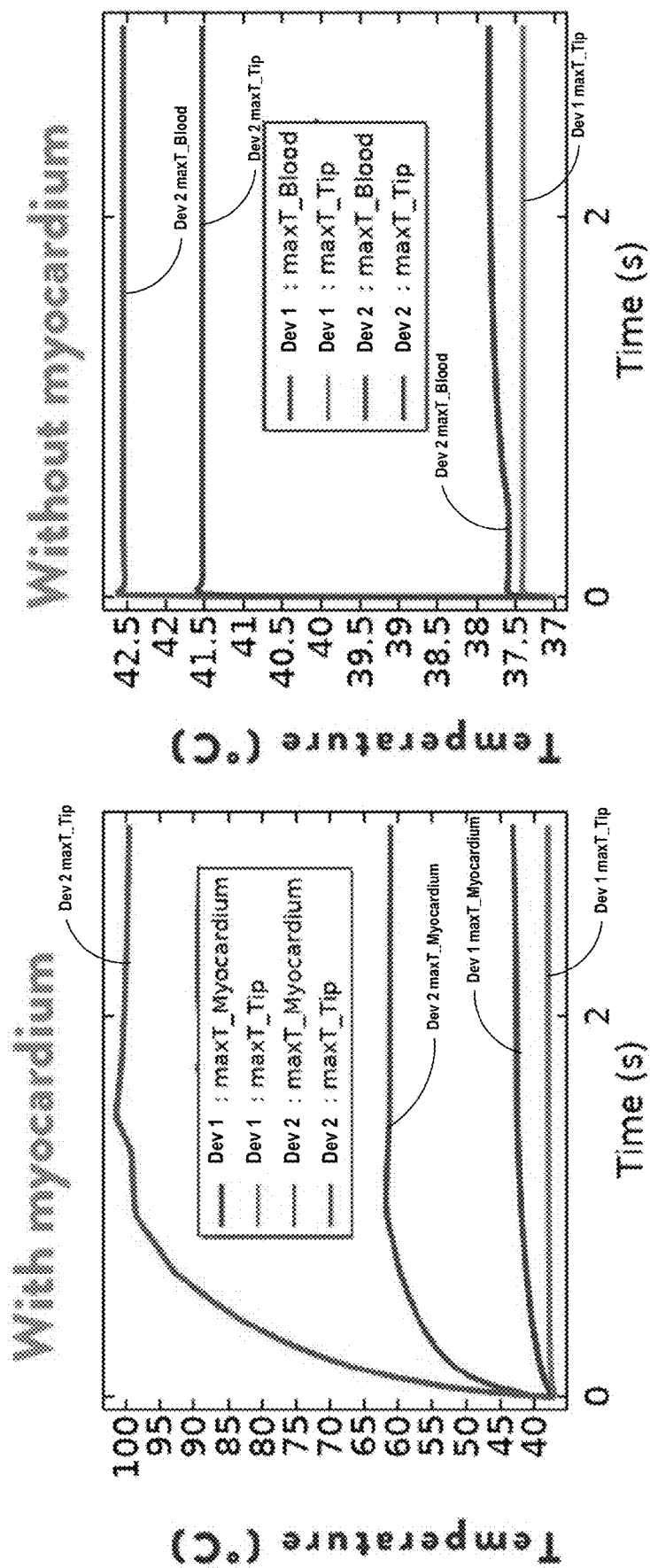
FIGS. 24A and 24B are graphs of the temperature of the electrosurgical devices of FIGS. 16 and 17, when the guidewire has been inserted through the septum and is disposed against a heart wall (with myocardium) or in the blood pool (without myocardium), at an insertion depth of 21.1 mm).

FIGS. 24A and 24B depict graphs of the temperature, as a function of time, of the electrosurgical devices of FIGS. 16 and 17 when the guidewire has been inserted through the septum and is at the heart wall (with myocardium) or in the blood pool (without myocardium), at an insertion depth of 21.1 mm. As noted above, the insertion depth reflects the distance that the guidewires of Devices 1 and 2 have been inserted past the top surface of the septum. FIG. 24A depicts the temperature at the myocardium and tip of the guidewires of Device 1 and Device 2 when they are contacting the myocardium. As seen in FIG. 24A, the temperature at the myocardium and the tip of the guidewire of Device 1 is less than the temperature at the myocardium and at the tip of the guidewire of Device 2. The lower temperature again reflects that Device 1 is better configured to dissipate heat. Thus, Device 1 is less likely to cause damage to the myocardium than Device 2. The heat dissipative effects of Device 1 can also be seen in FIG. 24B, which shows the temperature of the blood pool and the tip of the guidewire in the blood pool. As seen in FIG. 24B, both the temperature of the tip of the guidewire and the blood pool are greater in Device 2 than in Device 1, indicating that Device 1 is more capable of dissipating heat.

Figures 25A, 25B, 25C:
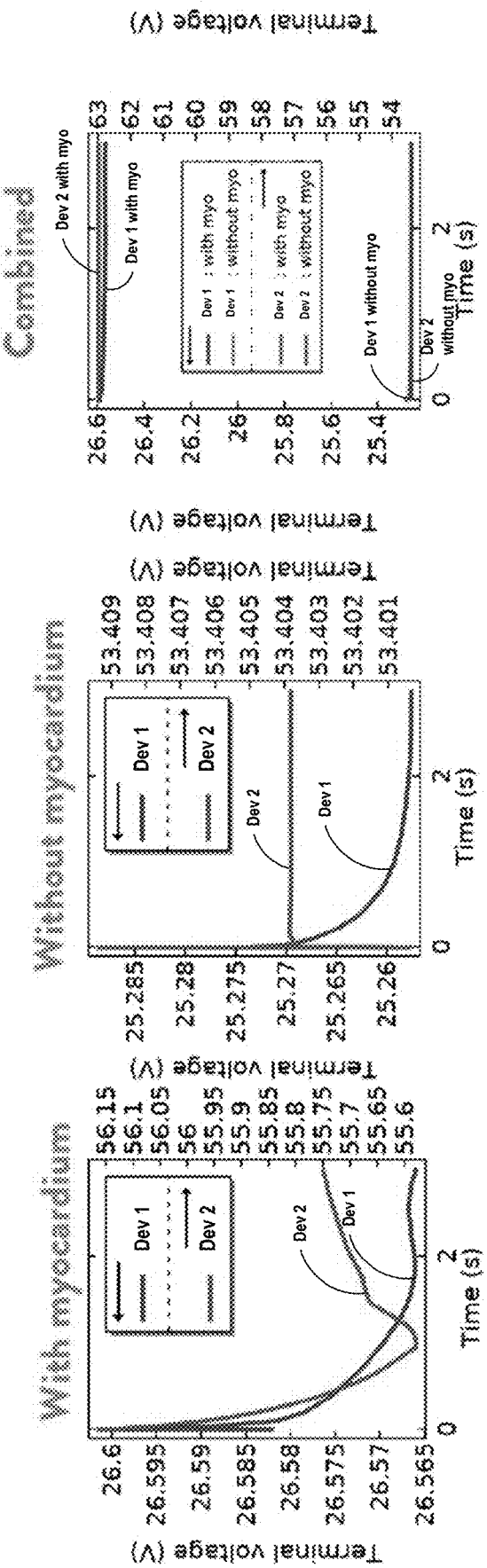
FIGS. 25A-25C are graphs of the terminal voltage of the electrosurgical devices of FIGS. 16 and 17, when the guidewire has been inserted through the septum and is disposed against a heart wall (with myocardium) or in the blood pool (without myocardium), at an insertion depth of 21.1 mm.
Figures 26A, 26B, 26C:
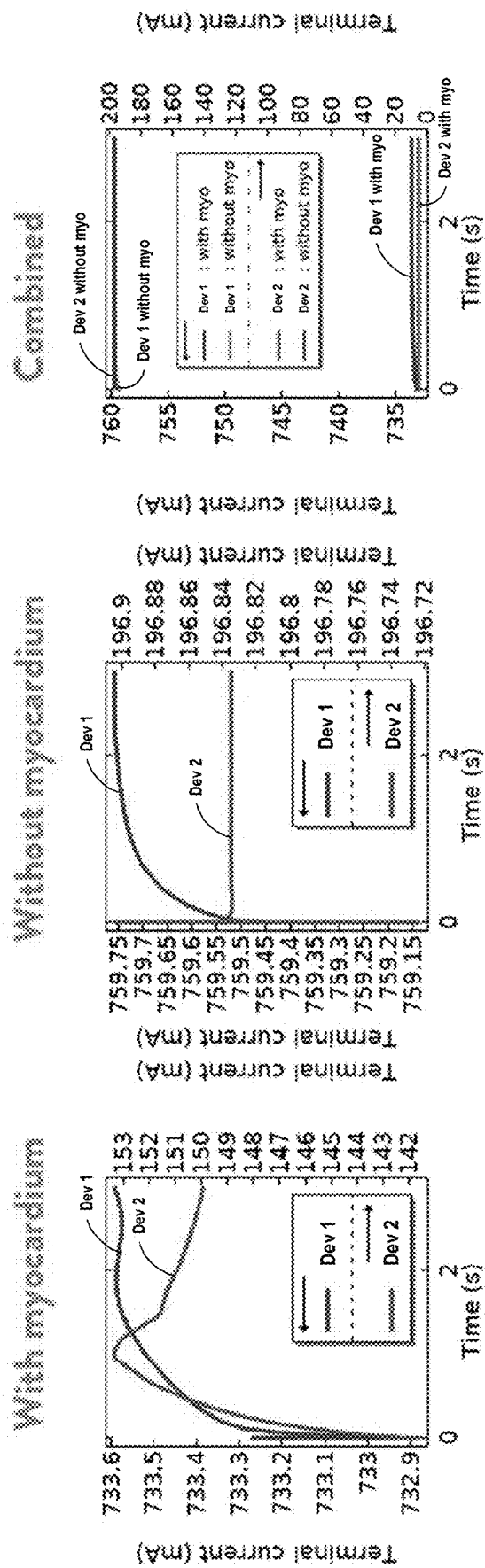
FIGS. 26A-26C are graphs of the terminal current of the electrosurgical devices of FIGS. 16 and 17, when the guidewire has been inserted through the septum and is disposed against a heart wall (with myocardium) or in the blood pool (without myocardium), at an insertion depth of 21.1 mm.
Figures 27A, 27B, 27C:
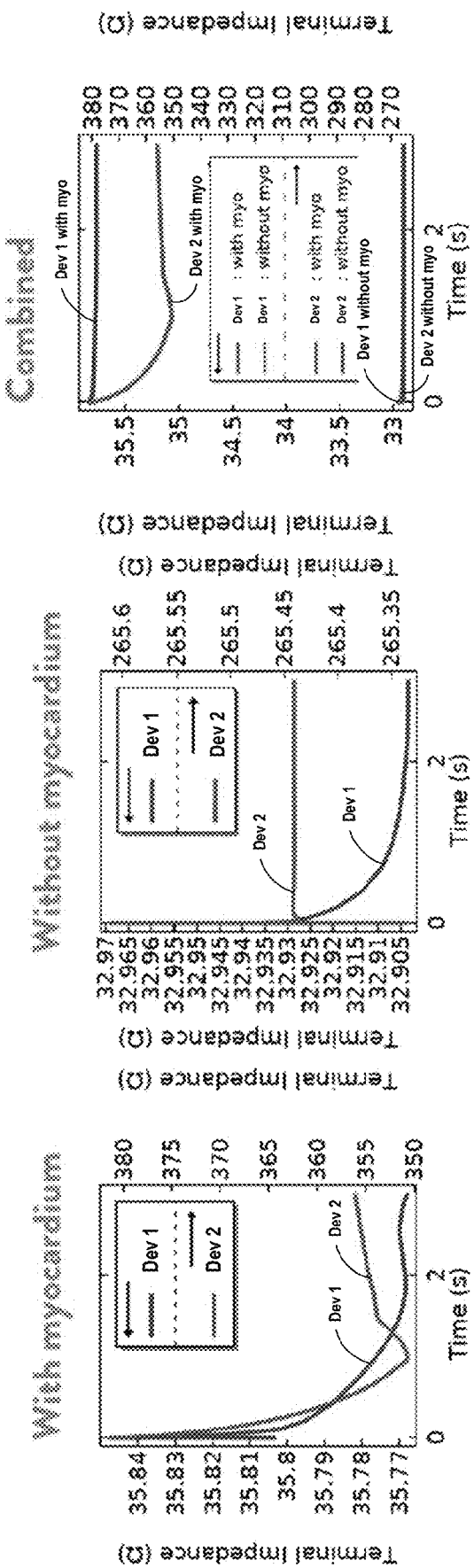
FIGS. 27A-27C are graphs of the terminal impedance of the electrosurgical devices of FIGS. 16 and 17, when the guidewire has been inserted through the septum and is disposed against a heart wall (with myocardium) or in the blood pool (without myocardium), at an insertion depth of 21.1 mm.

FIGS. 25A-25C depict graphs of the terminal voltage of the electrosurgical devices of FIGS. 16 and 17 when the guidewire has been inserted through the septum and is at a heart wall (with myocardium) or in the blood pool (without myocardium), at an insertion depth of 21.1 mm. FIGS. 26A-26C depict graphs of the terminal current of the electrosurgical devices of FIGS. 16 and 17 when the guidewire has been inserted through the septum and is at a heart wall (with myocardium) or in the blood pool (without myocardium), at an insertion depth of 21.1 mm. FIGS. 27A-27C depict graphs of the terminal impedance of the electrosurgical devices of FIGS. 16 and 17 when the guidewire has been inserted through the septum and is at a heart wall (with myocardium) or in the blood pool (without myocardium), at an insertion depth of 21.1 mm. As depicted in these figures, the terminal voltage at the tip of the guidewire of Device 1 is significantly lower than that of Device 2, and therefore is less likely to cause damage or injury to myocardium or other tissue surfaces. The impedance of the guidewire of Device 1 also generally stays lower than the impedance of the guidewire of Device 2, as more of a conductive region of the guidewire is exposed, allowing for charge to dissipate along a longer length of the guidewire.

In some embodiments, systems, devices, and methods can be configured to monitor impedance of a guidewire or energy delivery element, according to embodiments disclosed herein. As shown in FIGS. 23C and 27A-27C, the impedance of the guidewire drops once the guidewire is disposed in the blood pool or at the myocardium (heart wall). This drop in impedance is due to a greater exposed conductive surface area of the guidewire. As such, monitoring the drop in impedance (e.g., using a controller such as processor 114, as described above), can allow for the system to adjust the voltage being delivered, e.g., to avoid high current values and thereby avoid current leakages.

Figure 28A:
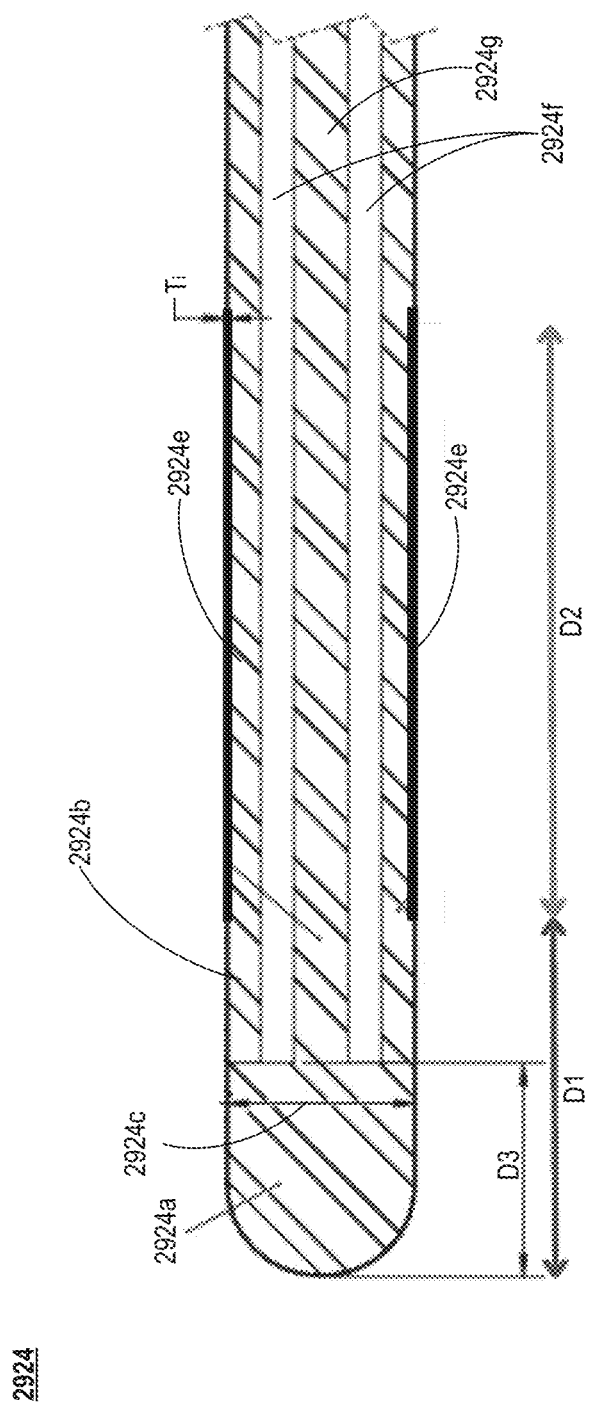
FIGS. 28A-28B are an example of a guidewire tip with an insulating collar, according to embodiments.
Figure 28B:
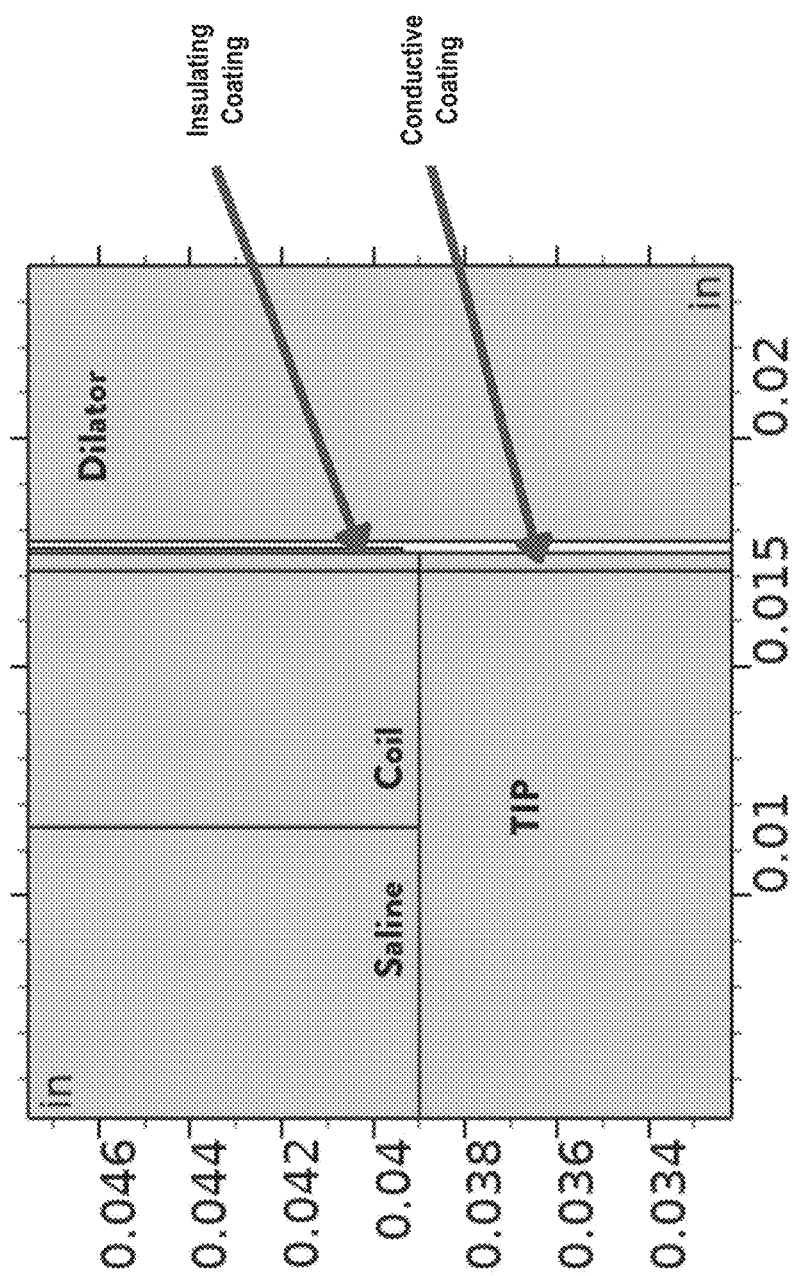

In some embodiments, electrosurgical devices described herein can include a guidewire with an insulating collar. FIGS. 28A-28B depicts a section view of an example guidewire 2924 (e.g., functionally and/or structurally similar to the energy delivery element 124 of FIG. 1) having a tip 2924a with an insulating collar 2924e, according to embodiments. The guidewire 2924 includes the tip 2924a, a coil 2924b, the insulating collar 2924e, a fluid 2924f, and core 2924g. In this embodiment, the guidewire 2924 is symmetric about a central axis and coated with an insulating coating proximal to the coil 2924b.

The tip 2924a is electrically coupled to the core 2924g, which is operatively connected to a generator, optionally via an electrosurgical interface, such as the electrosurgical interface 122 of FIG. 1. The core 2924g transfers energy to the tip 2924a so that the tip 2924a can engage and deliver energy to the tissue. The tip 2924a defines a tip width 2924c and a tip length D3. In some embodiments, the length D3 can be between about 0.5 to about 2 mm, including all sub-ranges and values therebetween. In some embodiments, the tip width 2924c is configured to fit into a sheath, such as the sheath 126 of FIG. 1 and to deliver a desirable amount of energy to the tissue. Proximal to the tip 2924a, the core 2924g is surrounded by a fluid 2924f. As seen in FIG. 28B, the fluid 2924f can include saline. During operation, the fluid can include a mixture of blood and saline. The fluid 2924f is surrounded by the coil 2924b. In some embodiments, the coil 2924b is formed of stainless steel. Additionally, as seen in FIG. 28B, the tip 2924a the coil 2924b can be coated with a conductive coating. In some embodiments, the conductive coating can include gold, tungsten, tantalum, and/or the like.

In some embodiments, a portion of the coil 2924b is covered with an insulating collar 2924e. The insulating collar 2924e is flush with the other portions of the coil 2924b. The insulating collar 2924e may be flush with the coil 2924b by compressing and/or elongating the coil 2924b, e.g., by being disposed over a stretched portion of the coil 2924b and/or the like. The insulating collar 2924e may begin along the coil 2924b a length D1 from the distal end of the guidewire 2924. In some embodiments, the length D1 can be between about 0.5 mm to about 3 mm from a distal end of the guidewire, including all sub-ranges and values therebetween, including, for example, between about 1 mm and about 2 mm. The insulating collar 2924e has a length D2. In some embodiments, the length D2 can be between about 2 mm and about 10 mm in length, including all sub-ranges and values therebetween, including, for example, between about 4 mm and about 6 mm. The collar 2924e can have a length that enables the current density at a distal end of the guidewire to remain high for a short distance (e.g., less than about 10 mm) necessary for ensuring penetration through the septum but to not be too long such that the current density at the distal end drops off as the guidewire is inserted beyond the septum and into the blood pool of the left atrium. In some embodiments, the insulating collar 2924e is formed of a polymer, ceramic, thermoplastic (e.g., PEBAC, Grilamid, PET, PTFE, FEP, PEEK, etc.). In some embodiments, the insulating collar 2924e may be applied via chemical vapor deposition (CVD). For example, CVD can be used to apply a diamond layer on the coil 2924b to form the insulting collar 2924e. In some embodiments, the insulating collar 2924e is configured to stiffen the distal end of the guidewire 2924. In some embodiments, the guidewire 2924 is stuff enough to provide about 0.1 to 5 Newtons of force for a puncture. The insulating collar 2924e defines a thickness Ti. Optionally, the thickness Ti can be constant across the entire portion of the coil 2924b covered by the insulating collar 2924e. In some embodiments, the thickness Ti is greater than a predefined minimum thickness, which corresponds to the thickness required to prevent dielectric breakdown. In some embodiments, the insulating collar can have a thickness that is desirable for providing a predetermined stiffness or flexibility of the guidewire 2924.

Figure 29:
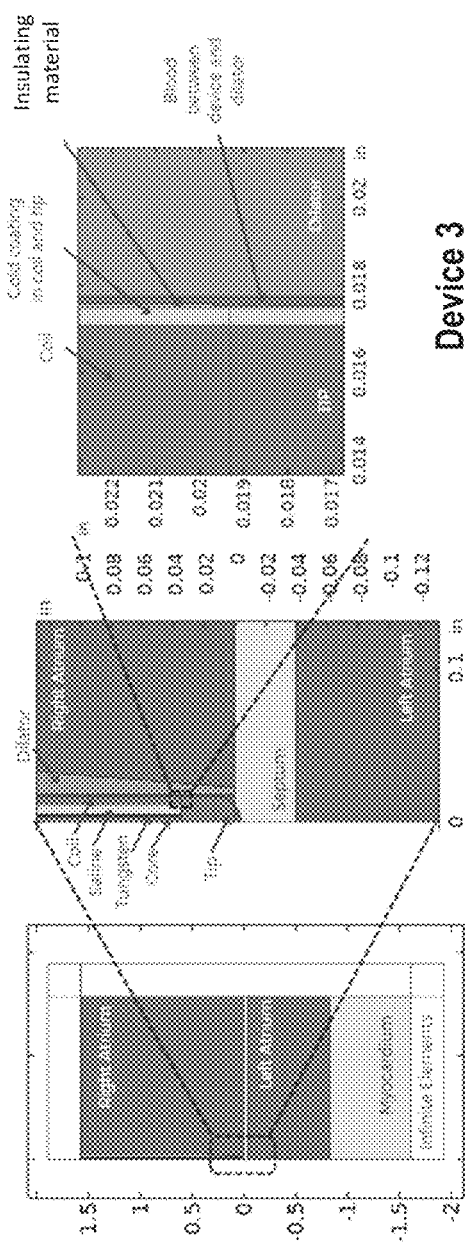
FIG. 29 schematically depicts an electrosurgical device including a guidewire and a dilator, where the guidewire has an insulating collar, according to embodiments.

FIG. 29 depicts an electrosurgical device (Device 3) engaging a septum, according to embodiments. Device 3 includes an insulating collar formed of an insulating material (e.g., 5 mm long PET collar) disposed on a portion of the guidewire of the device near the distal tip. The electrosurgical device of FIG. 29 may otherwise be similar to the electrosurgical device of FIG. 16. For example, the electrosurgical device of FIG. 29 can include a tip, a core, inner and outer coils (e.g., formed of tungsten), and a gold coating. In use, the energy delivery device can be flushed with a fluid, such as saline.

Device 1, as depicted in FIG. 16, and Device 3 are both examples of energy delivery elements or guidewires described herein, and therefore can be structurally and/or functionally similar to other energy delivery elements or guidewires described herein. Device 3 can operate similarly to Device 1 under most conditions, but due to the addition of the insulating collar, Device 3 may exhibit different operating behavior compared to Device 1 when the guidewires of the two devices are extended short distances out of a dilator. In particular, the guidewires of Device 1 and Device 3 may operate similarly to one another when the distance that each is extended out of a dilator are less than about 0.1 mm, 0.2 mm, 0.3 mm, 0.4 mm, or 0.5 mm, including any sub-ranges or values therebetween. When extended these minimal distances out of the dilator, the exposed conductive surface area of each guidewire may be small, and the current density of each device at the tip of the guidewire can be high and sufficient to puncture through tissue (e.g., the septum). However, when the guidewires are extended a further distance out of the dilator, the two devices may exhibit different behavior. In some embodiments, it may be desirable or necessary to extend a guidewire a further distance out of a sheath or dilator (e.g., if the dilator-tissue contact is not perpendicular). Device 1, which does not have an insulating collar, would have a conductive surface area that increases as a function of extension beyond the dilator more than that of Device 3, which has the insulating collar. As a consequence, the current density of Device 1 may decrease more than the current density of Device 3 at these initial short distances (e.g., less than about 10 mm, about 9 mm, about 8 mm, about 7 mm, about 6 mm, about 5 mm, about 4 mm, about 3 mm, or about 2 mm, including all sub-ranges and values therebetween. Therefore, for distances of between about 1 mm and about 10 mm, the insulating collar can help maintain current density at the tip of the guidewire of Device 3 at higher displacement values, thereby allowing Device 3 to remain capable of delivering sufficient energy to puncture through tissue (e.g., the septum). The following figures demonstrate these differences between Devices 1 and 3.

Figure 30A:
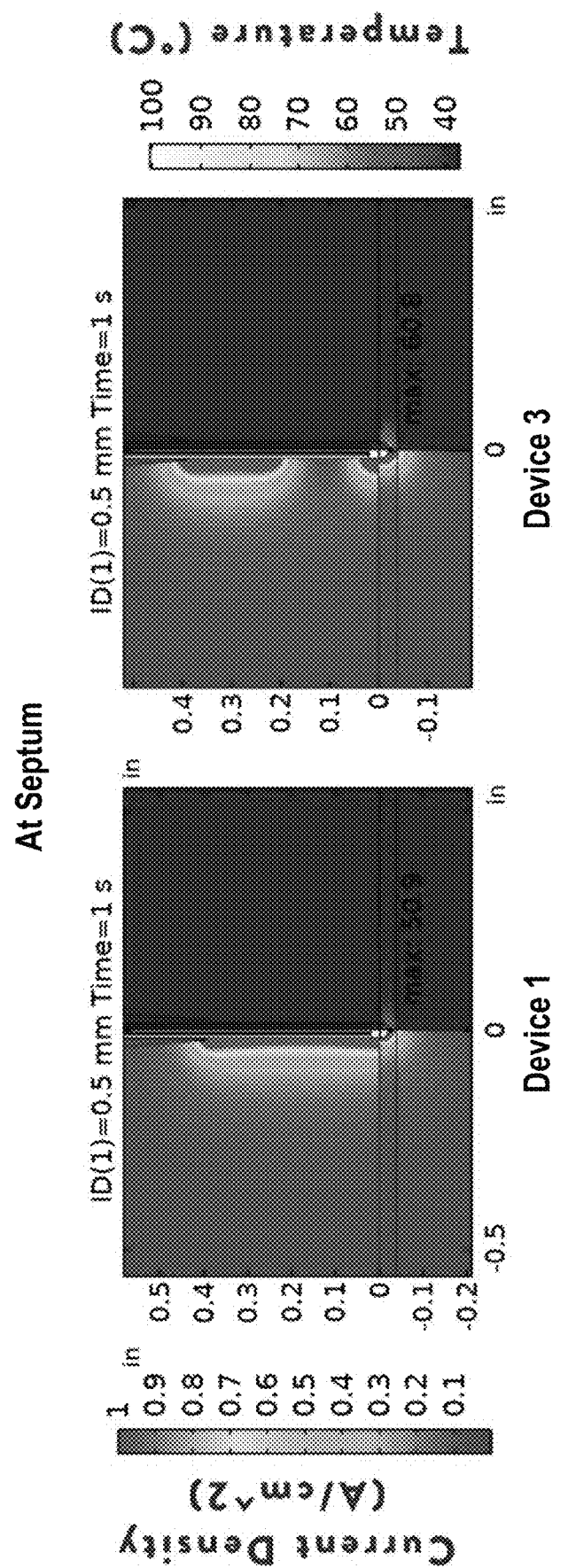
FIGS. 30A-30C depict the current density and temperature around the electrosurgical devices of FIGS. 16 and 29, when the guidewire is at the septum, at the heart wall, and in the blood pool, respectively.
Figure 30B:
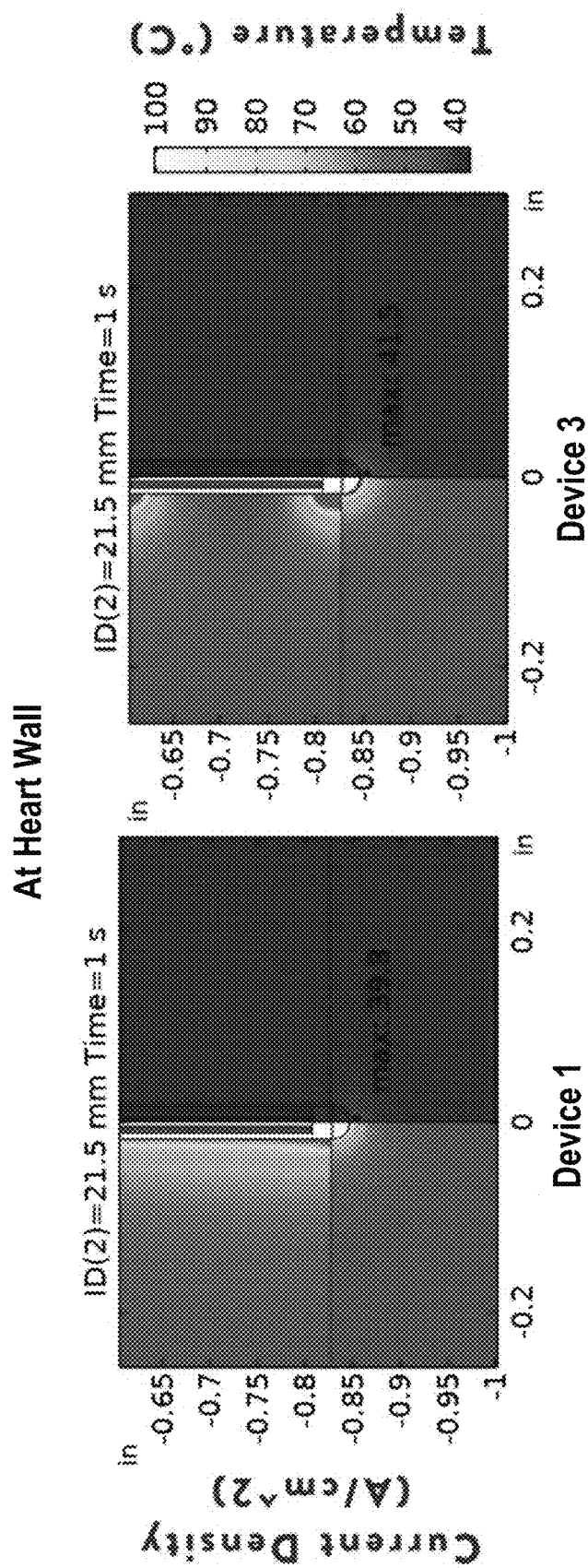
Figure 30C:
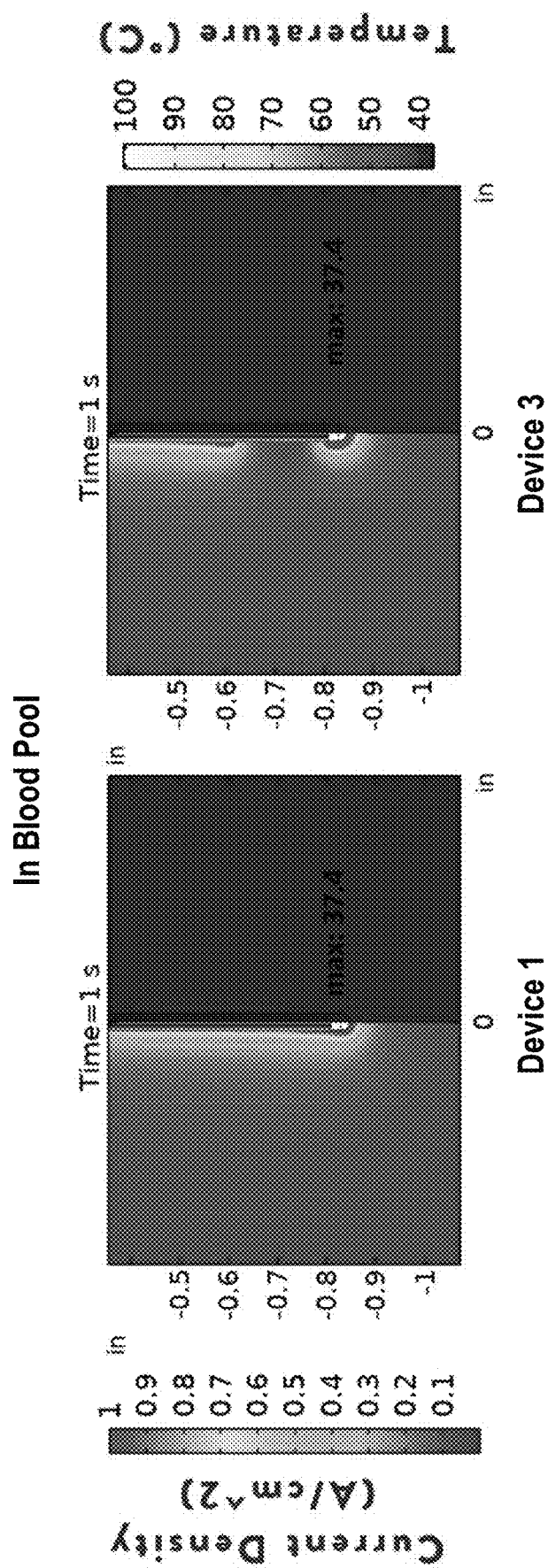

FIGS. 30A-30C and 39-41B provide a comparison of the operation of Device 1 and the operation of Device 3, under simulated conditions. The simulated conditions are used to demonstrate the differences in operation of the guidewires of Devices 1 and 3. FIG. 30A depicts the behavior of the two devices when the guidewire is at the septum and the guidewire has been extended a short distance out of the dilator (e.g., about 0.4 ins or about 10 mm). For illustration purposes, the short distance that the two guidewires are extended out of the dilator has been intentionally set to fully expose the collar along with one or more conductive portions of the guidewires. FIG. 30B depicts the behavior of the two devices when the guidewire is at a heart wall and the guidewire has been extended a longer distance out of the dilator compared to FIG. 30A. And FIG. 30C depicts the behavior of the two devices when the guidewire is in the blood pool and has also been extended a longer distance out of the dilator compared to FIG. 30A.

As seen in FIG. 30A, when the guidewire of Device 1 has been extended about 10 mm out of the dilator, the current density has been distributed across the length of the guidewire and therefore the energy at the tip has fallen to lower values. In contrast, when the guidewire of Device 3 has been extended about 10 mm out of the dilator (e.g., sufficient to expose the insulating collar), it has higher current density at the tip due to the insulating collar. The insulating collar can prevent current from dissipating in the portion of the guidewire it is covering, and therefore reduce the drop off of current density at the tip as the guidewire is extended out of the dilator. This can help prevent the guidewire from losing too much energy at its tip as it is extended out of the dilator, at least for short distances. Therefore, the tip of the guidewire can be effective at puncturing through the septum up until it has been extended a certain distance out of the dilator. This distance can less than about 10 mm, less than about 15 mm, or less than about 20 mm, inclusive of all sub-ranges and values therebetween. This can allow Device 3 to be configured to puncture through the septum in a larger range of distances that the guidewire is extended. After penetrating through the septum, the higher current densities of Device 3 then decrease as well, which decreases the likelihood of a lesion formed by accident. As a result of the collar, the maximum temperature of Device 3 (60.8° C.) is slightly higher than the maximum temperature of Device 1 (50.9° C.); however, this increase in temperature does not affect the operation of the device. The temperatures of both guidewires are still below temperatures that would lead to undesirable outcomes such as coagulum or char.

Figure 39:
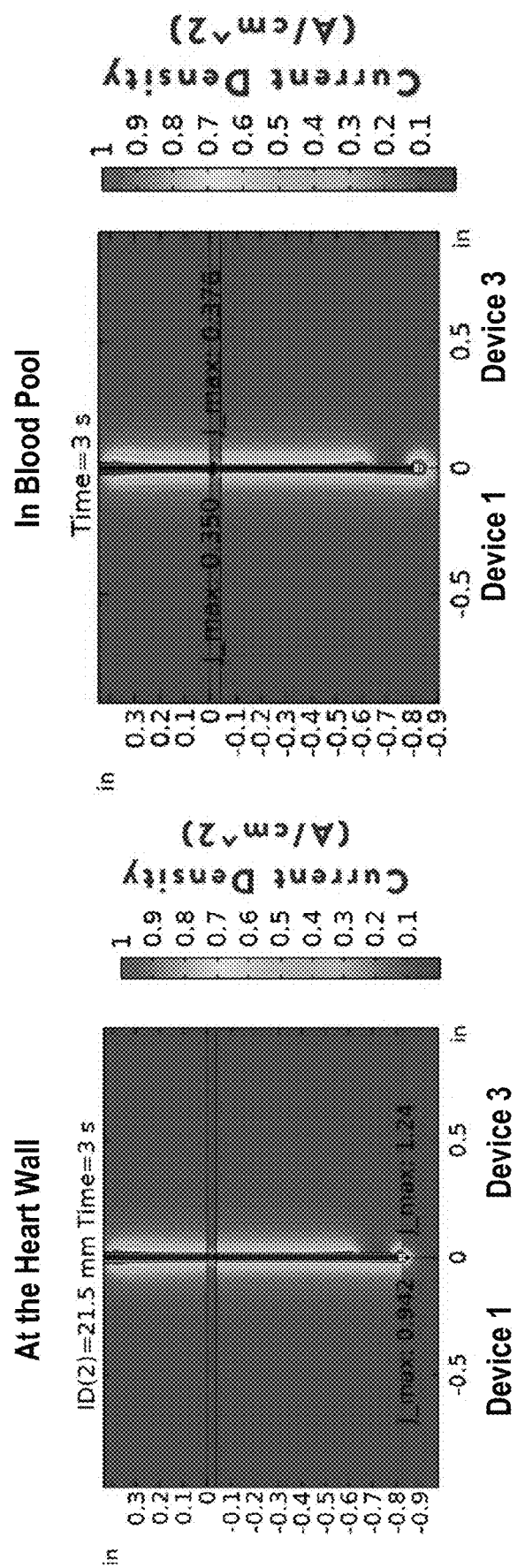
FIG. 39 depicts the current density around the electrosurgical devices of FIGS. 16 and 29 when the dilator is retracted when the electrosurgical devices are at the heart wall and in the blood pool.

When the guidewire of Device 3 has been extended further out of the dilator, e.g., when at the heart wall or in the blood pool beyond the septum, as shown in FIGS. 30B and 30C, the current density at the tip of the guidewire has also decreased, similar to that of Device 1. In other words, similar to the guidewire of Device 1, as the guidewire of Device 3 is extended further out of the dilator, the conductive surface area of the guidewire increases sufficiently that the current density of the guidewire also decreases at the tip to levels that are unlikely to cause a lesion at the heart wall. Therefore, Devices 1 and 3 operate similar to one another when their guidewires are extended past the septum and longer conductive surface areas of the guidewires are exposed. As shown in FIGS. 30B-30C, the temperature profile of the two guidewires can be similar at the heart wall or in the blood pool. In particular, the maximum temperature of Device 1 is 39.8° C. at the heart wall and the maximum temperature of Device 3 is 41.5° C. at the heart wall. The maximum temperature of Device 1 is 37.4° C. in the blood pool and the maximum temperature of Device 3 is 37.4° C. in the blood pool. As shown in FIG. 39, the maximum current density of Device 3 has also decreased, though remaining higher than those of Device 1. At the heart wall, the maximum current density of Device 1 is 3.52 A/cm² and the maximum current density of Device 3 is 49.8 A/cm². In the blood pool, the maximum current density of Device 1 is 3.40 A/cm² and the maximum current density of Device 3 is 61.1 A/cm².

Referring generally to FIGS. 31A-33, various embodiments of disposing insulating collars, or the like, are shown. The insulating collars may be functionally similar to the insulating collars of FIGS. 28A-29 or may be used to form an insulating collar similar to the insulating collars of FIG. 28A-29. The insulating collars of FIGS. 31A-33 can be used with a guidewire, such as, for example, the energy delivery element of FIG. 1 or any other guidewires described herein.

Figure 31A:
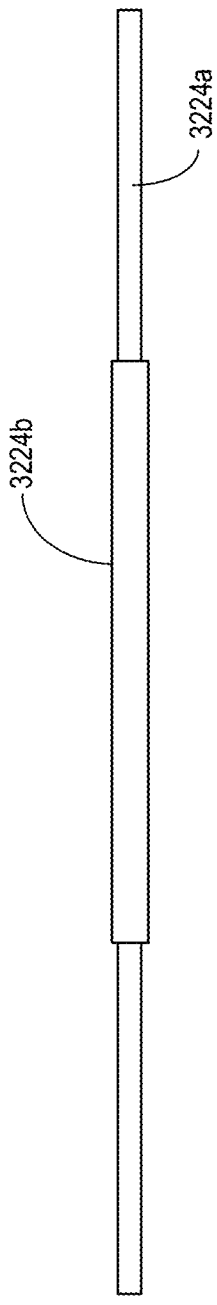
FIG. 31A depicts an example of an insulating collar over a coil wire, according to embodiments.
Figure 31B:
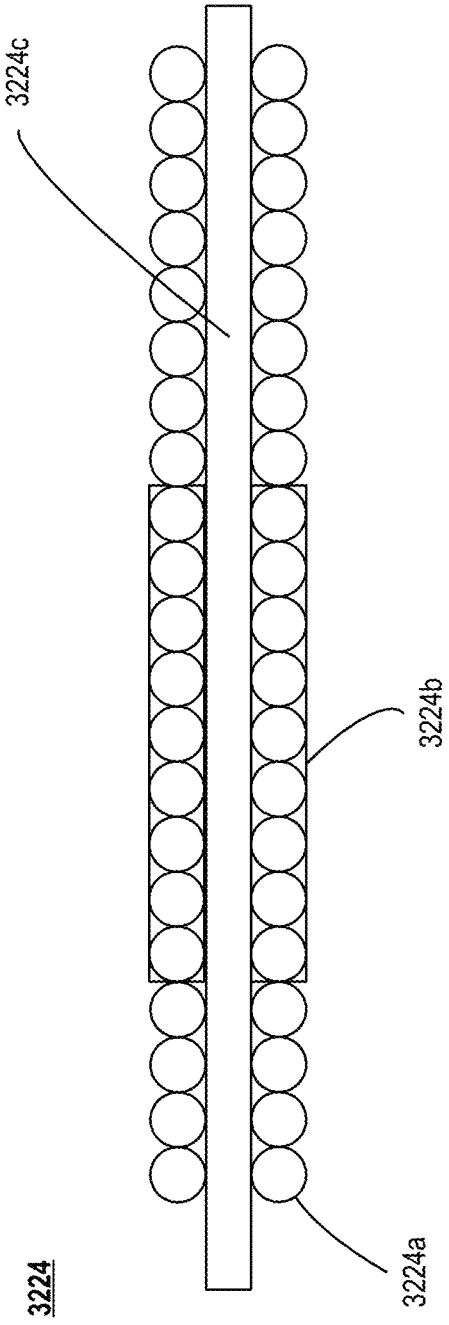
FIG. 31B depicts an example of an insulating collar over a coil, according to embodiments.
Figure 32:
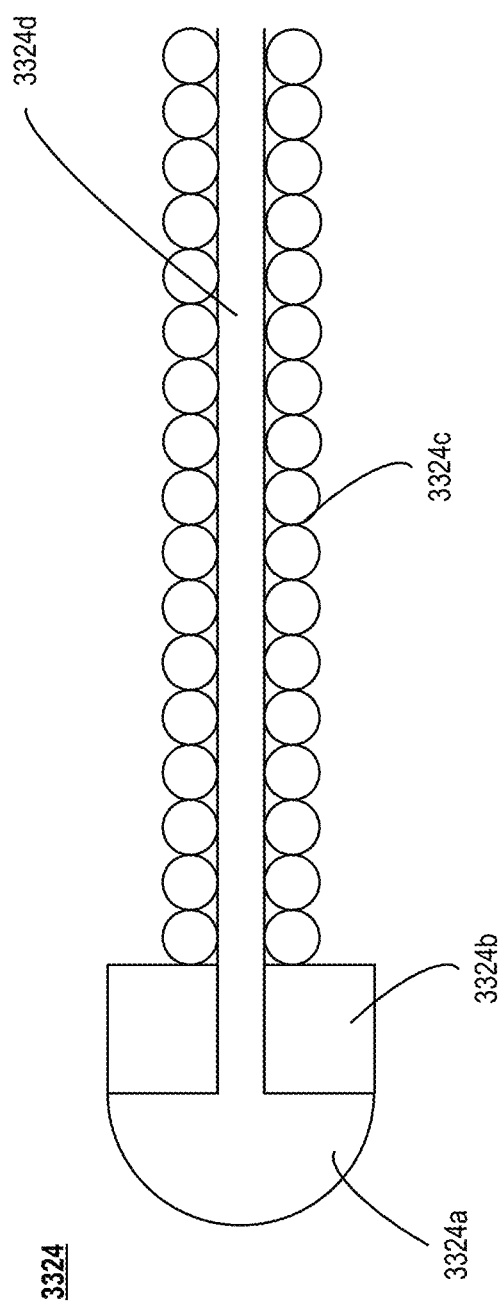
FIG. 32 depicts an example of an insulating collar on a guidewire, according to embodiments.
Figure 33:
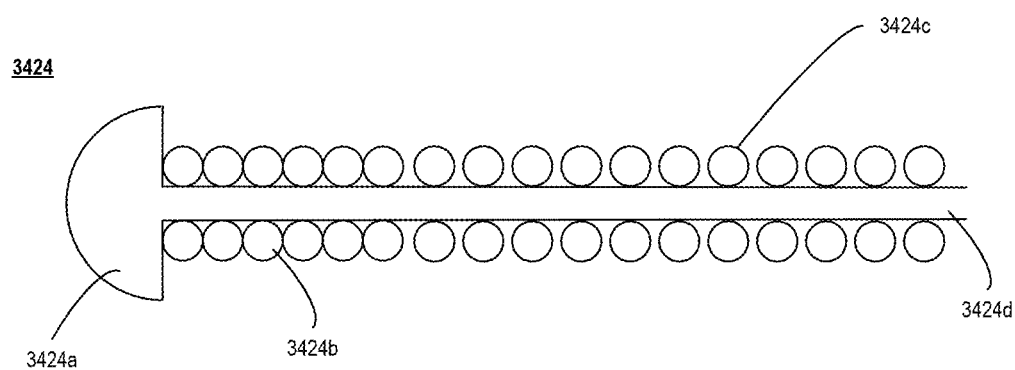
FIG. 33 depicts an example of an insulating coil on a guidewire, according to embodiments.

FIG. 31A depicts an example of forming an insulating collar by first adding an insulative region 3224*b* to a coil wire 3224*a*. After the insulative region 3224*b* is on the coil wire 3224*a*, the coil wire 3224*a* can be coiled around a core of a guidewire, or around a mandrel, to form a coil. Forming the coil can be seen in FIG. 31B where the coil wire 3224*a* is coiled around a mandrel 3224*c* to form the coil. The coil can then be placed over and welded to the core of a guidewire. The resulting insulative region, as shown in FIG. 31B, can function as the insulating collar of the guidewire. FIG. 32 depicts an example of an insulating collar 3324*b* on a guidewire 3324, according to embodiments. The insulating collar 3324*b* of FIG. 32 is a solid portion (e.g., a solid ring) adjacent to the tip 3324*a* of the guidewire 3324. The insulating collar 3324*b* can be disposed over a core 3324*d* of the guidewire, which is coupled to the tip 3324*a*. The insulating collar 3324*b* can be coupled to a coil 3324*c* at its proximal end. In some embodiments, the coil 324*c* is welded, adhered, and/or the like, to the insulating collar 3324*b*. FIG. 33 depicts an example of an insulating collar implemented as a coil 3424*b* on a guidewire 3424, according to embodiments. The coil 3424*b* can be a coil formed of an insulative material or less conductive material, which is coiled around the core 3424*d*. The coil 3424*b* is located between a conductive coil 3424*c* and the tip 3424*a* and provides the guidewire 3424 with an insulative portion proximal to the tip 3424*a*.

Figure 34:
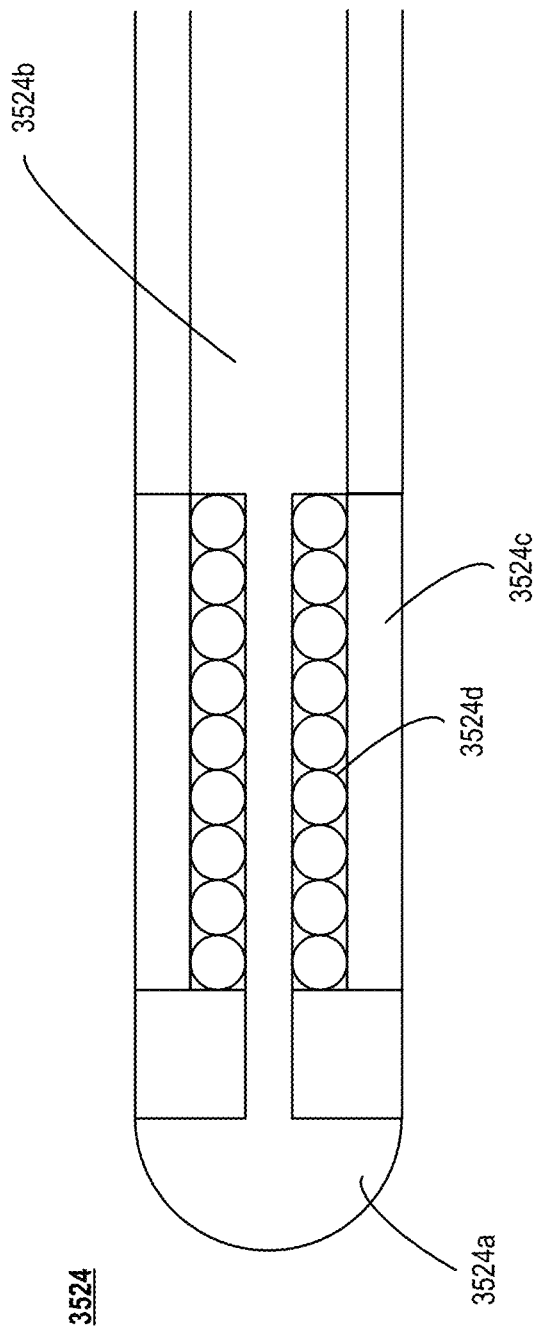
FIG. 34 depicts an example of a guidewire tip with an insulating collar, according to embodiments.

FIG. 34 depicts another example of a guidewire 3524 with an insulating collar 3524*c*, according to embodiments. The guidewire 3524 can be structurally and/or functionally similar to other energy delivery elements and/or guidewires described herein. The insulating collar 3524*c* can have a length of between about 1 mm and about 20 mm, including all values and sub-ranges therebetween. As described above with respect to FIG. 28A, it can be desirable to have an insulating collar of a guidewire to be flush (or substantially flush) with an outer surface of the guidewire. This can ensure that the surface of the guidewire does not have any edges or features that may create unintentional snagging or engagement with other structures. In some embodiments, to provide for a flush outer surface for the guidewire, the collar may be disposed over a section of the guidewire where there is a step down in thickness of the core wire (or other internal components). For example, as depicted in FIG. 34, a collar 3524*c* may be disposed over a region of the guidewire where the core wire 3524*b* has a smaller diameter. Optionally, this region may also have a coil 3524*d* that is disposed over the core wire, which may also be compressible to further allow the collar to sit flush with an outer surface of the guidewire. The guidewire, similar to other guidewires described herein, can also include a tip 3524*a*.

In some embodiments, guidewires as described herein include thermally conductive portions. As described above, the use of a RF powered guidewire or needle to create an atrial-septal defect, e.g., for transseptal access, can cause thromboembolic risk by generating inadvertent char and/or coagulum. Char and coagulum may result when tissue temperatures are above a threshold which causes protein denaturation, dehydration, and/or thrombogenic cascade. Therefore, maintaining a guidewire tip temperature below a predefined threshold can prevent or reduce the risk of forming char and coagulum, thereby avoiding thromboembolic risk to a patient.

Figure 35:
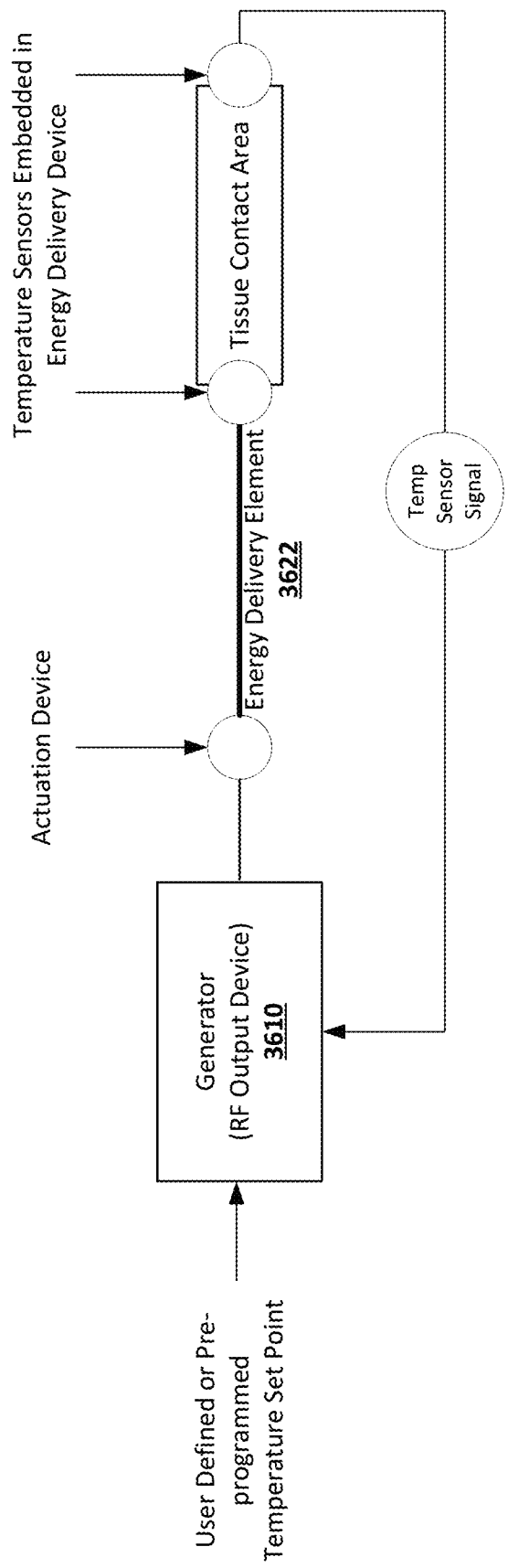
FIG. 35 is a schematic representation of implementing temperature control at a tip of an energy delivery device, according to embodiments.

FIG. 35 depicts a schematic representation of implementing temperature control with the energy delivery elements and guidewires described here, according to embodiments. As depicted, a generator 3610 (e.g., structurally and/or functionally similar to other generators described herein) is coupled to an energy delivery device 3622. A physician can actuate an actuation device (e.g., structurally and/or functionally similar to other actuators or actuation devices described herein) to cause an RF output to be delivered to the energy delivery element 3622. The energy delivery element 3622 can be structurally and/or functionally similar to other energy delivery elements and/or guidewires described herein. In an embodiment, the energy delivery element 3622 can be a guidewire. One or more temperature sensors (e.g., thermistor, thermocouple, etc.) can be coupled to or embedded in the energy delivery device near an expected tissue contact area, e.g., to monitor temperatures at the tissue contact area. The temperature sensor signal(s) can then be sent to the generator 3610, which can be configured to modulate or control the RF output based on the temperature feedback. In some embodiments, the generator 3610 can be configured to deliver RF output to reach a target set point temperature or range. The target set point temperature or range can be between about 55 and about 80 degrees Celsius, including all values and sub-ranges therebetween. By avoiding temperatures above 80° Celsius, the incidence of char and coagulum formation can be reduced.

In some embodiments, a guidewire can include thermally conductive materials that can be configured to wick or pull heat away from a tip of a guidewire. Existing guidewires can include irrigated guidewires, which can directly cool an electrode and nearby tissue. However, in some instances, coagulum can still form on electrodes of irrigated guidewires, particularly near the boundary between an electrode and a polymer insulation proximal of the tip, e.g., where the heat from the tip may be trapped by the poor heat transfer of the polymer. Currently, existing guidewires for transseptal access do not include irrigation. Energy delivery devices or guidewires as described herein can provide for cooling via larger tip electrodes. This is because the uninsulated, longer active electrode region (e.g., greater than about 1 cm, 2 cm, etc.) can wick or pull heat away from the tip of the guidewire, in contrast to other guidewires that may include plastics or insulating materials that prevent heat transfer. As described above, however, it may be desirable to have certain portions of the active electrode be covered with electrical insulation, thereby maintaining RF current density across a range of use conditions (e.g., if the dilator-tissue contact is not perpendicular). In such embodiments, an insulating collar may be used to cover a portion of the active electrode or conducting outer surface of the guidewire, e.g., as described with reference to FIGS. 29-34 and 40-42C. The collar can be formed of thermally conductive material such that the collar does not prevent or reduce heat transfer away from the tip and increase the risk of char or coagulum.

Figure 40:
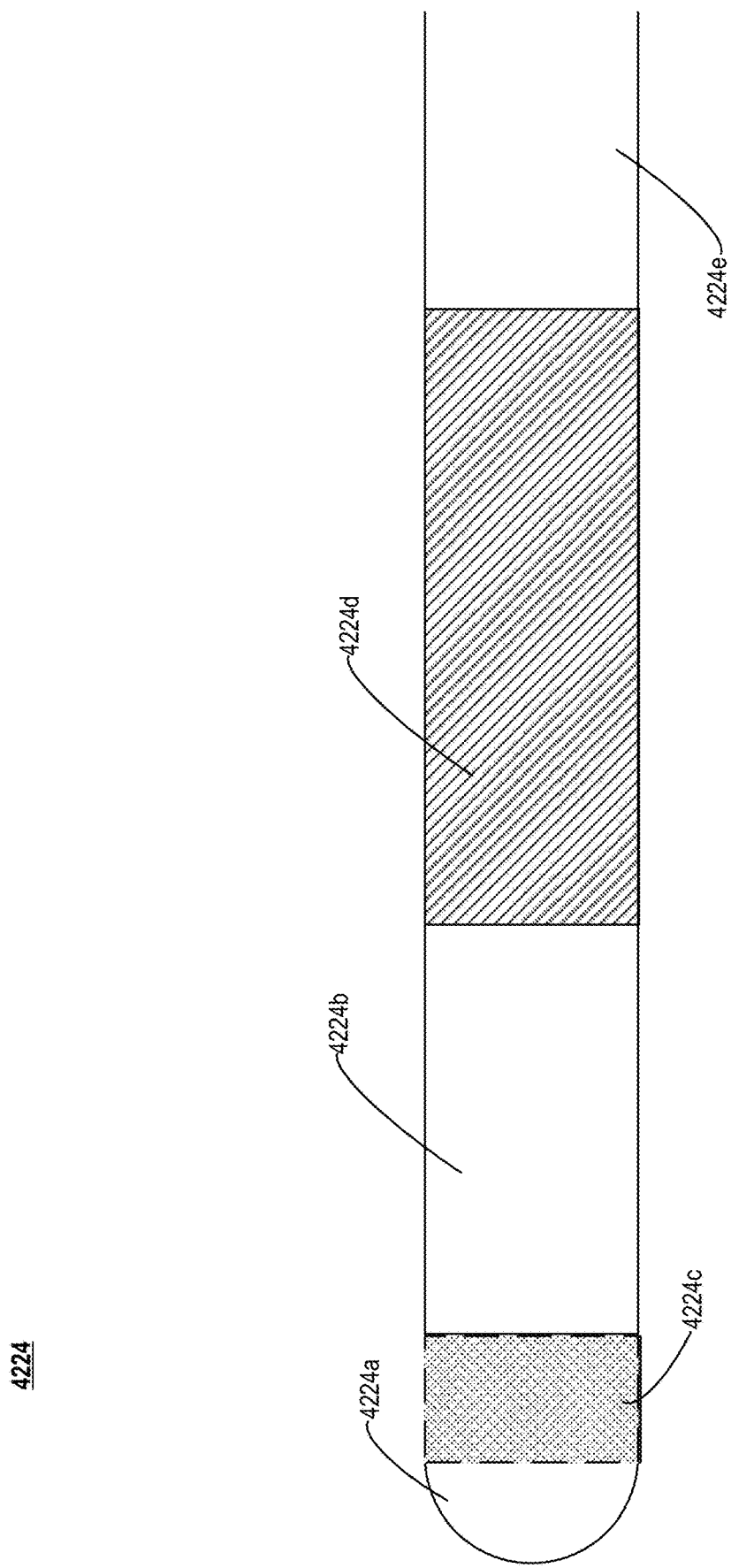
FIG. 40 depicts an example of a guidewire tip with a marker band, according to embodiments.

FIG. 40 depicts a tip of a guidewire 4224 including a thermally conductive portion, according to embodiments. The guidewire 4224 can be structurally and/or functionally similar to other guidewires described herein, including, for example, the energy delivery element 124 of FIG. 1. For example, the guidewire 4224 can include a tip 4224a, a thermally conductive portion 4224b, an electrically conductive portion 4224d, and a standard insulated portion 4224e.

The tip 4224a is formed of a solid metal (e.g., stainless steel, etc.) configured to deliver energy for puncturing through the septum. The tip 4224a can have a length of between about 0.1 mm and about 1 mm, including all values and sub-ranges therebetween, including, for example, about 0.5 mm. In some embodiments, the tip can be an electrically conductive portion that is between about 0.25 mm and 30 cm in length. The thermally conductive portion 4224b can be adjacent to and proximal of the tip 4224a. In some embodiments, the thermally conductive portion 4224b can be implemented as an electrically insulating collar, similar to other insulating collars described herein (e.g., collar/PET coating in Device 3, collar 3524b). The location of the thermally conductive but electrically insulative portion 4224b can allow for current density to be focused at the tip 4224a. The thermally conductive portion 4224b can be formed of a thermally conductive polymer or metal (e.g., tungsten, tantalum, platinum, gold, etc.). In some embodiments, the thermally conductive portion 4224b can be configured to provide heat transfer and electrical insulation, so as to avoid increasing the outer conductive surface area of the guidewire. As such, materials such as platinum and gold, which would increase the conductive surface area of the electrode, may be less desirable. In some embodiments, the thermally conductive portion 4224b (e.g., or an electrically insulating region) can be between about 2 mm and about 2 cm in length.

In some embodiments, the guidewire 4224 can optionally include a marker band 4224c. In such embodiments, the marker band 4224c can be adjacent to and proximal of the tip 4224a. The marker band 4224c can be implemented as a coating on the thermally conductive portion 4224b. Alternatively, the marker band 4224c can be a separate element or component from the thermally conductive portion 4224b. The marker band 4224c is formed of a material that allows for the marker band 4224c to be visible during imaging, e.g., a radiopaque material visible with fluoroscopy. The marker band 4224c can be formed of a thermally conductive material, e.g., to allow for heat transfer from the tip 4224a. In some embodiments, the marker band 4224c can be implemented with a diamond coating, which allows for heat to dissipate while being an electrical insulator. The diamond coating can be disposed on a band that is made of radiopaque material, such as platinum, tantalum, or tungsten.

The electrically conductive portion 4224d is proximal to the thermally conductive portion 4224b. The electrically conductive portion 4224d can include a conductive outer surface. In some embodiments, the electrically conductive portion 4224d may include one or more features (e.g., cutouts, holes, slots) that allow for the electrically conductive portion 4224d to have a conductive outer surface. For example, the electrically conductive portion 4224d may include features as described in reference to FIGS. 11A and 11B. Alternatively, or additionally, the electrically conductive portion 4224d can include electrically conductive polymer coating. The electrically conductive portion 4224d allows for current to be distributed along a portion of the length of the guidewire 4224, e.g., by providing a larger active electrode region. The standard portion 4224e is a portion formed of an electrically insulating material (e.g., a polymer) that is configured to insulate and protect the guidewire 4224. In some embodiments, the electrically conductive portion 4224d is between about 5 mm and about 30 cm in length.

The configuration of the guidewire 4224 allows for the operational power of the guidewire 4224 to be lower than known systems as the marker band 4224a and the thermally conductive portion 4224b allow for the current density to be focused at the tip 4224a during operation, and the electrically conductive portion 4224d allows for the current density to dissipate along the length of the guidewire 4224 after the tip 4224a has engaged and punctured the septum and the electrically conductive portion 4224d has been exposed. In some embodiments, the operational power is between about 10 Watts to about 40 Watts, including all sub-ranges and values therebetween. In some embodiments, the operational power is between about 10 Watts to about 25 Watts.

Figure 41:
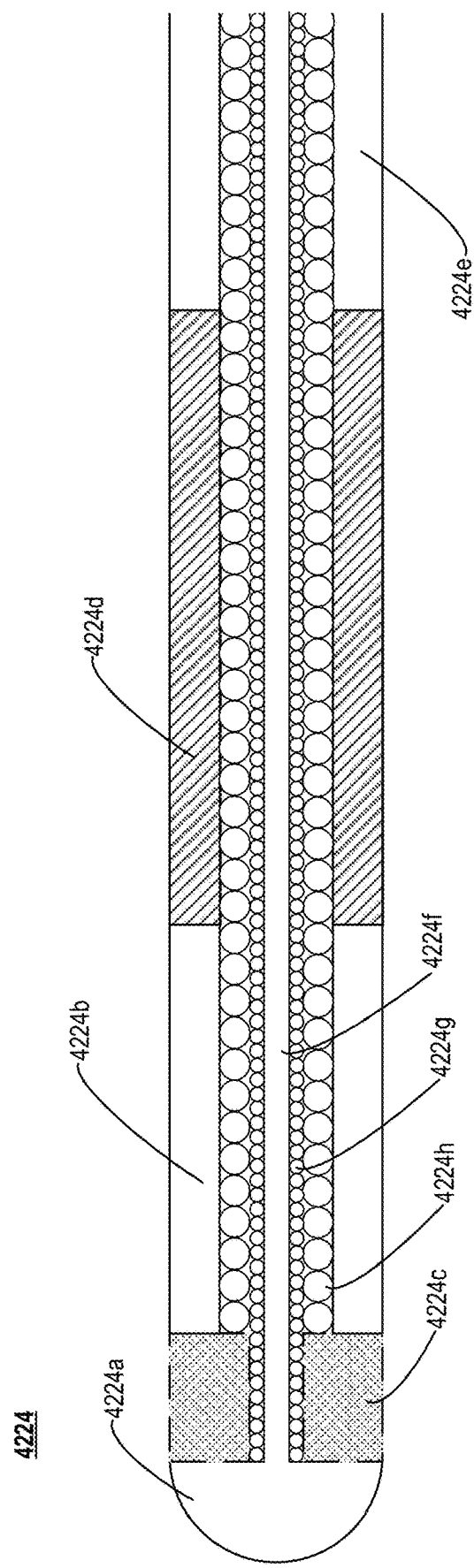
FIG. 41 depicts a sectional view of the guidewire of FIG. 40.

FIG. 41 depicts a cross-section view of the guidewire 4224, in accordance with an embodiment. As seen in FIG. 41, the inside of the guidewire 4224 includes a core 4224f, an inner coil 4224g surrounding the core 4224f, and an outer coil 4224h surrounding the inner coil 4224g. The core 4224f is contiguous with (e.g., bonded with) the tip 4224a. The inner coil 4224g wraps around the core and terminates at the tip 4224a. The outer coil extends along the guidewire 4224 up to the marker band 4224b. The inner and outer coils can provide support while allowing for flexibility of the guidewire. In some embodiments, the outer coil 4224h is coated. In some embodiments, the coating is a polymer. In some embodiments, the coating is gold, e.g., for heat transfer. In some embodiments, the diameter or size of the wire used to form the outer coil 4224h are greater than the diameter or size of the wire used to form the inner coil 4224g.

Figure 42A:
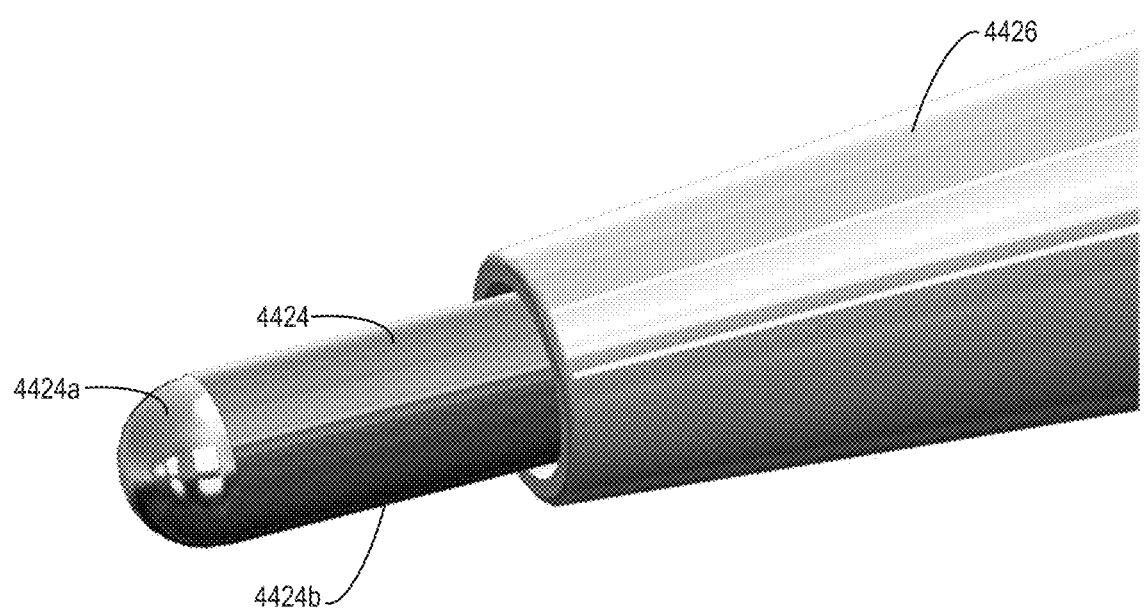
FIGS. 42A-42C depict perspective views of a guidewire, according to embodiments.
Figure 42B:
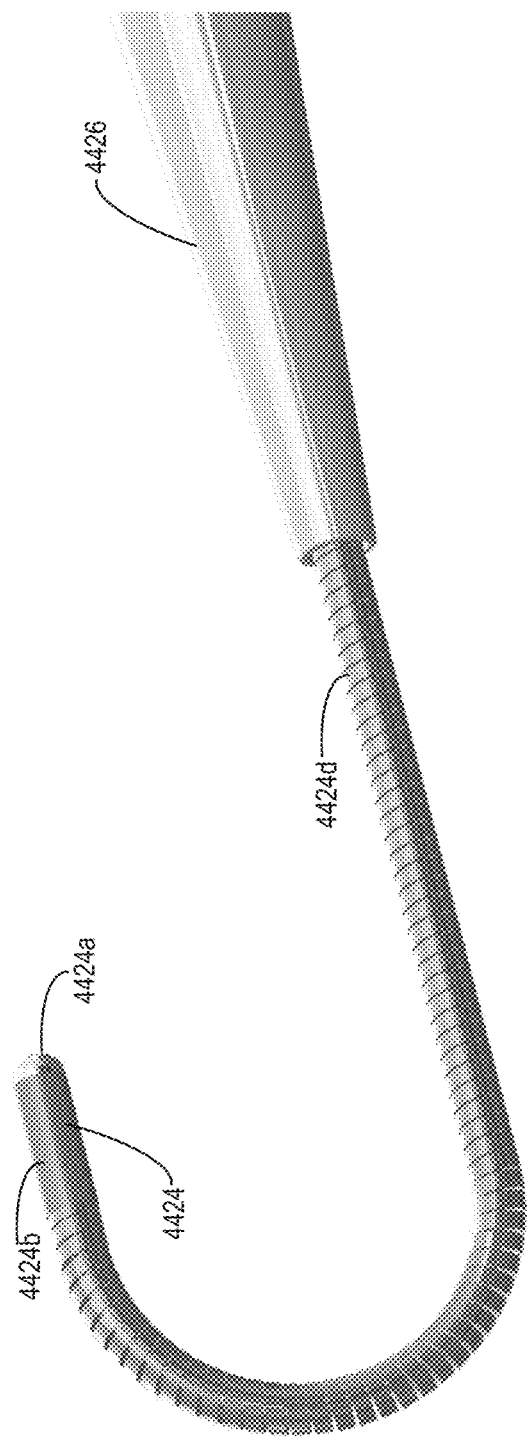
Figure 42C:
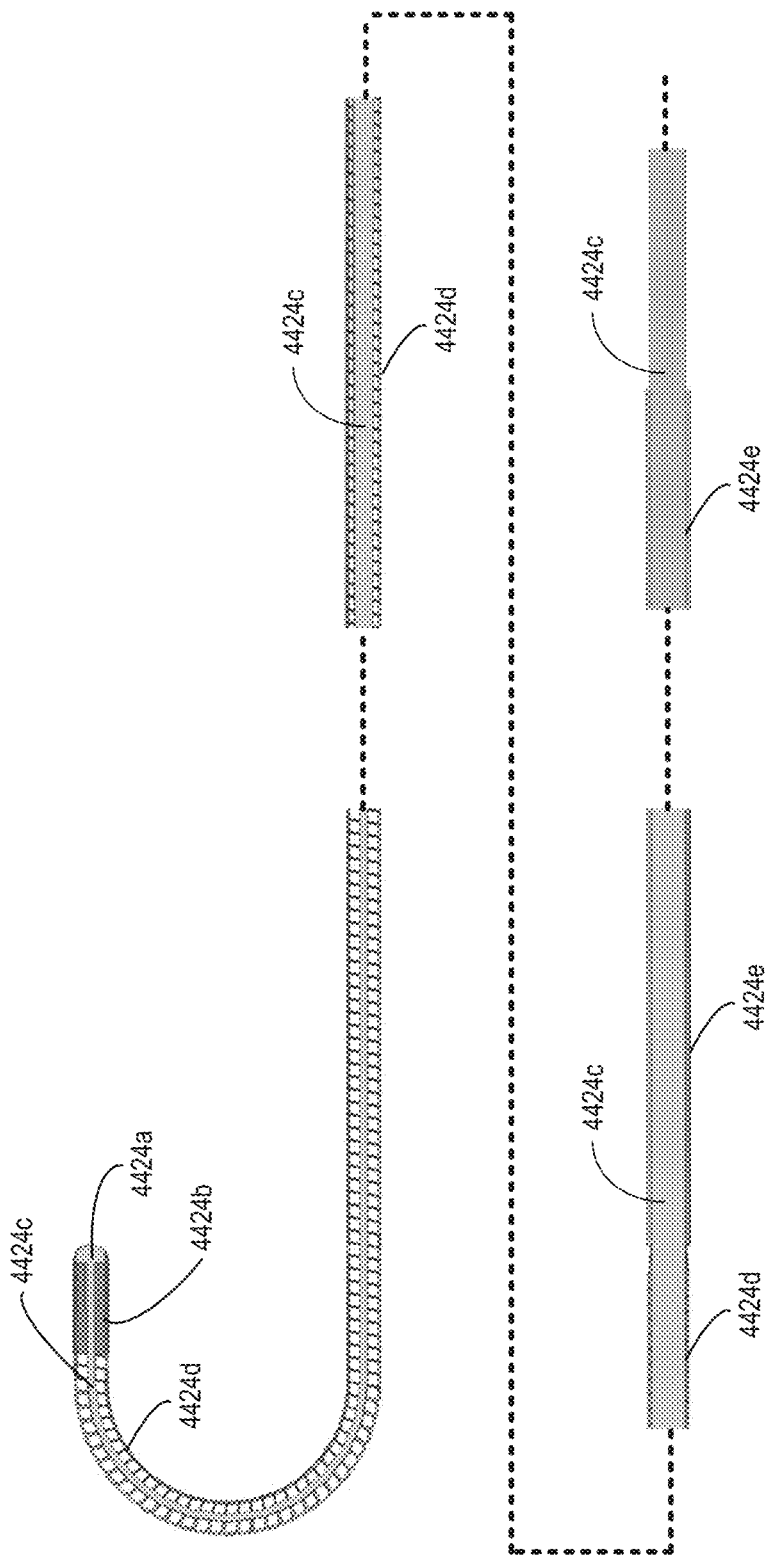

FIGS. 42A-42C depict yet another example of a guidewire 4424, according to embodiments. The guidewire 4424 can be structurally and/or functionally similar to other energy delivery elements or guidewires described herein, including, for example, energy delivery element 124, guidewire 624, 724, 924, 4224, etc. As such, the guidewire 4424 can include components that are similar to those components of other guidewires described herein. For example, the guidewire 4424 can include a tip 4424a, a collar 4424b, and an electrically conductive portion 4424d. The guidewire 4424 is configured to be disposed within a dilator or sheath 4426, which can be functionally and/or structurally similar to other dilators and/or sheaths described herein (e.g., sheath 126, 426, 626, 726, etc.).

FIG. 42A depicts the guidewire extended a short distance out of an outer sheath or dilator 4426. For example, the guidewire can be extended a distance of between about 0.5 mm and about 15 mm, including all values and sub-ranges therebetween. As described above, e.g., with reference to FIG. 8B, the guidewire can be extended a short distance out of a dilator 4426 to expose the conductive tip 4424a of the guidewire. The conductive tip 4424a can then be used to deliver energy to perforate through tissue. When extended these short distances out of the dilator 4426, the guidewire has a small conductive surface area that is exposed. This small conductive surface area can allow current density to be concentrate at the tip 4424a of the guidewire, thereby enabling the tip to generate sufficient energy to perforate through a tissue wall, such as, for example, a septum. As described above, in some embodiments, the guidewire can have a collar 4424b, which can be formed of an insulative material or a material having low electrical conductivity.

The collar 4424b can be disposed adjacent to the tip 4424a of the guidewire, such that the conductive surface area of the guidewire exposed beyond the dilator 4426 does not increase or remains the same (or substantially the same) as the guidewire is extended these short distances outside of the dilator 4426. This can ensure that the current density at the tip of the guidewire remains sufficiently high to perforate through a certain thickness of tissue (e.g., between about 0.1 mm and about 15 mm). As described above, in some embodiments, the collar 4424b can also be formed of a heat conductive material, such as, for example, gold. This can allow heat to be wicked away from the tip of the guidewire, e.g., to avoid undesirable effects, as described above. In some embodiments, when the tip 4424a is extended less than about 5 mm beyond the distal end of the dilator or sheath, the current density at the conductive tip 4424a is greater than about 10 A/cm$^2$, or greater than about 20 A/cm$^2$, or greater than about 30 A/cm$^2$, or greater than about 40 A/cm$^2$, or greater than about 50 A/cm$^2$, or greater than about 60 A/cm$^2$, or greater than about 70 A/cm$^2$, or greater than about 80 A/cm$^2$, or greater than about 90 A/cm$^2$, or greater than about 100 A/cm$^2$, inclusive of all ranges and values therebetween. For example, the current density can be between about 10 A/cm$^2$ and 45 A/cm$^2$. For example, the current density can be between 5 A/cm$^2$ and 60 A/cm$^2$.

As shown in FIG. 42B, the guidewire can be extended a further distance beyond the distal end of the dilator 4426. As described above with reference to FIG. 8C, after the guidewire punctures or perforates through target tissue (e.g., a septum wall), the guidewire can be extended beyond the tissue. In some embodiments, the guidewire can be used as a delivery catheter for additional instruments. For example, the guidewire can be used to perform transseptal crossing, and then be used to guide additional instruments (e.g., electrosurgical or treatment devices, catheters, etc.) into the left atrium of the heart. In some embodiments, the guidewire can be extended a second distance of between about 5 mm and between about 15 mm from the distal tip. In some embodiments, the second distance is greater than about 7 mm. In some embodiments, when extended the second distance, the current density of the tip 4424a can be between 5 A/cm$^2$ and about 60 A/cm$^2$, inclusive of all ranges and values therebetween. For example, the current density can be less than about 20 A/cm$^2$. As another example, the current density can be less than about 30 A/cm$^2$.

When the guidewire is extended out this greater distance, as shown in FIG. 42B, the guidewire can be configured to assume an atraumatic shape, e.g., such as a J-shape, pigtail shape, etc. The atraumatic shape can be configured to reduce injury to nearby tissue structures. When the guidewire is extended out this greater distance, a distal conductive surface or portion 4424b of the guidewire is also exposed. This distal conductive portion 4424b can be the exposed surface of a metallic coil or other electrically conductive material. The coil can be electrically coupled to a core 4424c of the guidewire, as depicted in FIG. 42C. Therefore, energy delivered to the tip can be spread across the tip and the additional exposed conductive surface 4424d. As described above, this greater conductive surface area causes the current density to drop, and therefore further prevents and/or reduces the possible formation of lesions in nearby tissue structures. For example, when used in a transseptal crossing procedure, the greater exposed conductive surface area of the guidewire can reduce the likelihood of injuring the heart wall, as described above.

While the additional conductive surface 4424d is shown as the exposed surface of a coil in FIGS. 42B-42C, it can be appreciated that other conductive surfaces can be used to increase the total conductive surface area of the guidewire. For example, as described with reference to FIGS. 11A-11B and 40-41, the conductive surface 4424d can also be formed of an insulative coating that includes cutouts or patterns formed therein that exposed conductive elements underneath.

FIG. 42C provides a detailed cross-sectional view of the guidewire 4424. As shown in FIG. 42C, the core 4424c of the guidewire extends throughout a length of the guidewire. In some embodiments, the core 4424c can have a proximal section that has a larger diameter than a distal section. At or near a proximal end of the guidewire, the core 4424c can be exposed, such that the core 4424c can be placed in electrical communication with a generator (e.g., via any of the electrosurgical interfaces described herein, e.g., electrosurgical interfaces 122, 222, 322, 422, 522, 622, etc.). Alternatively, in some embodiments, the core 4424c can be covered by an insulating material but include one or more openings (e.g., holes, slots, or other cut-outs) that enable transfer of electrical current to the core 4424c, such as that described with reference to FIGS. 11A-11B above. The core 4424c can then be covered by an insulative coating or layer 4424e, such as, for example, a polymer. The insulative layer 4424e can cover the core 4424c until a distal segment of the guidewire. This distal segment can be between about 10 to about 100 cm in length, including all values and sub-ranges therebetween.

Starting at or near the start of the distal segment of the guidewire, the guidewire can transition from being covered by the insulative layer 4424e to having a conductive coil 4424d on the outside. The conductive coil 4424d, as described above, can be formed of a conductive material, such as a metal or metal alloy. The coil 4424d can then extend distally from the distal end of the insulative layer 4424e to the tip 4424a of the guidewire. As described above, the coil 4424d can be coupled to the distal tip 4424a such that the coil 4424d can form a long electrode or conductor with the tip 4424a. When the coil 4424d is exposed along with the tip 4424a, e.g., beyond the distal end of a dilator, the coil 4424d and the tip 4424a can provide a larger surface area over which energy or current delivered to the guidewire can be spread out, e.g., to reduce a current density at the tip 4424a. As shown FIG. 42C, the core 4424c can taper along its length in the distal segment of the guidewire, e.g., to provide greater flexibility closer to the distal end of the guidewire. The collar 4424b can be disposed near or adjacent to the tip 4424a of the guidewire. In some embodiments, the collar 4424b can be disposed over the coil 4424d. In such embodiments, the coil 4424d may have a smaller outer diameter than in other regions, such that an outer diameter of the guidewire in the region of the collar 4424b does not change. In other embodiments, the guidewire 4424b may have a slightly larger diameter in the region of the collar 4424b.

Methods

Figure 12:
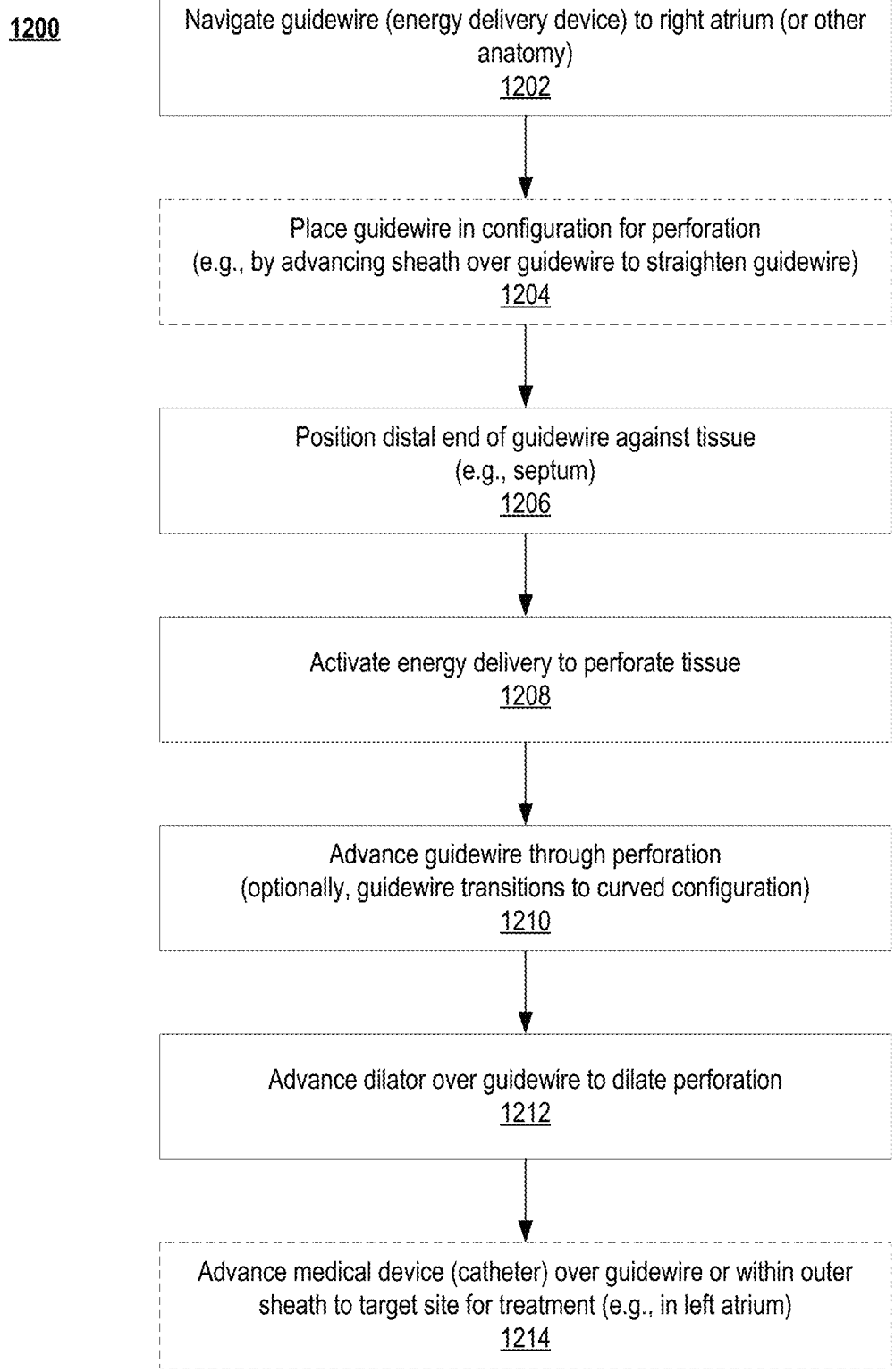
FIG. 12 is a flow chart depicting a method of using the electrosurgical system, according to embodiments.

FIG. 12 is flow chart of a method 1200 of using the systems and devices described herein, according to embodiments. The method 1200 includes navigating a guidewire (e.g., functionally and/or structurally similar to the energy delivery element 124 of FIG. 1 or other guidewires described herein) through vasculature to a right atrium (or other anatomy) of a patient at 1202, optionally placing the guidewire in configuration for perforation (e.g., by advancing a sheath over guidewire to straighten the guidewire) at 1204, positioning a distal end of the guidewire against tissue (e.g., a septum) at 1206, activating energy delivery to perforate the tissue at 1208, advancing the guidewire through the perforation at 1210, advancing the dilator over the guidewire to dilate the perforation at 1212, and optionally advancing a medical device (e.g., catheter) over the guidewire to a target site for treatment at 1214.

At 1202, the guidewire is navigated to a target location in a patient's body. The target location may be the right atrium of the heart or other patient anatomy (e.g., in the heart, vasculature, or other anatomy). In some embodiments, the guidewire is inserted into the femoral vein via a puncture created by a standard needle puncture technique. The guidewire is navigated or advanced through the vasculature using fluoroscopic and/or ultrasonic imaging. The guidewire can be navigated through the vasculature and positioned above the right atrial chamber in the superior vena cava (SVC).

Before or after navigating the guidewire to the right atrium (or other anatomy), the guidewire may be connected to a generator, e.g., via an electrosurgical interface (e.g., electrosurgical interface 122, 222, etc.). To connect the guidewire to receive energy from the generator, an intervascular sheath and/or dilator (e.g., sheath 126, dilator 426, etc.) can be prepared by attaching the electrosurgical interface to the lumen of the sheath via standard Luer connections. In some embodiments, the fluid lumen is flushed with a sterile 0.9% sodium chloride saline solution such that air in the lumen is removed. The sheath is then loaded on the proximal end of the guidewire and advanced into the patient's vasculature such that the distal tip of the dilator is positioned in the right atrium.

In some embodiments, as described above, the guidewire can have a J-shape or other atraumatic distal end shape. In such embodiments, it may be necessary to first place the guidewire in a specific configuration before the guidewire can be used to perforate through tissue. As such, at 1204, the guidewire optionally is placed in a configuration for perforation (e.g., a straightened or substantially straightened configuration). In some embodiments, placing the guidewire in the configuration for perforation includes advancing the sheath as described above over the distal curved portion of the guidewire to straighten the guidewire. In some embodiments, placing the guidewire in the configuration for perforation includes retracting the guidewire into the sheath such that the guidewire straightens. When positioned for perforation, the guidewire tip can be exposed about 1 to about 2 mm from the distal end of the dilator. Alternatively, in some embodiments, the guidewire may not have a J-shape construction. In such embodiments, it may not be necessary to move the guidewire relative to the sheath to straighten the guidewire or place it into a configuration for perforation. As such, 1204 can be omitted.

At 1206, the distal end (e.g., tip) of the guidewire is positioned against tissue. In some embodiments, the tissue is a portion of the interatrial septum of the heart. In some embodiments, the sheath may be a steerable sheath and/or dilator and therefore can be utilized to position or direct the guidewire toward the tissue, e.g., by actuating a steering mechanism (e.g., pull wires) on the sheath to deflect the distal portion of the sheath. In some embodiments, a pull-down technique is performed, in which the distal end of the dilator is directed toward the fossa ovalis (FO), and tenting of the tissue (e.g., septum) is facilitated via fluoroscopic and/or ultrasound imaging (e.g., as shown in FIG. 8B). In some embodiments, repositioning of the dilator may be desired by the operator after performing the tenting. To reposition, the guidewire may be re-advanced into the SVC and the pull-down technique may be repeated.

At 1208, energy delivery is activated to perforate the tissue. The perforation is formed by the tip of the guidewire delivering energy to the tissue and forming the perforation. In some embodiments, the electrosurgical energy is applied by actuating a button or other actuator connected to the electrosurgical interface (e.g., button 422*b*). In some embodiments, the perforation is formed by applying energy and applying a slight pressure on the tissue with the guidewire. Energy delivery is stopped once a puncture is formed within the tissue. In some embodiments, the formation of the puncture may be confirmed via imaging and/or tactile feel.

At 1210, the guidewire is advanced through the perforation formed in 1208. In some embodiments, the guidewire transitions to back to its curved configuration (e.g., as shown in FIG. 8C). In some embodiments, the guidewire is advanced through the FO and positioned in the left atria or the pulmonary veins. At 1212, the sheath implemented with a dilator can be advanced over the guidewire to dilate the perforation. In some embodiments, the dilator is advanced through the FO and positioned in the left atrium.

In some embodiments, the dilator and the electrosurgical interface can be retracted and removed, and additional devices (e.g., catheter and/or sheaths) can be advanced over the guidewire and into the left atrium (or other target anatomy), at 1214.

In some embodiments, an outer sheath may be positioned around the dilator and/or guidewire and advanced into the left atrium, e.g., at the same time as the dilator or shortly thereafter. This outer sheath may be positioned over the dilator and/or guidewire after the perforation has been formed and dilated and the electrosurgical interface has been removed from the proximal end of the dilator. Alternatively, this outer sheath may have been positioned over the dilator from the beginning of the procedure and used together with the dilator at 1204, 1206, and 1212. In such embodiments, the outer sheath can be used to provide an access passage or channel into the left atrium. The dilator and the guidewire are removed from the outer sheath, while the sheath lumen remains in the left atrium. At 1214, a medical device (e.g., a catheter, etc.) is advanced through the sheath lumen and to a target site for treatment.

In some embodiments, a therapeutic ablation catheter is advanced into the left atrium so that a pulmonary vein isolation may be performed. Once a procedure is performed, the medical device is removed.

Figure 13:
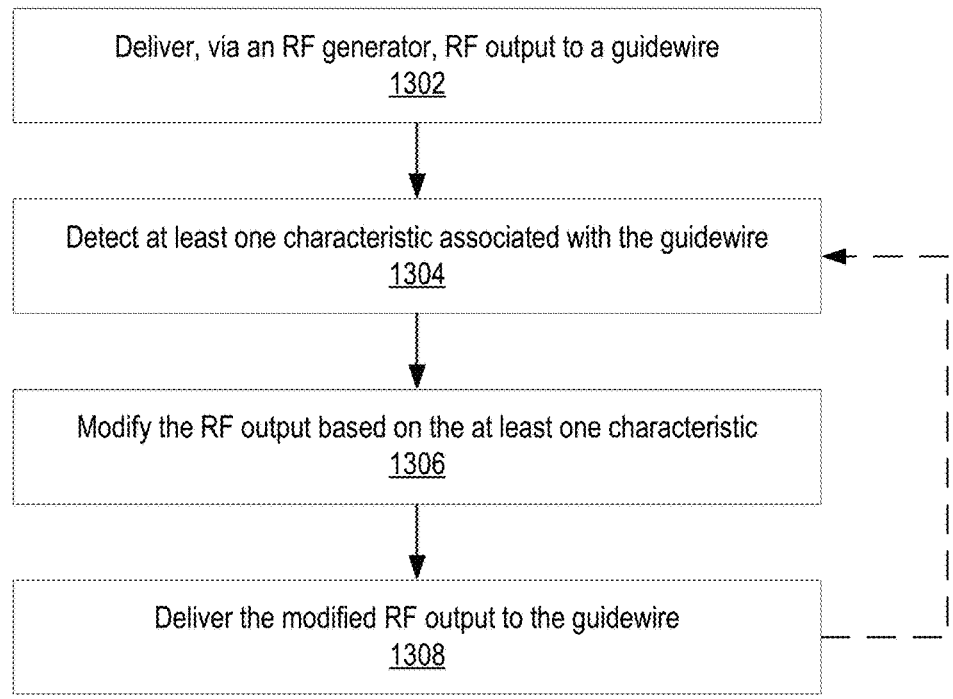
FIG. 13 is a flow chart depicting a method of varying a RF output being delivered to a guidewire, according to embodiments.

Referring generally to FIGS. 13 and 14, it may be beneficial to alter the energy delivered from a generator (e.g., functionally and/or structurally similar to the generator 110 of FIG. 1) to the guidewire (e.g., functionally and/or structurally similar to the energy delivery element 124 of FIG. 1). In some embodiments, it may be desirable to alter the energy being delivered to the guidewire tip based on measured properties such as, for example, temperature. This can help avoid buildup of heat at a distal tip of the guidewire, thereby preventing undesirable formation of microbubbles. In some embodiments, it may be desired for the guidewire to deliver a varied amount of energy to the tissue. For example, when the guidewire's distal tip is in-line or slightly past the tip of the sheath (e.g., about 1 mm), the guidewire has a small effective surface area, which can cause a high potential current density and thus heating near the guidewire tip. As the guidewire extends out of the sheath, the exposed surface area of the guidewire increases, thereby decreasing current density. To control the potential changes in current density, it may be beneficial to alter the energy delivered to the guidewire to prevent inadvertent damage to the tissue by the guidewire.

FIG. 13 depicts a flowchart of a method 1300 of varying an RF output being delivered to a guidewire, according to embodiments. The method 1300 includes modifying the output based on at least one characteristic associated with the guidewire. In some embodiments, the guidewire can include at least one sensor to measure the at least one characteristic (e.g., a state of the guidewire, temperature). In some embodiments, the sensor can be configured to capture data indicative of the at least one characteristic and send that data to the generator, which in response to receiving the data, may adjust the energy being delivered to the guidewire.

At 1302, the method 1300 includes delivering, via an RF generator, RF output to a guidewire. In some embodiments, the amount of RF output delivered to the guidewire can be predetermined. In some embodiments, the amount of RF output delivered to the guidewire can be determined based on a predetermined parameter (e.g., patient parameter, device parameter, etc.). At 1304, the method 1300 includes detecting at least one characteristic associated with the guidewire. In some implementations, the at least one characteristic can be an RF current, an RF output, temperature, current density, pressure, current, voltage, and/or the like. In some implementations, the at least one characteristic of the can be a state of the guidewire. For example, the state can include inside a sheath, starting to advance from a sheath, engaging tissue, and/or the like). As another example, the at least one characteristic can include current density at/around the tip of the guidewire.

At 1306, the method 1300 includes modifying the RF output based on the at least one characteristic. Modifying the RF output can include modifying an output power, peak-to-peak voltage, duty-cycle, and/or the like. For example, if the temperature at the tip of the guidewire is determined to be greater than a predetermined threshold, the RF output can be modified to deliver less power to the guidewire. As another example, if a pressure sensor detects that the septum of a heart has been punctured, the RF output can be decreased to decrease the likelihood of accidental damage. As another example, the RF output can be modified based on the current density at/around the tip of the guidewire and based on the location of the guidewire tip. For example, if the guidewire tip is in contact with the heart wall and the current density is greater than desired (e.g., such that it may form a lesion, the RF output can be decreased. After the RF output is modified, the method 1300 includes delivering the modified RF output to the guidewire at 1308. After the RF output is delivered to the guidewire, the method 1300 may return to 1304 to again detect at least one characteristic associated with the guidewire. Repeating steps 1304-1308 allows the system to dynamically change based on the detected at least one characteristic to decrease the likelihood of damage tissue.

FIG. 14 depicts a flowchart of a method 1400 of delivering an RF output to a guidewire, according to embodiments. The method 1400 includes altering the output to the guidewire based on an output schedule. This allows a predetermined amount of energy to be delivered during different stages of a procedure. In some embodiments, the output schedule is predetermined. In some embodiments, the treatment schedule can be modified based on the patient, device, and/or the like. In some embodiments, the treatment schedule can be defined by a user. At 1402, the method 1400 includes delivering, via an RF generator, RF output to a guidewire at first power parameters for a first period of time.

At 1404, the method 1400 includes delivering, via the RF generator, RF output to the guidewire at a second power parameters for a second period of time. At 1406, the method 1400 optionally includes delivering, via the RF generator, RF output to the guidewire at a third power parameters for a third period of time. In some embodiments, the method 1400 can include additional steps for delivering RF output to the guidewire at additional power parameters for additional periods of time. The power parameters can correspond to duty-cycles. The periods of time can correspond to durations associated with the operation of the guidewire. For example, the first power parameters can include a 10% duty cycle, the second power parameters can include a 50% duty cycle while the first period of time is 25% of the duration of treatment and the second period of time is 75% of the duration of treatment.

Additionally or alternatively, in some embodiments, a generator (e.g., generator 110 as described herein) can detect when the current density at the distal end of the guidewire decreases (e.g., as the conductive region of the surface area increases due to cutting through tissue) and can adapt to deliver more current up to a predefined or user-programmed limit. When the wire has lower surface area exposed, less current may be needed, but as the wire extends into the tissue, the increasing surface area may need more current to maintain a current density effective for perforating through the tissue. When the wire is fully deployed (e.g., 1 cm from the dilator or other insulating shaft tip), the current density is too low to cause inadvertent tissue damage, even with the higher RF output.

It should be understood that the examples and illustrations in this disclosure serve exemplary purposes and departures and variations can be built and deployed according to the teachings herein without departing from the scope of this invention. For example, while systems disclosed herein are shown having a unipolar configuration where the electrical circuit is completed by a remotely located return electrode placed externally on a patient, in alternative embodiments, such systems can have a bipolar configuration where a return electrode is placed internally in a patient, such as, for example, a metallic ring electrode disposed on a sheath, dilator, or catheter.

As used herein, the terms "about" and/or "approximately" when used in conjunction with numerical values and/or ranges generally refer to those numerical values and/or ranges near to a recited numerical value and/or range. In some instances, the terms "about" and "approximately" mean within ±10% of the recited value. For example, in some instances, "about 100 [units]" may mean within ±10% of 100 (e.g., from 90 to 110). The terms "about" and "approximately" may be used interchangeably.

Some embodiments described herein relate to a computer storage product with a non-transitory computer-readable medium (also may be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also may be referred to as code or algorithm) may be those designed and constructed for the specific purpose or purposes. Examples of non-transitory computer-readable media include, but are not limited to, magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices. Other embodiments described herein relate to a computer program product, which may include, for example, the instructions and/or computer code disclosed herein.

The systems, devices, and/or methods described herein may be performed by software (executed on hardware), hardware, or a combination thereof. Hardware modules may include, for example, a general-purpose processor (or microprocessor or microcontroller), a field programmable gate array (FPGA), and/or an application specific integrated circuit (ASIC). Software modules (executed on hardware) may be expressed in a variety of software languages (e.g., computer code), including C, C++, Java©, Ruby, Visual Basic®, and/or other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. Additional examples of computer code include, but are not limited to, control signals, encrypted code, and compressed code.

The specific examples and descriptions herein are exemplary in nature and embodiments may be developed by those skilled in the art based on the material taught herein without departing from the scope of the present invention, which is limited only by the attached claims.

The invention claimed is:
1. A method, comprising:
   extending a distal tip of a guidewire disposed within an insulating sheath a first distance distal to a distal end of the insulating sheath, the guidewire including a conductive outer region and an insulating collar disposed between the distal tip and the conductive outer region, the distal tip of the guidewire and the distal end of the insulating sheath being disposed proximate to a septum of a heart of a patient;
   disposing the distal tip of the guidewire against the septum;
   delivering, after disposing the distal tip of the guidewire against the septum, radiofrequency (RF) energy to the septum via the distal tip;
   further extending the distal tip of the guidewire distally while delivering the RF energy to form a perforation in the septum; and
   in response to extending the distal tip of the guidewire a second distance distal to the distal end of the insulating sheath, exposing the insulating collar and at least a portion of the conductive outer region of the guidewire such that an exposed surface area of the portion of the conductive outer region reduces a RF current density around the distal tip of the guidewire.

2. The method of claim 1, further comprising:
   prior to delivering the RF energy to the septum, tenting the septum using the distal tip of the guidewire.

3. The method of claim 1, wherein the insulating sheath is a dilator, and further comprising:
   advancing the dilator over the guidewire and through the perforation to dilate the perforation.

4. The method of claim 1, further comprising:
removing, after forming the perforation, the insulating sheath from being disposed over the guidewire; and
advancing a surgical instrument over the guidewire and through the perforation to navigate the surgical instrument to a target site.

5. The method of claim 1, wherein a proximal portion of the guidewire is slidably disposed within a passage of an electrosurgical interface, the electrosurgical interface configured to establish an electrical coupling between a RF generator and the guidewire and to maintain the electrical coupling while the distal tip of the guidewire is extended distal to the insulating sheath.

6. The method of claim 5, wherein the conductive outer region is a first conductive outer region, and the guidewire further includes a second conductive outer region that is electrically coupled to the distal tip,
the passage of the electrosurgical interface being configured to contain a conductive fluid and to receive at least a portion of the second conductive outer region of the guidewire,
the electrosurgical interface configured to establish the electrical coupling when the portion of the second conductive outer region is received in the passage and disposed in the conductive fluid.

7. The method of claim 6, wherein the guidewire further includes an insulating outer region disposed proximal of the second conductive outer region, the insulating outer region configured to be grasped by a user to extend the distal tip end of the guidewire.

8. The method of claim 5, further comprising:
monitoring, at the RF generator, an electrical property associated with the guidewire while delivering the RF energy; and
modulating the RF energy based on the electrical property.

9. The method of claim 8, wherein the electrical property being monitored is an impedance of a circuit formed by the RF generator, the electrosurgical device, and a return electrode coupled to the patient, and
modulating the RF energy includes, in response to determining that the impedance is greater than a predetermined threshold, reducing a voltage output of the RF generator such that a power associated with the circuit is below or equal to a predetermined value.

10. The method of claim 5, further comprising:
monitoring a temperature of the distal tip of the guidewire; and
modulating the RF energy based on the temperature.

11. The method of claim 10, wherein modulating the RF energy includes adjusting a voltage output of the RF generator such that the temperature of the distal tip remains within a target set point range.

12. The method of claim 1, wherein the insulating collar is between about 2 mm and about 5 mm in length, such that the insulating collar prevents a reduction in the RF current density around the distal tip of the guidewire when the distal tip of the guidewire is extended less than about 5 mm distal to the distal end of the insulating sheath.

13. The method of claim 1, wherein the insulating collar is electrically insulating and thermally conductive, such that the insulating collar prevents discharge of the RF energy from the distal tip along an exposed portion of the insulating collar while enabling dissipation of heat from the distal tip.

14. The method of claim 1, wherein the insulating collar is formed of at least one of a diamond, a metal with a diamond-like carbon coating, or a heat-conducting thermoplastic.

15. The method of claim 1, wherein the conductive outer region includes at least a portion of a metallic coil, the metallic coil being coupled to the distal tip.

16. The method of claim 15, wherein the insulating collar is disposed over a portion of the metallic coil and forms a flush surface with the conductive outer region.

17. The method of claim 1, wherein the insulating collar is stiffer than other components of the guidewire such that a stiffness of the guidewire is greater along the insulating collar than in regions proximal to the insulating collar.

18. The method of claim 1, wherein the first distance is less than about 5 mm, and when the distal tip of the guidewire is extended less than about 5 mm from the insulating sheath, the current density of the distal tip is greater than 30 A/cm$^2$.

19. The method of claim 18, wherein the second distance is greater than about 7 mm, and when the distal tip of the guidewire is extended greater than 7 mm from the insulating sheath, the current density of the distal tip is less than 30 A/cm$^2$.

* * * * *